United States Patent [19]

Valente et al.

[11] Patent Number: 5,615,005
[45] Date of Patent: Mar. 25, 1997

[54] GEMSTONE EVALUATION SYSTEM

[75] Inventors: Kevin A. Valente; Ernest R. Reuter, both of Kirkwood, Calif.; Randall M. Wagner, Mequon, Wis.

[73] Assignee: UGTS, Inc., Milwaukee, Wis.

[21] Appl. No.: 376,826

[22] Filed: Jan. 23, 1995

[51] Int. Cl.⁶ .............. G01W 21/00; G01J 3/46; G01N 21/87
[52] U.S. Cl. ............................. 356/30; 356/425
[58] Field of Search .................. 256/30; 73/104; 63/32; 356/303, 305, 328, 416, 418, 419, 425

[56] References Cited

U.S. PATENT DOCUMENTS

| | | | |
|---|---|---|---|
| 4,291,975 | 9/1981 | Raccah | 356/30 |
| 4,394,580 | 7/1983 | Gielisse | 250/461.1 |
| 4,652,913 | 3/1987 | Saitoh et al. | 356/425 |
| 4,906,093 | 3/1990 | Trossarelli | 356/30 |
| 5,118,181 | 6/1992 | Yifrach et al. | 356/30 |
| 5,124,935 | 6/1992 | Wallner et al. | 364/525 |
| 5,148,288 | 9/1992 | Hannah | 356/425 |
| 5,164,586 | 11/1992 | Hohbert et al. | 250/226 |
| 5,237,407 | 8/1993 | Crezee et al. | 356/425 |
| 5,414,778 | 5/1995 | Schwartz et al. | 356/427 |

Primary Examiner—Frank Gonzalez
Assistant Examiner—Jason D. Eisenberg
Attorney, Agent, or Firm—Andrus, Sceales, Starke & Sawall

[57] ABSTRACT

A device and method for grading gemstones. The device utilizes an band pass filter and detector array to obtain the spectral response of a complete image. The gemstone is illuminated in a way that provides for analysis of both reflected and transmitted light. The device utilizes multiple lighting angles to construct an composite image that is used to perform the grading of the gemstone. The device provides spectral photometric data for each individual pixel of the image, or any portion of the gemstone image.

26 Claims, 11 Drawing Sheets

COMPUTER SYSTEM ARCHITECTURE

GEMSTONE EVALUATION SYSTEM

A portion of the disclosure of this patent document contains material which is subject to copyright protection. The copyright owner has no objection to the facsimile reproduction by anyone of the patent document of the patent disclosure as it appears in the Patent and Trademark Office file or records, but otherwise reserves all copyright rights whatsoever.

A computer program is filed with this application and is incorporated into the specification by reference.

BACKGROUND OF THE INVENTION

The present invention relates to evaluation of gemstones and other transparent specimens and in particular to color grading of gemstones.

The commercial value of a gemstone depends upon the gemstone weight, cut, clarity and color. Highly trained specialists, known as graduate gemologists evaluate these and other stone properties such as finish to asses a value or grade for the stone. Small changes in any of these evaluation parameters can translate into a large change in stone price. For example, there has been a large increase in colored diamond traffic in recent years. Color, more than anything else, determines the value of a colored diamond. A small change of hue can mean a price change of thousands of dollars. Because of the sensitivity of gemstone value to grading criteria, in particular color, consistent and reliable grading of gemstones is of particular importance to the industry.

Certain of the evaluation criteria lend themselves readily to objective measure. For example, stone weight is measured in units of carats where five carats equal one gram. Clarity describes a stone's internal imperfections other than cleavage or fracture. Although the impact of imperfections on the stone's commercial value may vary slightly from gemologist to gemologist, the imperfections, such as included minerals and trapped gas, are readily visible by inspection and easily described in a standardized language. Gem color, however, does not as readily lend itself to uniform description among gemologists. Gemstone color remains a difficult property to assess and describe based on visual perception of the stone color because a variety of environmental, physiological and cultural factors combine to uniquely influence the gemologist's perception of stone color.

Environmental factors influencing color perception include the lighting conditions under which the stone is viewed. The stone's perceived color is a function of light temperature and spectrum. Daylight Kelvin temperature fluctuates dramatically from about 2000° K. to 25000° K. Because of this wide fluctuation, gem dealers buying stones in Thailand under a hot sun are frequently disappointed in the gem colors upon return to the United States. Lighting sources also emphasize certain colors and de-emphasize other colors depending upon the spectral emissions of the light source itself. For these reasons, a gemstone viewed under two different light sources may produce two different impressions of gem color.

Physiological factors also influence the gemologists color perception. Physiological factors derive from the limitations of the human eye as a measuring instrument and the unique variations of that measuring instrument between individuals. The human eye is limited in the degree to which it can distinguish subtle gradations in color. Furthermore, the wavelength of light at which the color receptors of the eye have maximum sensitivity vary from individual to individual. This variation also results in different color perceptions among individuals.

Another physiological limitation is the capacity of the human brain to interpret and process color. For example, the human brain cannot "remember" a given color. On a day to day basis, the "remembered" color shifts in a random direction. Hence, although the human brain can match two stones by direct comparison, the human brain cannot match two colored stones from memory. This limitation is of particular concern when choosing and matching gemstones for jewelry (i.e., a pair of earrings).

In addition to physiological factors, cultural influences also affect the gemologist's perception of a gem color. In certain societies, color plays a more important role than in other societies. Persons in color sensitive cultures learn a color sensitivity and develop a color memory not shared by persons in other cultures. Some cultures also emphasize or devalue certain colors. Persons in those cultures may develop a skewed sense of color perception.

Even if all persons viewing the stone were to perceive the same color, there remains the problem of describing the color in some universally understood terminology. Gemologists evaluate and describe the stone's color using techniques and terminology promulgated by standards organizations. In the United States, the Gemological Institute of America (GIA) promulgates these standards. Under the GIA guidelines, gemologists describe the stone's predominant color using three parameters: hue, tone, and saturation. Hue is an attribute that describes how the stone appears to be similar to one, or to proportions of two, perceived colors: red, yellow, orange, green, blue and purple. Tone represents the lightness or darkness of hue. Standardized grading schemes structure tone according to a grading scale, having approximately ten divisions, ranging from light to dark. The light end of the scale is colorless and the dark end of the scale is black. Middle grapy occupies the central position. Tone represents the color saturation. More intense colors have less neutral gray mixed with the hue. Dull intensities have greater amounts of neutral gray mixed with the hue.

Typically, the gemologist judges these parameters by matching the stone's color to standardized color pallets representing various combinations of hue, tone and saturation. However, due to the thousands of possible combinations, and the inaccuracies of the human eye, only a limited subset of the universe of colors are represented in the standardized pallets.

One further attribute of gemstones complicates color grading. In most objects, color depends upon what wavelength of light reflects off the surface of the sample. Unlike most other objects of color, gemstone color depends upon light that travels through the stone and is either bounced back by the internal facets or is otherwise refracted by the stone. The multiple paths through the stone, give rise to perception of secondary colors in addition to the primary of dominant stone color. These secondary colors must also be evaluated and described by the gemologist.

Known work sheets are used for color grading which include recording of the gemologists personal evaluation of various significant value factors: including dominant and secondary colors, with comments on clarity information and various cut information. The worksheet information for a number of stones is typically assembled by a gem wholesaler and circulated to various potential purchasers in catalog form. Purchasers can then select stones for potential acquisition from this catalog.

Because the color grading and valuation of gemstones is complicated by the individualism of the gemologist's color perception and by the limitations of the descriptive terminology, the purchaser has limited confidence in the catalog stone grading information. The color picture is also subject to inconsistencies due to the lighting conditions, the chemical properties of the film and errors introduced in the reproductive process. For these reasons, a purchaser is seldom willing to rely solely on the written grading information when making a purchase. The purchaser typically arranges to have the stone shipped to him for inspection and can then verify that the stone meets his appraisal standards and his particular needs.

If the stone does not satisfy the prospective purchaser, the purchaser returns the stone and the dealer can then provide the stone to another prospective customer for inspection. Typically, a stone must be shipped to approximately twelve potential customers before finally being purchased. Each potential purchaser keeps the stone an average of one month. Thus, the typical stone circulates around the world for a period of sixteen months.(counting transportation time) before being purchased. This trading system consumes time and places the stone at risk of loss.

Reduced confidence in the grading not only results in economic inefficiencies in the gem industry itself but also complicates governmental functions and support industry operations. For example, if a stone description cannot be given with confidence, the police tasks of locating and verifying a stolen stone become difficult. Uncertain stone descriptions also cloud the underwriting of gemstones.

The current system of buying and selling gems can be improved if more standardization exists in the color grading of gemstones. With greater standardization and less subjectivity, the gem purchaser can place more confidence in the appraisal and description of the stone.

In addition, forced consistency in dealer's appraisals of stones would require the dealer to be up front about the stone's value, providing improved protection to both consumers and customs operations. Currently, stones are routinely transferred between countries at 1/10 of actual value to avoid duties and other taxes. A reliable and computerized valuation will contribute significantly to curb this practice.

Prior art that is relevant to gemstone evaluation includes U.S. Pat. No. 5,164,586 issued Nov. 17, 1992 to Hohberg. In this system, two point detectors are utilized to obtain a reference value and a color value for the subject. This system utilizes an integrating sphere with an internal light source and multiple light exit points. The reference point is located inside the sphere of the Hohberg patent and is influenced by the object color. The Hohberg system also obtains all spectral information from a single point reading, which does not therefore take into account the distribution of color throughout the material. Additionally, the Hohberg system utilizes a "Flash Lamp" which does not provide a continuous light which the present inventors consider should be used to measure the phosphorescence and fluorescence of gemstones.

Other prior art that is relevant is more fully disclosed in an abandoned U.S. patent application submitted by Kevin Valente (Ser. No. 07/884,781, filed May 15, 1992). A color camera is used to obtain tri-stimulus color information of an imaged gemstone. It has been determined that the collected data of the system is not capable of completely describing the color of objects outside the RGB(Red-Green-Blue) color space. A continuous light source is used which provides a single lighting angle for analysis.

SUMMARY OF THE PRESENT INVENTION

The present invention permits color analysis including grading of gemstones and other transparent specimen. Generally, a viewing unit includes a glass plate or other suitable viewing support upon which the gemstone is placed. The viewing support is enclosed in an analysis chamber comprising spherical surfaces. The analysis chamber is substantially void of light not produced by a proper light source. The gemstone is specially illuminated from a relatively moveable light source. The image of the gemstone in the analysis chamber is transmitted through a processing system which includes sequential selection of individual wavelengths, detecting the amplitude of each wavelength, and converting the amplitude signal into a form for subsequent processing.

In one aspect of the invention, the sequential selection of wavelengths is performed by a tunable band pass filter that only allows light of a programmed wavelength to pass through to a detector. The detector, such as a Charged Coupled Device (CCD), measures the amplitude of light at each wavelength and converts it to digital data that is processed by the computer. The output of a CCD unit provides a gray scale image at each individual wavelength. The video capture card or other suitable device converts the gray scale values for each pixel of the Jemstone to digital data. The computer then mathematically compares the frequency response to CIE standards, or other generally recognized standards, to arrive at a "color value" for each pixel of the CCD. The data for all pixels is then combined, preferably averaged, and presented in a standardized color nomenclature and standardized representations of hue, tone, and saturation. The data is processed to arrive at the individual hues for each part of the gemstone, particularly giving primary and secondary within the average hue of the gemstone. The data can be archived for subsequent retrieval as desired or needed. In this manner the color peculiarities of the gemologist's environment and personal attributes are minimized and a consistent mechanism for color evaluation provided.

A wide area network is preferably provided through which prospective buyers can access the system, such as utilizing standard phone lines. A digital image of the stone can then be transmitted to the buyer together with the standardized grading information. The digital image is of sufficient quality to accurately depict the stone. Buyer's have increased confidence in the grading information and are less likely to require that the stone be shipped for inspection prior to purchase or are at least more likely to keep the stone after inspection. The wide area network provides an electronic network sales package that allows more effective and efficient use of dealer's high price inventories and reduces the expense of traditional marketing methods.

BRIEF DESCRIPTION OF THE DRAWINGS

The drawings furnished herewith illustrate a preferred construction of the present invention in which the above advantages and features are clearly disclosed as well as others which will be readily understood from the following description of the illustrated embodiment.

In the drawings.

DESCRIPTION OF PREFERRED EMBODIMENTS

The illustrated embodiment of the present invention utilizes a CCD (Charged Coupled Device) detector to image the spectral information of the gemstone. The CCD in concert with a tunable optical band pass filter is used to obtain the spectral information of the stone which can then be translated to any color measurement reporting system that can be represented mathematically as a function of this information.

Description of Device Hardware.

Chart 1 shows a colored stone grading worksheet prepared according to the GIA (Gemological Institute of America).

CHART I

COLORED STONE GRADING WORKSHEET

| STONE # | | | VARIETY/SPECIES | |
|---|---|---|---|---|
| CUT | | | | |
| Dimensions | | | Depth | |
| | length/max | | weight ct. | |
| COLOR: | ADDITIONAL- | | | PHOTO-GRAPH |
| DOMINANT | 1 | | ADDITIONAL-2 | OF GEM |
| Hue | Color | | Count | |
| Tone | Strength | | Strength | |
| Saturation | Hue | | Hue | |
| Master Notation | Tone | | Tone | |
| Change of Color | Saturation | | Master Notation | |
| Comments: | | | | |
| | | | Grade # | |
| Description: | | | | |
| CLARITY: | | | | |
| Type | Description | Grade # | | |
| | | | Symbol Keys | |
| CUT: | | | | |
| PROPORTIONS | | | | |
| A. | Face-up Outline | C. | Profile | |
| | Balance | | Balance | |

CHART I-continued

COLORED STONE GRADING WORKSHEET

| STONE # | | | VARIETY/SPECIES | |
|---|---|---|---|---|
| CUT | | | | |
| Dimensions | | | Depth | |
| | length/max | | weight ct. | |
| COLOR: | ADDITIONAL- | | | PHOTO-GRAPH |
| DOMINANT | 1 | | ADDITIONAL-2 | OF GEM |
| | L-W Ratio | | Total Depth % | |
| | Appeal | | Crown Height | |
| | | | Pavilion Depth | |
| | | | Ratio | |
| B. | Brilliance # | | | |
| | Windowing | | Bulge | |
| | Extinction | | Table Size | |
| | Light Return | | Grade Thickness | |
| D. | Proportion Grade = A + B + C + 3 = Grade # | | | |
| FINISH | | | | |
| | Polish | Symmetry | | |
| | Facet Survey | Grade # | | |
| E. | Finish Grade # | | | |
| | CUT GRADE * = (D × 4) + (E × 1) + 8 − Grade # | | | |

\* Cut Grade cannot exceed Proportion Grade
\* It is acceptable to upgrade or downgrade on final judgement Region 1 is used to generally define the gemstone. In region 2 of the worksheet are located spaces for indicating the gemologist's evaluation of the dominant and secondary colors. The gemologist's determines the hue, tone, and saturation for the both the primary color, and any additional colors. Region 3 is used to describe the dimensional properties of the gemstone. Region 4 of the worksheet provides space for attaching a color photograph of the gemstone.

Figure 1:
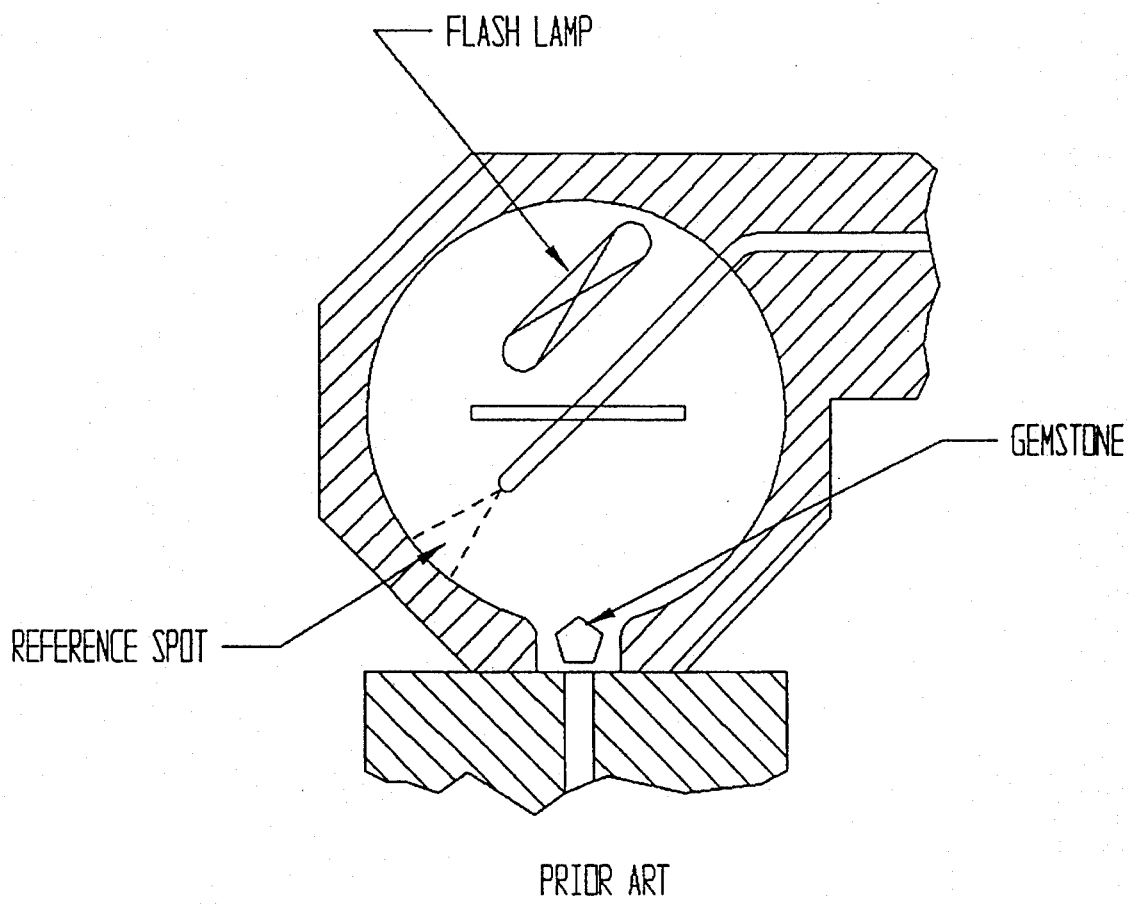
FIG. 1 is a sectional view of a prior art device.

The prior art Hohberg patent uses a fixed light source within the sphere and locates a reference point within the spherical enclosure and is influenced by the object color (FIG. 1). The present invention establishes an improved analysis by locating the reference point outside of the sphere. The present inventors also uses an external light source, which is movable to the gemstone. The present invention uses a common entrance and exit point for all light. The present device utilizes a single detector array for analysis and reference. The reference point is located external to the sphere in the present invention and essentially avoids any influence from the subject.

Figure 2:
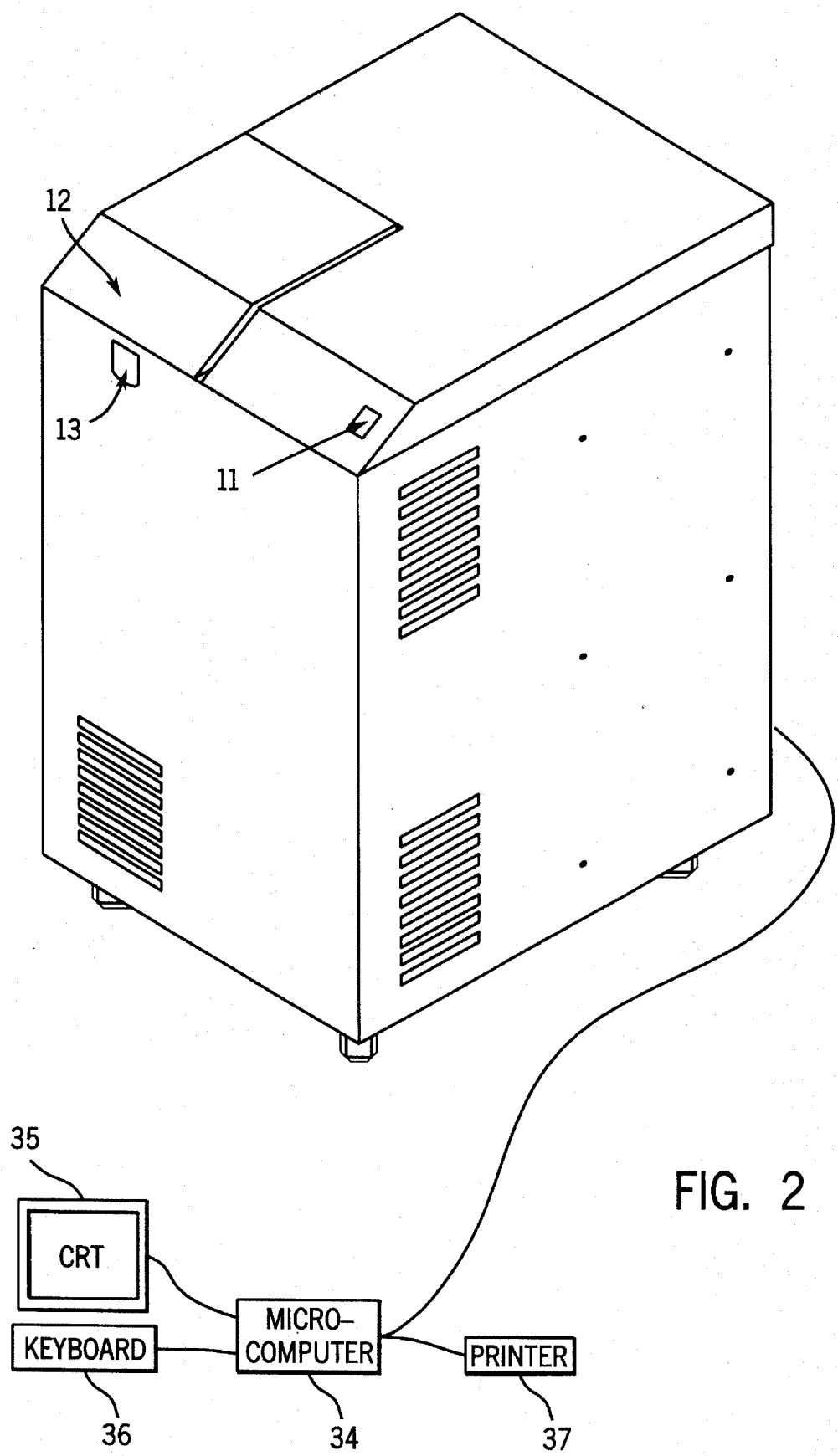
FIG. 2 is a three dimensional view of a gem stone color evaluation device according to an embodiment of the present invention.

FIG. 2 contains a view of the gemstone color evaluation system or device constructed according to the preferred embodiment of the present invention, which provides improved data for the second region of the worksheet and the conclusion of the nature of the gemstone. An illuminating and signal capturing cabinet 10 is shown with a main power switch 11 located on the top right corner of the cabinet. An access cover 12 is provided on the top left corner of the cabinet. Just below the cover is a recessed release button 13 for opening the chamber.

FIG. 2 also illustrates a typical signal processing system connected to an output of the signal captivating cabinet for analysis of the gemstone color. The system is more fully described and discussed hereinafter.

Figure 3:
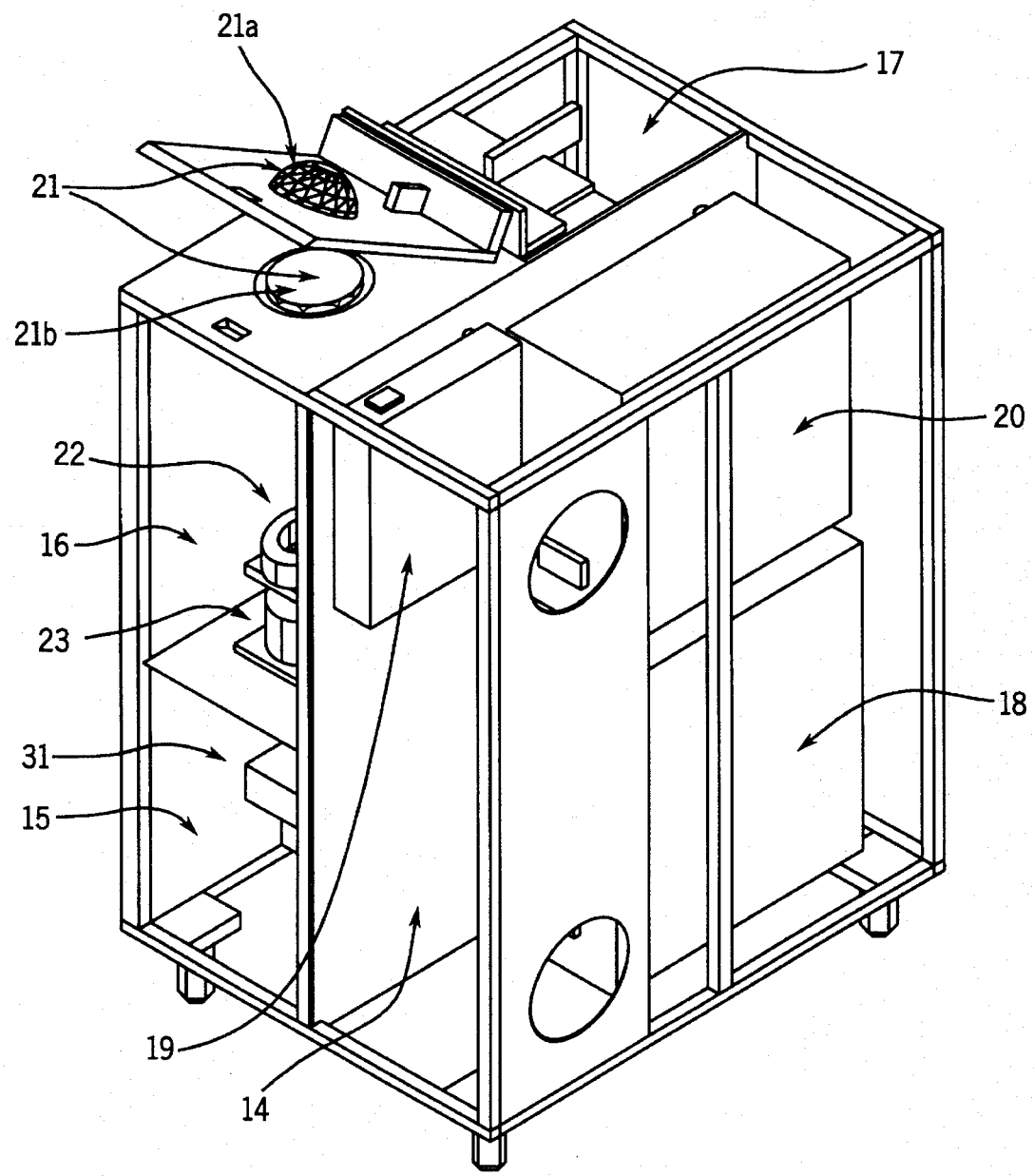
FIG. 3. is a three dimensional view of a gem stone color evaluation device with the "skin" removed and the gemstone chamber open according to an embodiment of the present invention.
Figure 4:
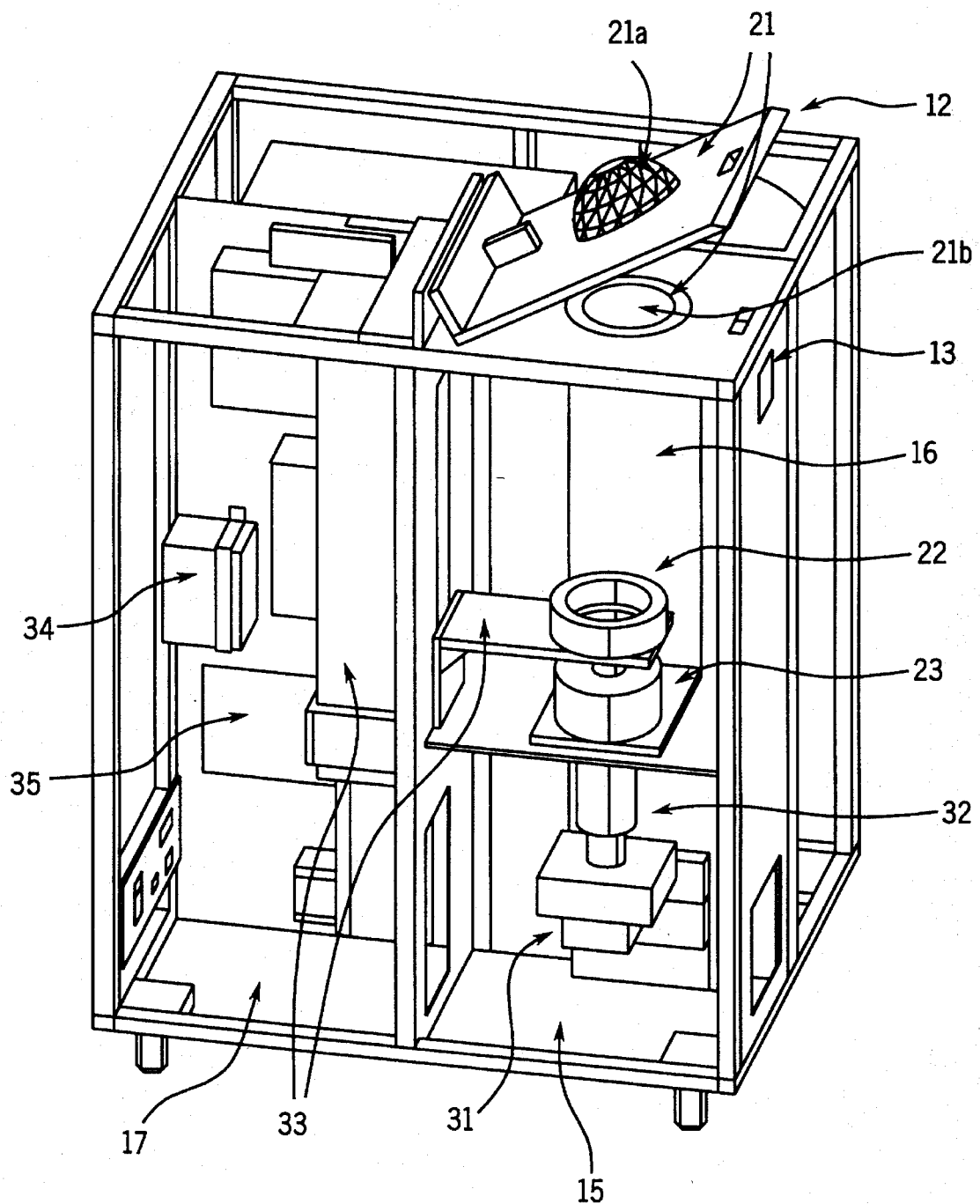
FIG. 4 is a three dimensional view of the left side of a gemstone color evaluation device.

FIG. 3. shows a 3 dimensional view of the device with the "skin" removed and FIG. 4 is a similar side view of the device viewed from the left side of FIG. 3. As shown in FIG. 3, the device is divided into four sections. The section 14 consisting of the right half of the device contains the light source be, and the control electronics. The control electronics includes a filter control 19 and a light motion control 20.

As shown in FIGS. 3 and 4, the left half of the machine is divided in to three compartments, the upper front 16, lower front 15, and the back 17.

The upper front chamber 16 contains the analysis chamber 21, an annular light ring 22 mounted on a moving platform, and an optical band pass filter 23. This front compartment is sealed to prevent dust and particle matter from entering. Although any well known method may be used, the interior walls of the compartment, as well as all objects contained therein are coated black to minimize reflected light within the compartment.

Figure 5:
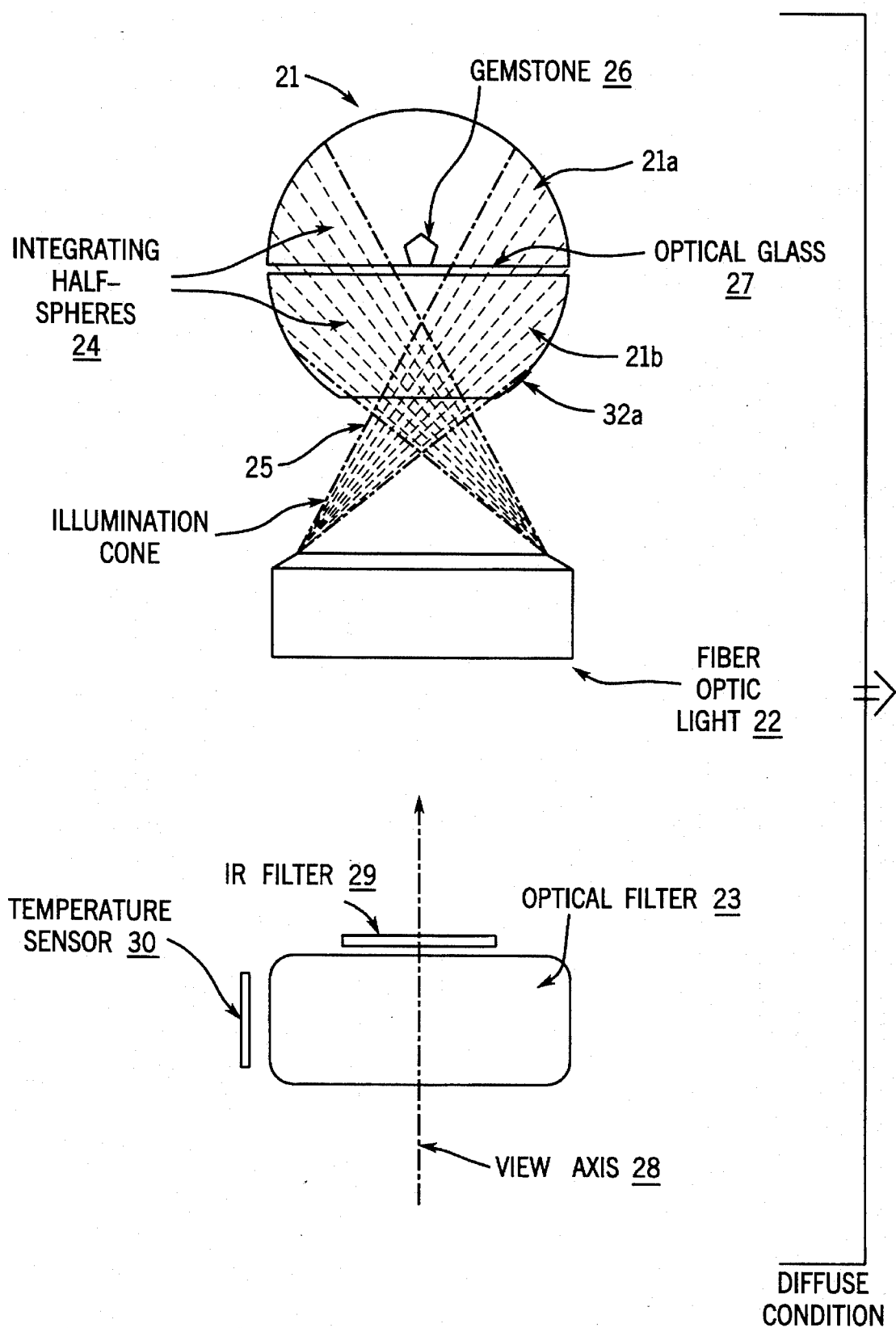
FIG. 5 is a side view of the analysis chamber, light ring and tunable filter with the light ring in the diffuse position according to a embodiment of the present invention.

Located at the top of this compartment is the analysis chamber 21. Chamber 21 is a two-piece unit including the upper and lower semispherical members 21a and 21b. FIG. 5 diagrammatically depicts the chamber 21 with a gemstone 26 in place relative to the annular light ring and filter. The chamber 21 consists of a spectraflect coated sphere 24 with single entry and exit aperture 25. The sphere is formed in two equal half parts with the top half of the sphere hinged to allow placement of the gemstone 26 to be evaluated. Centered in the chamber is a glass plate 27 on which the gemstone 26 to be evaluated is placed tableside down. Tableside down orientation is preferred because currently colored gemstones are graded by refracted light through the table. Although glass is preferred, other clear, transparent materials may be used, in any supporting structure.

The annular light ring 22 is mounted on a platform that is moveable in order to optimize lighting angles. The variable lighting positions of the gemstone could also be accomplished by moving the gemstone and chamber relative to the light ring. Gemstones are generally viewed by individuals from multiple angles, relative to light sources, to obtain the quality and color. The multiple position light source provides the device with the same capabilities.

Figure 7:
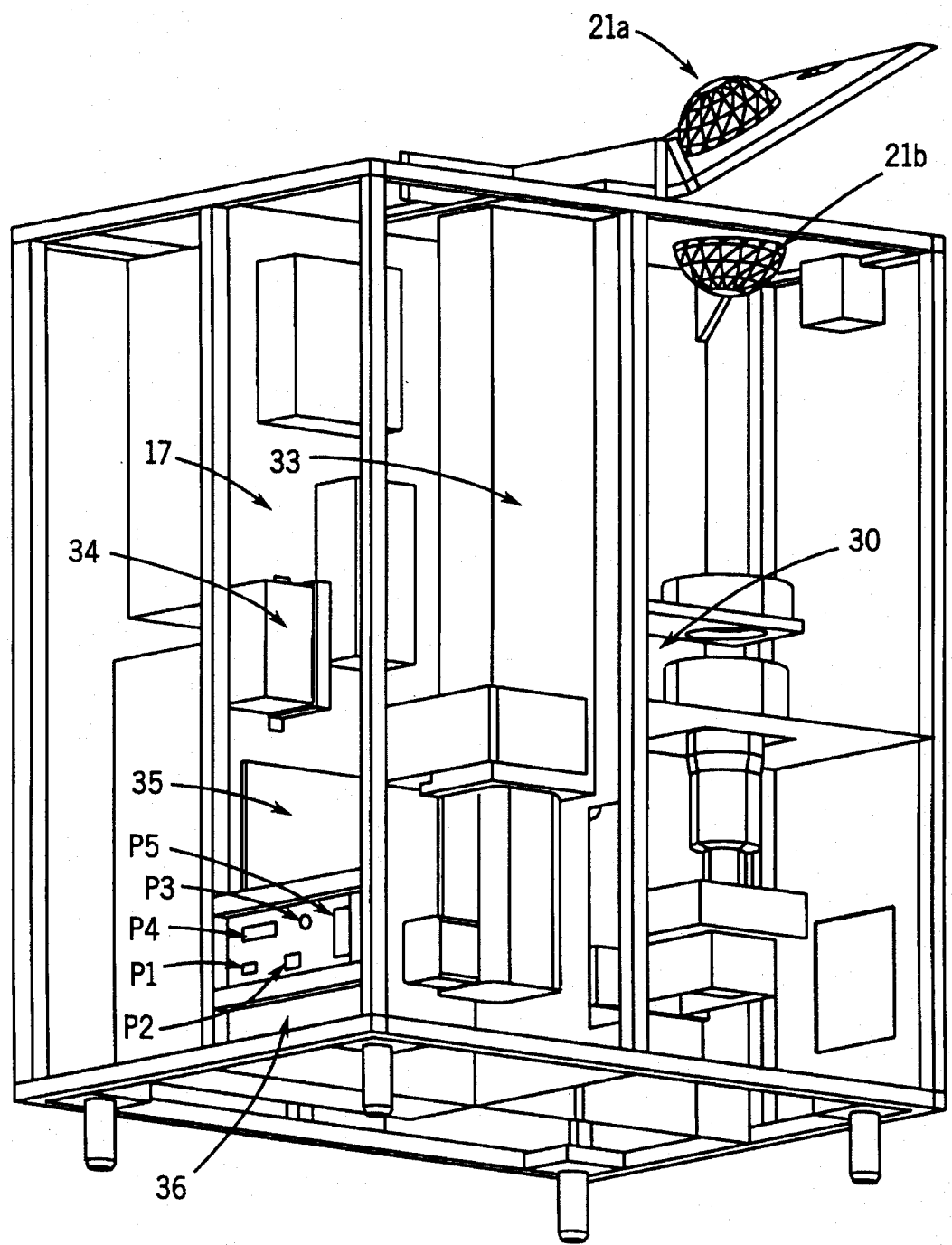
FIG. 7 is a back view of the interior of a gemstone color evaluation device according to an embodiment of the present invention.
Figure 9:
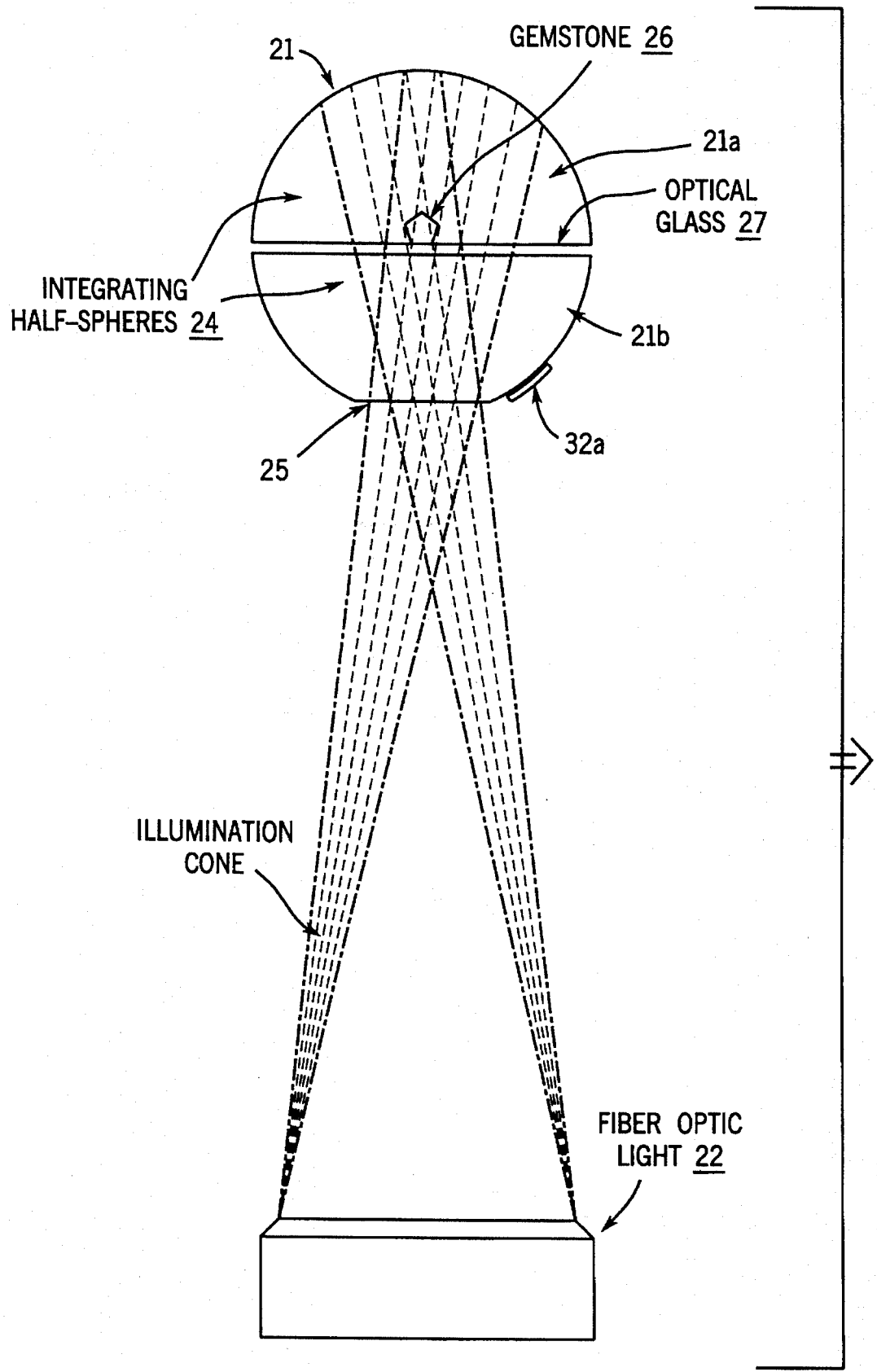
FIG. 9 is a diagram of the lighting patterns created when the light ring is in its most remote position from the analysis chamber, the reflectance position according to an embodiment of the present invention.

For optimum analysis of highly reflective gemstones, such as white diamonds, the lighting geometry is selected to produce a position which prevents the light from directly reflecting off the surface of the gemstone. Refraction of light through a gemstone gives the stone its color. Light reflected off the surface of the stone may distort the color analysis. The angular position of the light ring prevents light from reflecting off this surface and distorting the analysis when its in its upper most position as shown in FIG. 5. Positions that directly illuminate the gemstone, such as in FIG. 7, are required for less reflective gemstones. The "cones" of light that are shown in FIG. 5 and FIG. 9 are defined by the light ring 22 and the opening in the analysis chamber 21. The light ring 22 casts light off in all directions.

Although many colored gemstones are customarily evaluated as viewed from the tableside, certain gemstones, such as diamonds, have highly reflective surfaces and are not graded in this orientation. These stones are normally evaluated from the side to minimize external reflections. The tableside orientation is preferred not only due to custom, but because this orientation more closely resembles how the stone will appear when set. Because the construction of the present invention includes a light position which eliminates surface reflections, all stones may be graded with the stone in the preferred tableside up orientation, but can of course be otherwise positioned.

Referring to FIG. 5, the 360° geometry of the chamber and light ring are symmetrical along the viewing axis 28 to eliminate rotational sensitivity of the evaluation. In order to provide reliable and repeatable color information, it is necessary that the device is not sensitive to rotational position of the gemstone. It would be nearly impossible to repeat a measurement on a round stone if the device is sensitive to rotational position. The subject can be placed in the center of the chamber without regard to angular position. The geometry is designed such that the gemstone is illuminated from all angles uniformly when the light ring is in its upper most position as shown in FIG. 5. The light ring is of sufficient diameter to prevent any interference with the gemstone image projected upon the CCD.

Below the analysis chamber, approximately 12 inches, in a practical construction, is located the optical filter 23, as shown in FIG. 5. Any suitable filter may be used and at least several filter types are presently available in the art. A particularly satisfactory filter, in an embodiment of the invention, is a tunable imaging filter using liquid crystal technology. One filter assembly (Model No. VS-VISI-20-MC-20-RD) is manufactured by Cambridge Research Incorporated providing a 20 nanometer bandwidth and a range of 400–700 nm. As previously discussed with respect to FIG. 5, the control electronics of which only elements 19 and 20 are shown, also available from the same company for this filter, is located in the right compartment 14. The light ring 22, for practical cost effective implementation, is more fully described hereinafter. The light source generally outputs a very high level of infra-red light (above 700 nm) which the filter does not adequately block. Placed on the chamber side of the filter 23 is a glass notch filter 29 such as an IR filter, to further reduce the amount of infra-red light that reaches the CCD.

As shown in FIG. 5, located on the side of the filter 23 is a suitable electronic circuit 30 that serves as a temperature sensor. In the present invention, light travels through the medium of air. The refractive index of air changes with temperature, as does the performance of the filter. Regulation of the temperature is therefore desirable not only to cool the electronics but to maintain a substantially uniform and constant temperature within the cabinet. The present embodiment includes a fan which is activated under computer control to regulate the temperature within the compartment 16.

FIG. 4 shows a view of the invention from the left side. Directly below the optical filter 23 is located the CCD camera 31 and lenses 32 oriented with the lens aimed at the center of the analysis chamber 21. The centerline of the analysis chamber 21, filter 23, annular light ring 22, and CCD camera 31 assembly are common. Several CCD cameras are known in the art. The particular CCD camera chosen in a preferred embodiment of the invention, is a model No. TM 745.OP22-3 made by Pulnix with a 768×493 pixel image area and containing a programmable exposure time. The preferred camera includes peltier cooling to optimize signal to noise ratios in long exposures.

The annular light ring 22 is a fiber optic cable assembly providing an evenly distributed 360 degree light. The ring assembly delivers the light generated from the light source 18 located in the right half compartment 14. The light source is a broad band daylight simulator. Several suitable light sources are known in the art. The preferred embodiment utilizes a xenon source providing light at approximately 6000 degrees K. The Xenon light source provides a very "flat" spectral response across the visible spectrum from 400 nm to 700 nm. Because the instrument obtains a relative response to the light, it is not required that the light source has a "flat" response in order to obtain accurate spectral information.

The spectral response of a "reference spot" on the exterior of the spherical analysis chamber, such as shown at 32a, (as more fully developed hereinafter in connection with the description of one software program and FIG. 8) is determined when the device is calibrated. Spectral response is the output information and data based on the reflected light and particularly the level of the relfected light at each of the frequencies. This establishes the necessary data for evaluating each of the characteristics of a gemstone normally applied in evaluating a gemstone. This reference spot 32a is then used to obtain the light level at each frequency during the data capture. All data obtained is then compared to this "reference spot" to obtain accurate data for each frequency. This method eliminates the need for constant calibration as the light source ages or changes over time.

The light ring 22 is mounted on a single axis motion system 33 (shown in FIG. 4) to provide multiple lighting angles for the color analysis. The movement system is designed such that the lighting positions can vary from a diffuse position (where no direct light hits the table of the stone FIG. 5), to a reflectance position FIG. 9 (where the light beam is nearly centered on the stone). The particular motion system 33 used in the embodiment of the invention is a narrow profile single axis controller manufactured by Designatronics Techno Division, in Hyde Park, N.Y. The position slide and motor are controlled by the motion controller that interfaces to the computer through a RS-232 compatible serial data link.

The output of the camera 31 of FIG. 4 couples to a microcomputer 34, shown in FIG. 2 via an internal video capture card (not shown). Several video capture cards, suitable for use with the present invention are known in the art. A preferred embodiment of the invention uses a DT55-LC-60 frame grabber manufactured by Data Translation Corp. of Marlboro, Mass. Microcomputer 34 may be, for example, a Pentium based personal computer. Other microcomputers are suitable for use with the present invention. Also shown in FIGS. 2 and 4, a high resolution video display 35 terminal and keyboard 36 is preferably used to display the current CCD camera image in addition to inputting and displaying other commands and data.

Figure 6:
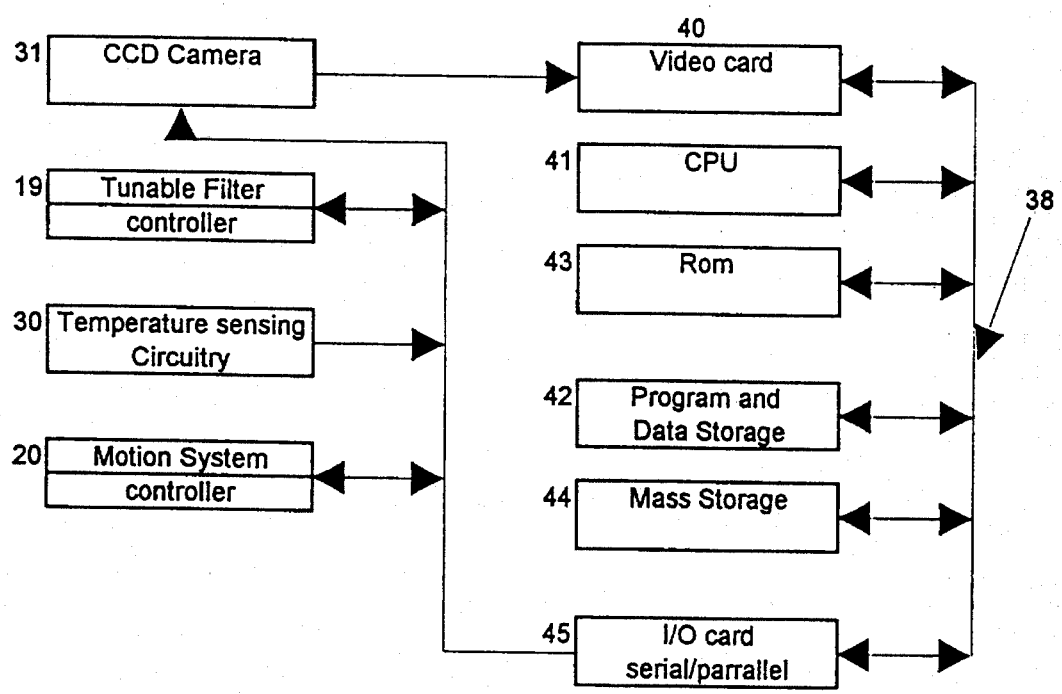
FIG. 6 shows a block diagram of a computer system architecture useful with the device of the present invention.

FIG. 6. shows a block diagram of the microcomputer system architecture for the devices of the present invention. Video card 40 receives analogue data from camera 31 and converts the signal to digital data via an analog-to-digital converter. The digital data is processed by the CPU 41 operating under control of software data stored in memory 42 which may be RAM. Program information may alternately be stored in ROM 43 and downloaded to RAM at power up or on reset according to conventional techniques and depending upon specific microcomputer design chosen. The processed data for each gemstone is archived in mass storage device 44 for later retrieval and transmission. Mass storage device 44 may be hard disk, optical disk, or other mass storage device known to those of skill in the art. The system elements are coupled by an address and data bus 38.

The I/O cards 45, one serial, one parallel, handle the interface to the camera 31, filter controller 19, motion controller 20, and temperature sensor 30. The filter and motion system are controlled via a RS232 type serial link. The temperature sensor circuitry and camera are controlled via parallel data bits.

FIG. 7 shows a back view of the device. Located on the back connector plate 36 are the connections required for power and interface to the external computer. Connector P1 is the serial data connection for the motion control. Connector P2 is the serial connection for the filter controller. Connector P3 is the video connection to the camera from the capture card. Connector P4 is connected to a parallel input/output card in the computer. This controls camera setting, on/off for chamber fan, and interface to temperature sensor 30. Connector P5 is the main power input that is connected to 120 VAC.

In the back compartment 17 shown in FIG. 7 contains the ring light motion system 33, filter power supply 34, and the power supply and distribution circuit board 35.

COLOR GRADING OF GEMSTONES

The light amplitude data for each CCD pixel is read from the image capture board into the computer memory and processed to obtain the gemstone information. The process of evaluation contains four major tasks for evaluating the color characteristics of the gemstone. These tasks include: determining the average response of the reference spot; determining the response of each pixel relative to this reference point; identifying the object from the background; and determining the average response of the object or specified area. These four major tasks each involve several sub-tasks.

Figure 8:
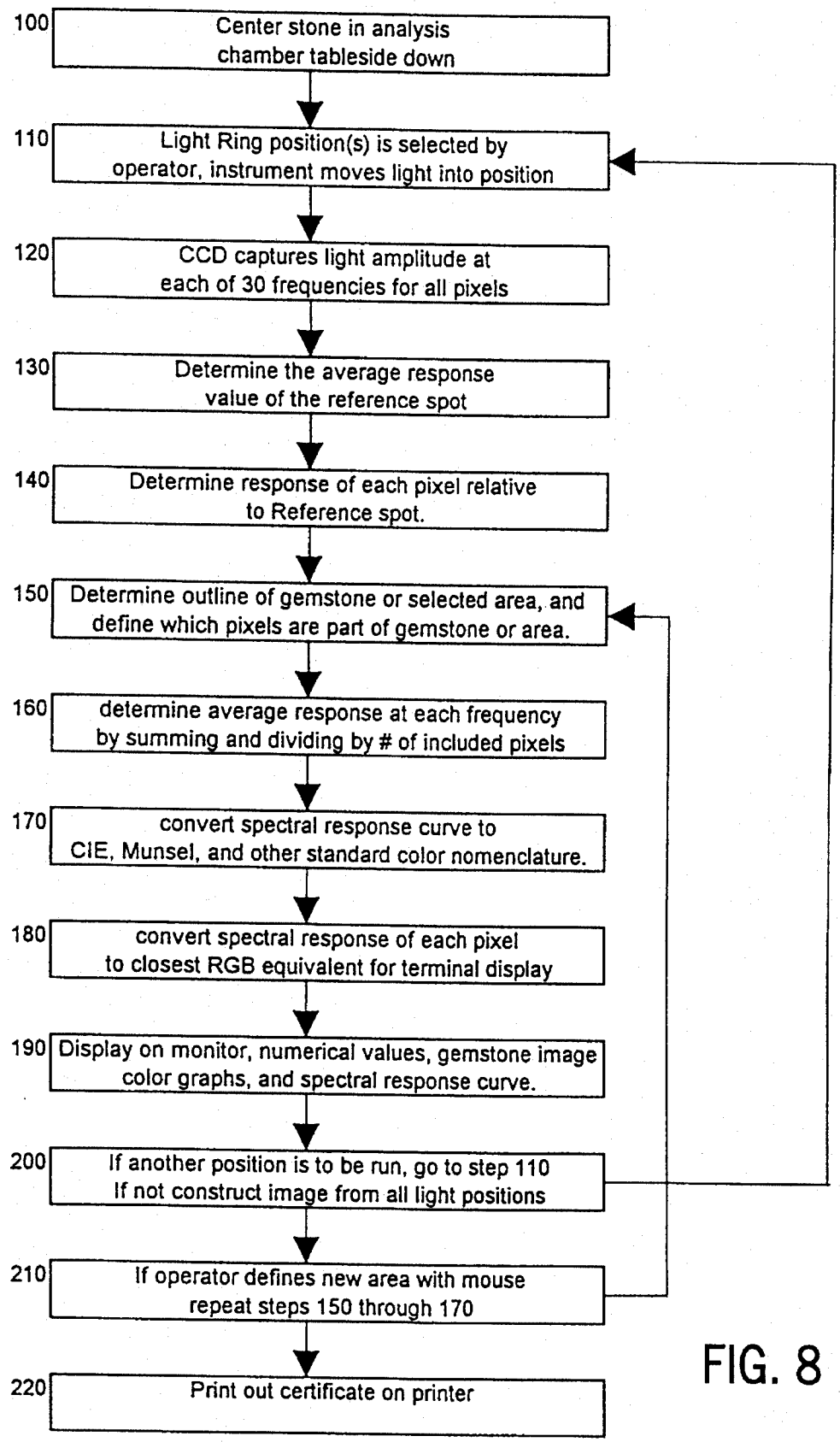
FIG. 8 is a flow chart of a method of evaluating colored gemstones according to an embodiment of the present invention.

FIG. 8 contains a flow chart of a method of evaluating the color of gemstones according to the embodiment of the present invention. A worker skilled in the art may readily provide a suitable software program for executing the program shown in FIG. 8 for the illustrated embodiment. A program presently prepared for executing various steps of the illustrated embodiment is filed herein to be made a part of the Patent Office file for reference purposes.

The gemologist places the gemstone tableside down on the glass of the analysis chamber and then closes the cover(step 100). The operator the selects the light position, step 110, or combination of light positions that will be used in the analysis. The device provides three standard default positions, however, the operator can choose to select non-standard positions. In step 120, the computer sets the filter to the desired wavelength and instructs the CCD to perform a capture. At the end of the programmed time, the CCD outputs to the video capture card in the computer, which stores the data in memory. This process is repeated for a substantial number, such as 31 times (until all wavelengths are captured).

The image that the CCD captures includes areas outside the analysis chamber as well as the opening in the sphere. In order to determine the response, the amplitude of the light the object in the analysis chamber is exposed to must be determined. The "reference spot" 32a is used to determine the light amplitude at each capture. The "reference spot" includes pre-defined collection of pixels located outside the chamber within the view of the CCD. The reference spot can be located within the sphere, but it is less desirable due to the influence of the gemstone on all light within the sphere. The response of the "reference spot" is periodically calibrated by placing optical standards such as presently available for standard gemstones in the chamber and running a calibration cycle. The data is adjusted based on the value stored in memory for the reference spot. In step 130, the average response for each wavelength is determined for the "reference spot".

In step 140, the response of each pixel relative to the reference is determined. The relative light amplitude is stored for later processing in step 150, and 180.

Step 150, response of each pixel obtained in step 140 is analyzed to define the outline of the gemstone. All points within the outline are considered part of the object regardless of response level.

In step 160, the average response of all included pixels is determined at each wavelength by summing the values and dividing by the number of included pixels.

In step 170, the response of each pixel obtained in step 140 is translated to it's closest RGB value (the amplitude of each of three colors Red, Green, Blue, that can be combined to form the specific color). Though not all gem colors can be represented by the RGB system, that is all that the monitor is capable of displaying. These 24 bit RGB values are then used to reconstruct the gemstone image on the video screen.

Step 180 converts the average value obtained in step 160 to CIE values. The CIE (Commission International de l'Eclairge) scale is a standard of color measurement, well known to those in the art, that represents color as three numerical values. Known data for performing this conversion may be found in several sources including: *Raster Graphics Handbook* 2nd ed., Conrac Division, Conrac Corp., Van Nostrand Reinhold Company, New York. The equations for conversion as used in an embodiment of the present invention are given in Appendix A.

Equations other than those given in Appendix B are possible to describe the CIE system. A discussion of the various possible equations may be found in *Principles of Color Technology*, 2ed. by Billmeyer and Saltzman, John Wiley an Sons, New York, 1981 and in International Commission on Illumination, *Method of Measuring and Specifying Colour Rendering Properties of Light Sources*, Publication CIE No. 13.2 (TC-3.2), Bureau Central de la CIE, Paris, 1974.

These equations are used to convert the spectral response obtained by the CCD to a universally recognized system of color description. In the recognized system, color description is obtained by a calibrated measuring instrument not subject to the physiological or cultural conditioning of the gemologist and gives a consistent mathematically defined description of color when a standard illumination, defined by the CIE, is used.

Figure 10:
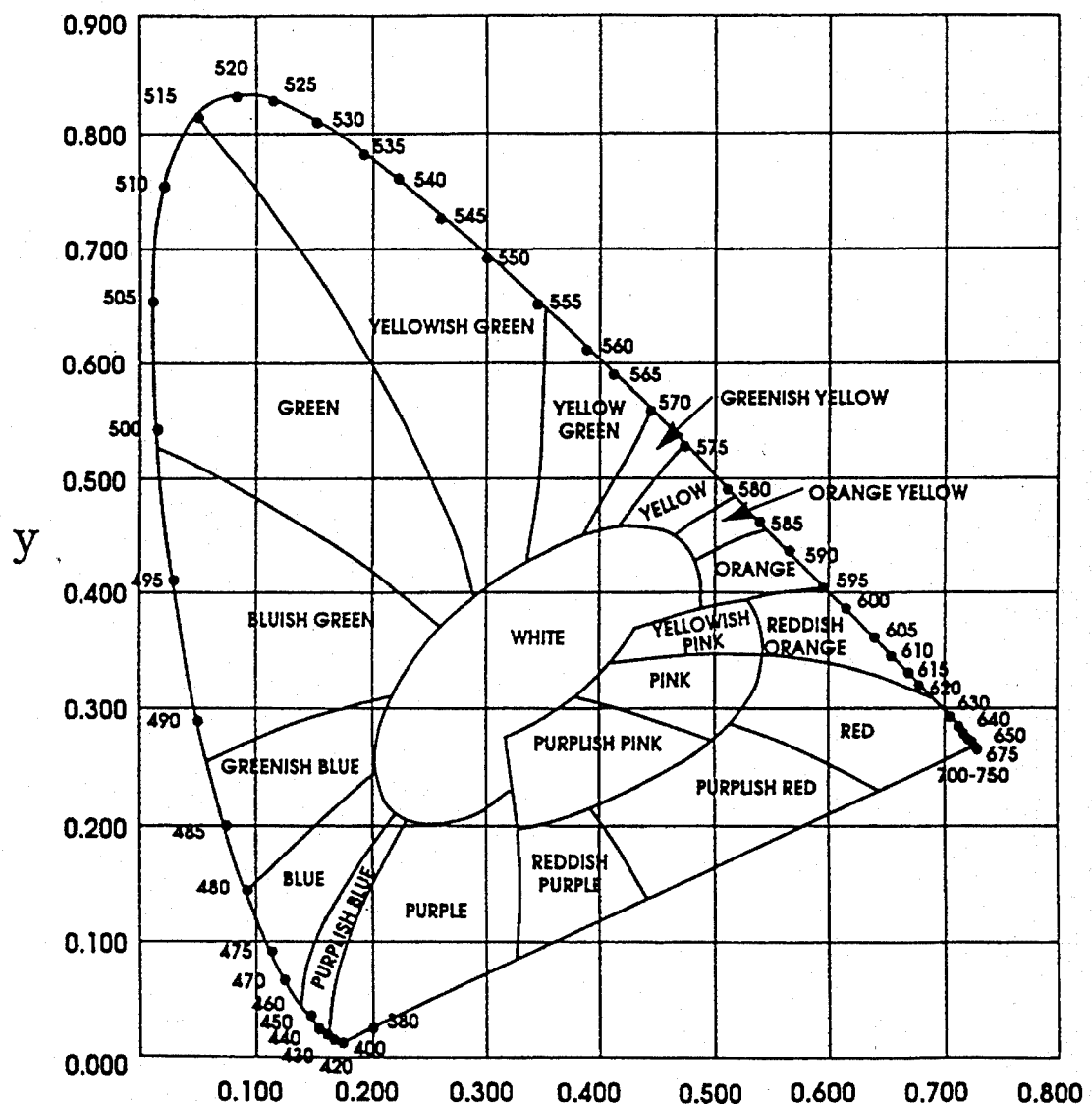
FIG. 10 is a two dimensional graph of CIE color nomenclature.
Figure 11:
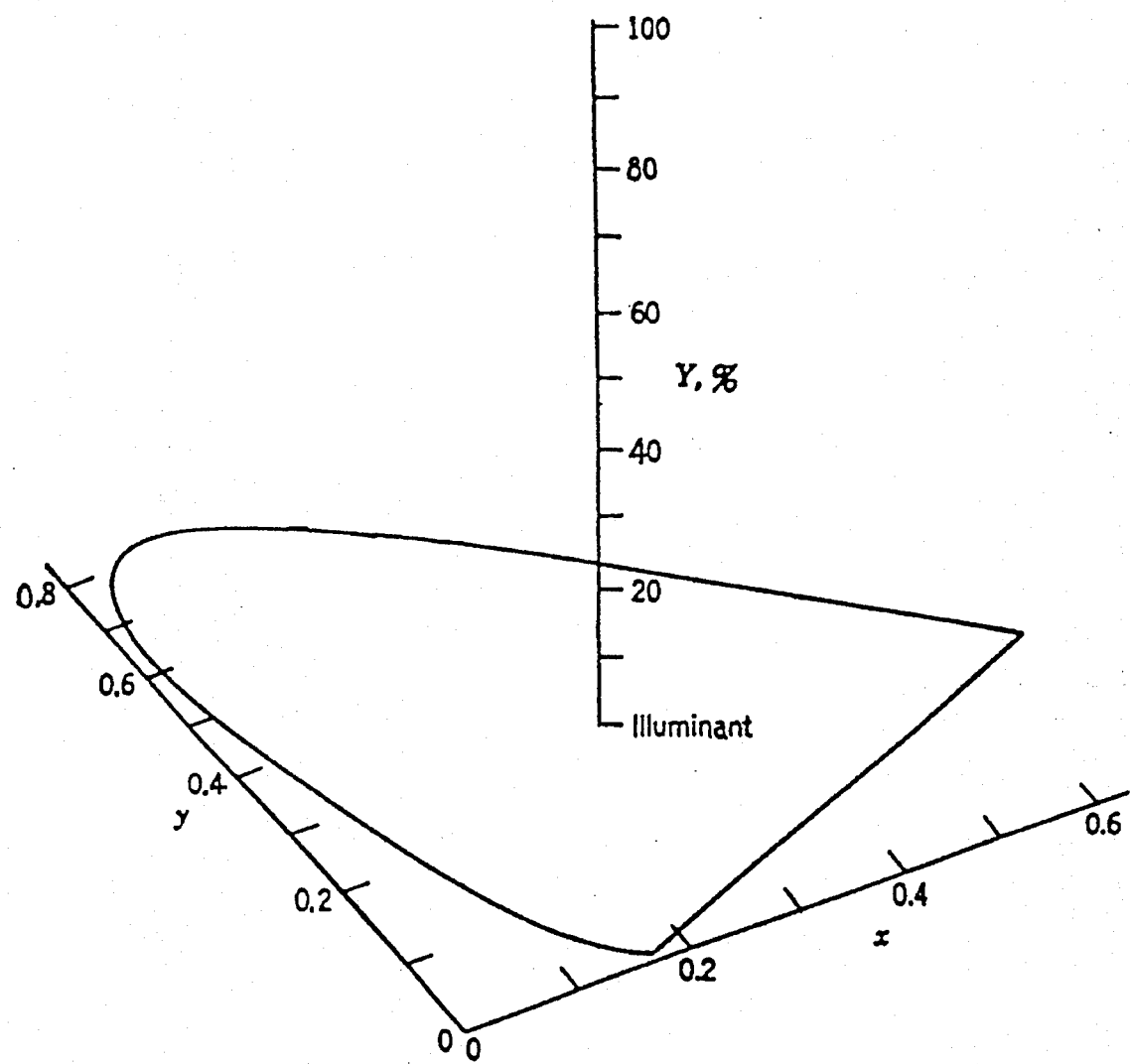
FIG. 11 is a three dimensional graph of CIE color nomenclature.

In prior art, a color camera was used to obtain the image and calculate the CIE values from the RGB (Red-Green-Blue) values provided by the camera. It was found that the information provided by an RGB system is limited in the color space it can define. FIG. 10 shows a two dimensional graph of the CIE color nomenclature. On this graph are plotted the 100 percent primary colors reading for the prior art color camera, including Red point 101 (x,y=0.735, 0.265), Green point 102(x,y=0.274,0.717), and Blue point 103 (x,y=0.167,0.090). The triangle 104 formed by these points defines the color space that the RGB camera can discern. There are many points within the CIE graph that lie outside this RGB triangle. These points can not be defined by an RGB system, and any color that lies outside this triangle, will be incorrectly described using a RGB camera. Therefore to accurately depict the CIE nomenclature, the complete spectral response is needed and provided by the data generated by the present inventors and particularly the preferred embodiment as described above.

In step 180, the calculations also include tone and saturation from the CIE system. Conversion to other internationally accept color systems can also be chosen by the operator. For example, the Munsell system, or the DIN 6164 can also be used.

In step 190, the values for the chosen numerical system is displayed on the video screen, along with the gemstone image, color graphs and spectral response curve of the selected area or gemstone. In step 200, the computer determines if all light positions have been captured, if not it returns to step 110 and repositions the light ring for the next run. If all positions are captured, the computer then constructs a composite image of the stone combining the results from all light positions. The system allows the user to select up to nine different light positions for analysis.

In step 210, the operator can obtain more detailed information for any section of the stone. The operator simply outlines the desired area with the mouse on the video screen, and the program then jumps back to step 150 and recalculates the information for the specified area. This process can be repeated for any of the images, at any light position.

In step 220, the information is printed out on a color printer at the operators request. The certificate is printed at a printer located away from and coupled to the device of the present invention.

APPENDIX A

Equations used in embodiment of present invention:

$R = \dfrac{\text{Light Intensity for specified area}}{\text{Incident Intensity of Light Source}}$ $P =$ Spectral Distribution for Given Light     (Specified in CIE Tables, See Reference)

$x', y', z', =$ Standard Observer Curves specified by CIE $$X = k \sum P R x'$$

$$Y = k \sum P R y' \quad \text{Where } k = 100 / \sum P \, y'$$

$$Z = k \sum P R z'$$

$x = X/(X+Y+Z) \qquad y = Y/(X+Y+Z) \qquad z = Z/(X+Y+Z)$

The equations for the L*a*b* representation of color used are:

$L^* = 116\,[\,f(Y/Y_n) - 16/116\,]$ $a^* = 500\,[\,f(X/X_n) - f(Y/Y_n)\,]$ $b^* = 200\,[\,f(Y/Y_n) - f(Z/Z_n)\,]$ where $f(Y/Y_n) = (Y/Y_n)^{1/3} \qquad Y/Y_n > 0.008856$ or $\quad f(Y/Y_n) = 7.787\,(Y/Y_n) + 16/116$ $f(X/X_n)$ and $f(Z/Z_n)$ are similarily defined $Y_n, X_n, Z_n$ are defined by Standard Observer and light choices found in CIE Tables.

TONE = (100-y)

Dominant wavelength (DWL)
- the wavelength of the spectrum color whose chromaticity is on the same straight line as the sample point and the illumination point SATURATION
- the distance from illuminant point to sample point, divided by that from illumant point to spectrum locus.

The equations used for construction of the image displayed on the RGB monitor in embodiment of present invention:

red = K1 * x + K2 *y + K3 *z green = K4 * x + K5 *y + K6 *z blue = K7 * x + K8 *y + K9 *z where K1-K9 are constants that depend on the tristimulus points used for the RGB triangle. These can be found in specifications for the display device, ie a graphics monitor.

```
//---------------------------------------------------------------
// Gem Vision - (C) Copyright 1995 by LambdaSpec Instruments
// TCapDlg
//--------------------------------------------------------------- include <owl\owlpch.h>
include <owl\dialog.h>
#include <owl\checkbox.h>
#include <owl\groupbox.h>
#include <owl\static.h>
#include <owl\edit.h>
#include <owl\button.h>
#include <owl\radiobut.h>
#include <owl\combobox.h>
#include <owl\mdi.h>
include <owl\statusba.h> include <stdio.h> include "mdifile.h"

include "TFiltDev.h"      // Filter System Control.
#include "TMotDev.h"       // Motion System Control.
#include "TUGTSCN.h"                        // UGTS Device Control.
#include "TImageDv.h"                       // Capture Device Control.

extern TStatusBar* sb;
extern int IsPoints[3][640][480];
extern int       ChamberTemp;

typedef struct
    {
    TMotionDevice* MotionDevice;
    TFilterDevice* FilterDevice;
    TUGTSDevice* UGTSContlr;
    TImageDevice* ImageDevice;
    } SystemDevices;

int LiveState;

//#include "TVision.h"                     // Vision Object.

#include "TStatDlg.h"                      // Stats dialog.

#include "TProcDlg.h"                      // Process a stone dialog.
//*****************************************************************************
//
// Creates Dialog box from rc file.
//
//*****************************************************************************
class TGVDialog : public TDialog
    {
    private:
        TButton*               QuitBtn;

TRadioButton*  DiffuseOnly;
        TRadioButton*  ReflectOnly;
        TRadioButton*  CurrentOnly;
```

```
//----------------------------------------------------------------
// Gem Vision - (C) Copyright 1995 by UGTS, Inc
// TCapDlg
//---------------------------------------------------------------- include <owl\owlpch.h>
include <owl\dialog.h>
#include <owl\checkbox.h>
#include <owl\groupbox.h>
#include <owl\static.h>
#include <owl\edit.h>
#include <owl\button.h>
#include <owl\radiobut.h>
#include <owl\combobox.h>
#include <owl\mdi.h>
include <owl\statusba.h> include <stdio.h> include "mdifile.h"

include "TFiltDev.h"      // Filter System Control.
#include "TMotDev.h"       // Motion System Control.
#include "TUGTSCN.h"       // UGTS Device Control.
#include "TImageDv.h"      // Capture Device Control.

extern TStatusBar* sb;
extern int IsPoints[3][640][480];
extern int      ChamberTemp;

typedef struct
        {
        TMotionDevice* MotionDevice;
        TFilterDevice* FilterDevice;
        TUGTSDevice* UGTSContlr;
        TImageDevice* ImageDevice;
        } SystemDevices;

int LiveState;

//#include "TVision.h"                    // Vision Object.

#include "TStatDlg.h"                    // Stats dialog.

#include "TProcDlg.h"                    // Process a stone dialog.

//*********************************************************************
//
// Creates Dialog box from rc file.
//
//*********************************************************************
class TGVDialog : public TDialog {
        private:
                TButton*                    QuitBtn;

TRadioButton*   DiffuseOnly;
                TRadioButton*   ReflectOnly;
                TRadioButton*   CurrentOnly;
```

```
void TGVDialog::EvMove(TPoint &clientOrigin)
        {

::SetWindowPos(HWindow,0,0,0,508,230,SWP_NOZORDER);

}

//******************************************************************
BOOL TGVDialog::EvEraseBkgnd(HDC painthdc)
        {
        RECT           fillRect;

fillRect.left = 0;
        fillRect.top = 0;
        fillRect.right = 550;
        fillRect.bottom = 550;

::FillRect(GetDC(HWindow),&fillRect,(HBRUSH) GetStockObject(LTGRAY_BRUSH));
        ::FillRect(GetDC(LightingGroup->HWindow),&fillRect,(HBRUSH) GetStockObject(LTGRAY_BRUSH));
        ::FillRect(GetDC(PauseSets->HWindow),&fillRect,(HBRUSH) GetStockObject(LTGRAY_BRUSH));
        return 0;

}

//---------------------------------------------------------------
// Gem Vision - (C) Copyright 1995 by UGTS, Inc
// TProcDlg
//--------------------------------------------------------------- include <owl\owlpch.h>
include <float.h>
#include <owl\dialog.h>
#include <owl\checkbox.h>
#include <owl\groupbox.h>
#include <owl\static.h>
#include <owl\edit.h>
#include <owl\button.h>
#include <owl\radiobut.h>
#include <owl\combobox.h>
#include <owl\mdi.h>
include <owl\statusba.h>
include <stdio.h>
#include <owl\point.h>
#include <owl\printer.h>
#include "math.h"

#include "mdifile.h"

include "TFiltDev.h"      // Filter System Control.
#include "TMotDev.h"            // Motion System Control.
#include "TUGTSCN.h"                   // UGTS Device Control.
#include "TImageDv.h"                  // Capture Device Control.

extern TStatusBar* sb;
extern TTextGadget*    FrameView;
extern TTextGadget*    CompletePercent;
//extern int IsPoints[3][640][480];
extern int     ChamberTemp;
extern int     UseLowWaveLengths;

typedef struct
        {
```

```
TRadioButton*    DoubleOnly;
TRadioButton*    CompleteAnalysis;
TRadioButton*    NinePosition;
TRadioButton*    SkipSet;
TRadioButton*    Set1;
TRadioButton*    Set2;
TRadioButton*    Set3;

TGroupBox*              CurrentGroup;
TGroupBox*              ViewGroup;
TGroupBox*              SepGroup;
TGroupBox*              LightingGroup;

TEdit*                          QuickPic;

TComboBox*       Manual1;
TComboBox*       Manual2;
TComboBox*       Manual3;
TComboBox*       WaveBox;
TComboBox*       PositionBox;

TStatic*         Static_Text1;
TStatic*         Static_Text2;
TStatic*         Static_Text3;
TStatic*         Static_Text4;
TStatic*         Static_Text5;
TStatic*         Static_Text6;
TStatic*         Static_Text7;
TStatic*         Static_Text8;
TStatic*         Static_Text9;
TStatic*         Static_Text10;

LPVOID                          hLiveMemAlloc;
LPVOID                          hLiveMemPtr;
LPVOID                          hLiveBmpPtr;
HANDLE                          hloc;
HDC                             winhdc;
HDC                             memhdc;
PBITMAPINFO  ptrPictureInfo;
HBITMAP                 PictureBmp;
HGDIOBJ                 hSelBmpObj;
int                                     BoxXOffset;
int                                     BoxYOffset;
int                                     BoxUprXPos;
int                                     BoxUprYPos;
int                                     BoxLowXPos;
int                                     BoxLowYPos;
UINT                    TimerState;
PAINTSTRUCT      ps;

TMDIClient*      Client;
HBRUSH                  backBlack;

SystemDevices* ptrSysDevs;

HBRUSH EvCtlColor(HDC, HWND hWndChild, UINT ctlType);

void DoCap();
void SetSet1();
void SetSet2();
void SetSet3();
void EnableManual();
```

```
            void DisableManual();
            void SetCurrentSets();
            void GetCurrentSets();
            void SetupWindow();
            void EvTimer(UINT timerId);
            void ExitMsg();
            void SetSepMsg();
            void CapMsg();
            void LiveMsg();
            void WaveProcess();
            void PosProcess();
            void WaveProcessEdit();
            void PosProcessEdit();

void StopLiveThread();
            void StartLiveThread();
            void DoLive();

DWORD                       dwThreadID;
            HANDLE                      hLiveThread;

public:
            TGVDialog::TGVDialog(TMDIClient* AParent, int dialogID, SystemDevices* ptrSysDevices
                                                         , TStatDialog* PStatDlg,
TApplication* PApp);
            ~TGVDialog();
            void RePaint();

TStatDialog*    PStatDialog;
            TProcDialog*    PProcDialog;
            int                         Cap_Flag;
            int                         CalState;
            TButton*        StartBtn;
            TButton*        StopBtn;
            TButton*        LiveBtn;
            TComboBox*      StoneBox;
            int                         CurLightPos;
            TApplication*   ptrMainApp;

BOOL CanClose();
            LRESULT NextCapMsg(WPARAM,LPARAM);
            LRESULT CloseProcMsg(WPARAM,LPARAM);
            friend DWORD FAR PASCAL LivehProc(TGVDialog*);
            void EvPaint();
            void EvMove(TPoint &clientOrigin);
            BOOL EvEraseBkgnd(HDC painthdc);

TEdit*          LowSep;
            TEdit*          HiSep;
            TEdit*          IDValue;
            TCheckBox*      ShowWaveBitmaps;
            TCheckBox*      EnableSep;
            TCheckBox*      FinalImage;
            TCheckBox*      PauseSets;

UINT            Set_Number;
            UINT            Set_States[3];
            FLOAT           Set_Manuals[3][3];

DECLARE_RESPONSE_TABLE(TGVDialog);

};
```

```
//****************************************************************************
DWORD FAR PASCAL LivehProc(TGVDialog*);

//****************************************************************************
DEFINE_RESPONSE_TABLE1(TGVDialog, TDialog)
    EV_WM_TIMER,
            EV_WM_CTLCOLOR,
    EV_COMMAND(IDC_QUIT, ExitMsg),
    EV_COMMAND(103, CapMsg),
    EV_COMMAND(IDC_SETSEP, SetSepMsg),
    EV_COMMAND(IDC_LIVEBTN, LiveMsg),
    EV_COMMAND(IDC_SET1, SetSet1),
    EV_COMMAND(IDC_SET2, SetSet2),
    EV_COMMAND(IDC_SET3, SetSet3),
    EV_COMMAND(IDC_CURPOS, EnableManual),
    EV_COMMAND(IDC_DIFFUSEONLY, DisableManual),
    EV_COMMAND(IDC_REFLECTONLY, DisableManual),
    EV_COMMAND(IDC_DOUBLEONLY, DisableManual),
    EV_COMMAND(IDC_COMPLETE, DisableManual),
    EV_COMMAND(IDC_NINEPOSITION, DisableManual),
    EV_COMMAND(IDC_SKIPSET, DisableManual),
    EV_CBN_EDITCHANGE(IDC_WAVELENGTHS, WaveProcessEdit),
    EV_CBN_EDITCHANGE(IDC_POSITIONS, PosProcessEdit),
    EV_CBN_SELCHANGE(IDC_WAVELENGTHS, WaveProcess),
    EV_CBN_SELCHANGE(IDC_POSITIONS, PosProcess),
    EV_MESSAGE(WM_USER+200, NextCapMsg),
    EV_MESSAGE(WM_USER+201,CloseProcMsg),
            EV_WM_PAINT,
            EV_WM_MOVE,
            EV_WM_ERASEBKGND,
END_RESPONSE_TABLE;

//****************************************************************************
TGVDialog::TGVDialog(TMDIClient* AParent, int dialogID, SystemDevices* ptrSysDevices, TStatDialog* PStatDlg,
TApplication* PApp) :TDialog(AParent,dialogID), TWindow(AParent)
        {
        DWORD                                     givemebytes;

ptrSysDevs = ptrSysDevices;
        Client = AParent;
        PStatDialog = PStatDlg;
        ptrMainApp = PApp;

LightingGroup = new TGroupBox(this, IDC_METERGROUP);
        ViewGroup = new TGroupBox(this, IDC_VIEWGROUP);
        SepGroup = new TGroupBox(this, IDC_SEPGROUP);
        CurrentGroup = new TGroupBox(this, IDC_CURGROUP);
        ShowWaveBitmaps = new TCheckBox(this, IDC_SHOWWAVEBITMAPS);
        EnableSep = new TCheckBox(this, IDC_SETSEP);
        PauseSets = new TCheckBox(this, IDC_PAUSESETS);
        DiffuseOnly = new TRadioButton(this, IDC_DIFFUSEONLY,LightingGroup);
        ReflectOnly = new TRadioButton(this, IDC_REFLECTONLY,LightingGroup);
        CurrentOnly = new TRadioButton(this, IDC_CURPOS,LightingGroup);
        DoubleOnly = new TRadioButton(this, IDC_DOUBLEONLY,LightingGroup);
        CompleteAnalysis = new TRadioButton(this, IDC_COMPLETE,LightingGroup);
        NinePosition = new TRadioButton(this, IDC_NINEPOSITION,LightingGroup);
        SkipSet = new TRadioButton(this, IDC_SKIPSET,LightingGroup);
        Set1 = new TRadioButton(this, IDC_SET1,CurrentGroup);
        Set2 = new TRadioButton(this, IDC_SET2,CurrentGroup);
        Set3 = new TRadioButton(this, IDC_SET3,CurrentGroup);
```

```
        QuitBtn = new TRadioButton(this, IDC_QUIT);
        FinalImage = new TCheckBox(this, IDC_FINALIMAGE);
        QuickPic = new TEdit(this, IDC_QUICKPIC);

LowSep = new TEdit(this, IDC_SEPLOWVALUE);
        HiSep = new TEdit(this, IDC_SEPHIVALUE);
        IDValue = new TEdit(this, IDC_IDVALUE);
        StartBtn = new TButton(this, IDC_STARTBTN);
        StopBtn = new TButton(this, IDC_STOPBTN);
        LiveBtn = new TButton(this, IDC_LIVEBTN);

StoneBox = new TComboBox(this, IDC_STONEBOX);
        Manual1 = new TComboBox(this, IDC_MANUAL1);
        Manual2 = new TComboBox(this, IDC_MANUAL2);
        Manual3 = new TComboBox(this, IDC_MANUAL3);
        WaveBox = new TComboBox(this, IDC_WAVELENGTHS);
        PositionBox = new TComboBox(this, IDC_POSITIONS);
        Static_Text1 = new TStatic(this, IDC_TEXT1);
        Static_Text2 = new TStatic(this, IDC_TEXT2);
        Static_Text3 = new TStatic(this, IDC_TEXT3);
        Static_Text4 = new TStatic(this, IDC_TEXT4);
        Static_Text5 = new TStatic(this, IDC_TEXT5);
        Static_Text6 = new TStatic(this, IDC_TEXT6);
        Static_Text7 = new TStatic(this, IDC_TEXT7);
        Static_Text8 = new TStatic(this, IDC_TEXT8);
        Static_Text9 = new TStatic(this, IDC_TEXT9);
        Static_Text10 = new TStatic(this, IDC_TEXT10);

backBlack = CreateSolidBrush(RGB(0,0,0));

CurLightPos = 1;
        PStatDialog->LightPosition->SetText("Reflect");

CalState = 0;

BoxYOffset = ptrSysDevs->ImageDevice->BoxYOffset;  // see timagedev constructor for values!
        BoxXOffset = ptrSysDevs->ImageDevice->BoxXOffset;
        BoxUprXPos = ptrSysDevs->ImageDevice->BoxUprXPos;
        BoxUprYPos = ptrSysDevs->ImageDevice->BoxUprYPos;
        BoxLowXPos = ptrSysDevs->ImageDevice->BoxLowXPos;
        BoxLowYPos = ptrSysDevs->ImageDevice->BoxLowYPos;

// Allocate Virtual memory for bitmap and tranfering live frame
        givemebytes = (640 * 480) + (640 * 480 * 3);
        hLiveMemAlloc = VirtualAlloc((LPVOID) NULL, givemebytes, MEM_RESERVE, PAGE_READWRITE);
        if (hLiveMemAlloc == NULL)
                {
        ::MessageBox( HWindow,"Unable to allocate live box memory.","System Error." ,
                MB_ICONEXCLAMATION | MB_OK );
                        return;
                }

// Commit memory for image
        givemebytes = 640 * 480;
        hLiveMemPtr = VirtualAlloc(hLiveMemAlloc, givemebytes, MEM_COMMIT, PAGE_READWRITE);
        if (hLiveMemPtr == NULL)
                {
        ::MessageBox( HWindow,"Unable to commit Live Image memory.","System Error." ,
                MB_ICONEXCLAMATION | MB_OK );
                        return;
                }
```

```
// Commit memory for bitmap
        hLiveMemAlloc = (LPVOID) ((DWORD) hLiveMemAlloc + givemebytes);
        givemebytes = 168 * 168 * 3;
        hLiveBmpPtr = VirtualAlloc(hLiveMemAlloc, givemebytes, MEM_COMMIT, PAGE_READWRITE);
        if (hLiveBmpPtr == NULL)
            {
    ::MessageBox( HWindow,"Unable to commit Live Bitmap memory.","System Error." ,
            MB_ICONEXCLAMATION | MB_OK ) ;
                return;
                }

Set_Number = 0;
        Set_States[0] = 2;
        Set_States[1] = 6;
        Set_States[2] = 6;
        Set_Manuals[0][0] = 0;
        Set_Manuals[0][1] = 0;
        Set_Manuals[0][2] = 0;
        Set_Manuals[1][0] = 0;
        Set_Manuals[1][1] = 0;
        Set_Manuals[1][2] = 0;
        Set_Manuals[2][0] = 0;
        Set_Manuals[2][1] = 0;
        Set_Manuals[2][2] = 0;

LiveState = 0;
        };

//*****************************************************************************
TGVDialog::~TGVDialog()
        { if (hLiveMemAlloc != NULL)
                {
                VirtualFree(hLiveMemAlloc, 0, MEM_RELEASE);
                }

}

//*****************************************************************************
//
// Button - Cancel.
//
//*****************************************************************************
void TGVDialog::ExitMsg()

{

DWORD   exitCode;
        BOOL    thReturn;
        ULONG   waitcntr = 0;

StopBtn->EnableWindow(0);

if (TimerState == 1)
                {
                StopLiveThread();
                QuickPic->Show(SW_HIDE);
                WaveBox->Show(SW_HIDE);
                PositionBox->Show(SW_HIDE);
                PauseSets->Show(SW_HIDE);
                Static_Text7->Show(SW_HIDE);
```

```
            Static_Text8->Show(SW_HIDE);
            Static_Text9->Show(SW_HIDE);
            Static_Text10->Show(SW_HIDE);
            TimerState = 0;

LiveBtn->Show(SW_HIDE);
            QuitBtn->Show(SW_SHOWNORMAL);

//          ::InvalidateRect(this->HWindow,NULL,TRUE);

ShowWaveBitmaps->Show(SW_SHOWNORMAL);
            DiffuseOnly->Show(SW_SHOWNORMAL);
            ReflectOnly->Show(SW_SHOWNORMAL);
            CurrentOnly->Show(SW_SHOWNORMAL);
            NinePosition->Show(SW_SHOWNORMAL);
            SkipSet->Show(SW_SHOWNORMAL);
            DoubleOnly->Show(SW_SHOWNORMAL);
            FinalImage->Show(SW_SHOWNORMAL);
            Set1->Show(SW_SHOWNORMAL);
            Set2->Show(SW_SHOWNORMAL);
            Set3->Show(SW_SHOWNORMAL);
            EnableSep->Show(SW_SHOWNORMAL);
            CompleteAnalysis->Show(SW_SHOWNORMAL);
            Static_Text1->Show(SW_SHOWNORMAL);
            Static_Text2->Show(SW_SHOWNORMAL);
            Static_Text3->Show(SW_SHOWNORMAL);
            Static_Text4->Show(SW_SHOWNORMAL);
            Static_Text5->Show(SW_SHOWNORMAL);
            Static_Text6->Show(SW_SHOWNORMAL);
            Manual1->Show(SW_SHOWNORMAL);
/           Manual2->Show(SW_SHOWNORMAL);
            Manual3->Show(SW_SHOWNORMAL);
            LowSep->Show(SW_SHOWNORMAL);
            HiSep->Show(SW_SHOWNORMAL);
            StoneBox->Show(SW_SHOWNORMAL);
            IDValue->Show(SW_SHOWNORMAL);

LightingGroup->Show(SW_SHOWNORMAL);
            LightingGroup->Show(SW_HIDE);
            LightingGroup->Show(SW_SHOWNORMAL);

ViewGroup->Show(SW_SHOWNORMAL);
            SepGroup->Show(SW_SHOWNORMAL);
            CurrentGroup->Show(SW_SHOWNORMAL);
            }
     else
            {
            ::PostMessage(PProcDialog->HWindow,WM_USER + 226,12,12);
            sb->SetText("Process Being Cancelled!");

ptrMainApp->EnableCtl3dAutosubclass(TRUE);
            PProcDialog->ShowWindow(SW_HIDE);
            ptrMainApp->EnableCtl3dAutosubclass(FALSE);
            }

ReflectOnly->EnableWindow(1);
     DiffuseOnly->EnableWindow(1);
     DoubleOnly->EnableWindow(1);
     CurrentOnly->EnableWindow(1);
     NinePosition->EnableWindow(1);
     SkipSet->EnableWindow(1);
     CompleteAnalysis->EnableWindow(1);
```

```
StoneBox->EnableWindow(1);
FinalImage->EnableWindow(1);
EnableSep->EnableWindow(1);
Set1->EnableWindow(1);
Set2->EnableWindow(1);
Set3->EnableWindow(1);
IDValue->EnableWindow(1);

if (CurrentOnly->GetCheck() == 1)
        {
        Manual1->EnableWindow(1);
        Manual2->EnableWindow(1);
        Manual3->EnableWindow(1);
        } if (EnableSep->GetCheck() == 1)
        {
        LowSep->EnableWindow(1);
        HiSep->EnableWindow(1);
        }

CurLightPos = 1;
PStatDialog->LightPosition->SetText("Reflect");
ptrSysDevs->MotionDevice->Home();

Cap_Flag = 0;

StartBtn->EnableWindow(1);
StartBtn->Show(SW_SHOWNORMAL);

UpdateWindow();

}
//****************************************************************
//
// Button - Enable Separation.
//
//****************************************************************
void TGVDialog::SetSepMsg()

{ if (EnableSep->GetCheck() == 1)
                {
                EnableSep->Uncheck();
                LowSep->EnableWindow(0);
                HiSep->EnableWindow(0);
                }
        else
                {
                EnableSep->Check();
                LowSep->EnableWindow(1);
                HiSep->EnableWindow(1);
                }

}
//****************************************************************
//
// Button - Continue / Stop Live box display.
//
```

```
//****************************************************************************
void TGVDialog::LiveMsg()

{ if (TimerState == 1)
                {
                StopLiveThread();
                QuickPic->Show(SW_HIDE);
                WaveBox->Show(SW_HIDE);
                PositionBox->Show(SW_HIDE);
                PauseSets->Show(SW_HIDE);
                Static_Text7->Show(SW_HIDE);
                Static_Text8->Show(SW_HIDE);
                Static_Text9->Show(SW_HIDE);
                Static_Text10->Show(SW_HIDE);
                UpdateWindow();
                TimerState = 0;

DoCap();

}
        else
                {
                QuickPic->Show(SW_SHOWNORMAL);
                WaveBox->Show(SW_SHOWNORMAL);
                PositionBox->Show(SW_SHOWNORMAL);
                PauseSets->Show(SW_SHOWNORMAL);
                Static_Text7->Show(SW_SHOWNORMAL);
                Static_Text8->Show(SW_SHOWNORMAL);
                Static_Text9->Show(SW_SHOWNORMAL);
                Static_Text10->Show(SW_SHOWNORMAL);
                TimerState = 1;
                StopBtn->EnableWindow(1);
                LiveState = 1;
                UpdateWindow();
                StartLiveThread();
                TimerState = 1;
                }

}

//****************************************************************************
//
// Button - Start.
//
//****************************************************************************
void TGVDialog::CapMsg()

{
        char StoneText[100];
        LPSTR ptrStoneText = StoneText;

StoneBox->GetText(ptrStoneText,100);
        if (strcmpi(ptrStoneText,"") == 0)
                {
        ::MessageBox( HWindow,"Please select a stone type first.","User Error." ,
                MB_ICONEXCLAMATION | MB_OK );
                return;
                }
```

```
        CalState = 0;

if (strcmpi(ptrStoneText,"xxLightCalibration") == 0)
            {
            CalState = 1;
            } if (strcmpi(ptrStoneText,"xxBackCalibration") == 0)
            {
            CalState = 2;
            }

StartBtn->Show(SW_HIDE);
    LiveBtn->Show(SW_SHOWNORMAL);
    StopBtn->Show(SW_SHOWNORMAL);

LightingGroup->Show(SW_HIDE);
    ViewGroup->Show(SW_HIDE);
    SepGroup->Show(SW_HIDE);
    CurrentGroup->Show(SW_HIDE);
    ShowWaveBitmaps->Show(SW_HIDE);
    DiffuseOnly->Show(SW_HIDE);
    ReflectOnly->Show(SW_HIDE);
    CurrentOnly->Show(SW_HIDE);
    NinePosition->Show(SW_HIDE);
    SkipSet->Show(SW_HIDE);
    DoubleOnly->Show(SW_HIDE);
    FinalImage->Show(SW_HIDE);
    Set1->Show(SW_HIDE);
    Set2->Show(SW_HIDE);
    Set3->Show(SW_HIDE);
    EnableSep->Show(SW_HIDE);
    CompleteAnalysis->Show(SW_HIDE);
    Static_Text1->Show(SW_HIDE);
    Static_Text2->Show(SW_HIDE);
    Static_Text3->Show(SW_HIDE);
    Static_Text4->Show(SW_HIDE);
    Static_Text5->Show(SW_HIDE);
    Static_Text6->Show(SW_HIDE);
    Manual1->Show(SW_HIDE);
    Manual2->Show(SW_HIDE);
    Manual3->Show(SW_HIDE);
    LowSep->Show(SW_HIDE);
    HiSep->Show(SW_HIDE);
    StoneBox->Show(SW_HIDE);
    IDValue->Show(SW_HIDE);

LiveMsg();

ptrSysDevs->MotionDevice->moMovementStep = 5;
    ptrSysDevs->MotionDevice->Move();
    CurLightPos = 2;
    ptrSysDevs->FilterDevice->SetWave(700);
    WaveBox->SetSelString("700",0);
    PStatDialog->LightPosition->SetText("Suffuse");
    PositionBox->SetSelString("Suffuse",0);

}

//**************************************************************************
//
// Close out Cap Window.
```

```
//
//*******************************************************************
BOOL TGVDialog::CanClose()

{ return 1;

};

//*******************************************************************
//
// Setup Dialog.
//
//*******************************************************************
void TGVDialog::SetupWindow()

{
    char mbuf[10];

TDialog::SetupWindow();

Cap_Flag = 0;

if (EnableSep->GetCheck() != 1)
        {
        LowSep->EnableWindow(0);
        HiSep->EnableWindow(0);
        }

StoneBox->AddString("Ruby");
    StoneBox->AddString("Blue Sapphire");
    StoneBox->AddString("Pink Tourmaline");
    StoneBox->AddString("Emerald");
    StoneBox->AddString("Aquamarine");
    StoneBox->AddString("Topaz");
    StoneBox->AddString("Pink Sapphire");
    StoneBox->AddString("xxLightCalibration");
    StoneBox->AddString("xxBackCalibration");
    StoneBox->AddString("xxControl");
    StoneBox->AddString("Unknown");

Manual1->AddString("0.0");
    Manual1->AddString("Reflect");
    Manual1->AddString("0.1");
    Manual1->AddString("0.2");
    Manual1->AddString("0.3");
    Manual1->AddString("0.4");
    Manual1->AddString("0.5");
    Manual1->AddString("0.6");
    Manual1->AddString("0.7");
    Manual1->AddString("0.8");
    Manual1->AddString("0.9");
    Manual1->AddString("1.0");
    Manual1->AddString("1.1");
    Manual1->AddString("1.2");
    Manual1->AddString("1.3");
    Manual1->AddString("1.4");
    Manual1->AddString("1.5");
    Manual1->AddString("1.6");
    Manual1->AddString("1.7");
```

```
Manual1->AddString("1.8");
Manual1->AddString("1.9");
Manual1->AddString("2.0");
Manual1->AddString("2.1");
Manual1->AddString("2.2");
Manual1->AddString("2.3");
Manual1->AddString("2.4");
Manual1->AddString("2.5");
Manual1->AddString("2.6");
Manual1->AddString("2.7");
Manual1->AddString("2.8");
Manual1->AddString("2.9");
Manual1->AddString("3.0");
Manual1->AddString("3.1");
Manual1->AddString("3.2");
Manual1->AddString("3.3");
Manual1->AddString("3.4");
Manual1->AddString("3.5");
Manual1->AddString("3.6");
Manual1->AddString("3.7");
Manual1->AddString("3.8");
Manual1->AddString("3.9");
Manual1->AddString("4.0");
Manual1->AddString("4.1");
Manual1->AddString("4.2");
Manual1->AddString("4.3");
Manual1->AddString("Suffuse");
Manual1->AddString("4.4");
Manual1->AddString("4.5");
Manual1->AddString("4.6");
Manual1->AddString("4.7");
Manual1->AddString("4.8");
Manual1->AddString("4.9");
Manual1->AddString("5.0");
Manual1->AddString("5.1");
Manual1->AddString("5.2");
Manual1->AddString("5.3");
Manual1->AddString("Diffuse");
Manual1->AddString("5.4");
Manual1->AddString("5.5");
Manual1->AddString("5.6");
Manual1->AddString("5.7");
Manual1->AddString("5.8");
Manual1->AddString("5.9");
Manual1->AddString("6.0");

Manual2->AddString("0.0");
Manual2->AddString("Reflect");
Manual2->AddString("0.1");
Manual2->AddString("0.2");
Manual2->AddString("0.3");
Manual2->AddString("0.4");
Manual2->AddString("0.5");
Manual2->AddString("0.6");
Manual2->AddString("0.7");
Manual2->AddString("0.8");
Manual2->AddString("0.9");
Manual2->AddString("1.0");
Manual2->AddString("1.1");
Manual2->AddString("1.2");
Manual2->AddString("1.3");
Manual2->AddString("1.4");
```

```
Manual2->AddString("1.5");
Manual2->AddString("1.6");
Manual2->AddString("1.7");
Manual2->AddString("1.8");
Manual2->AddString("1.9");
Manual2->AddString("2.0");
Manual2->AddString("2.1");
Manual2->AddString("2.2");
Manual2->AddString("2.3");
Manual2->AddString("2.4");
Manual2->AddString("2.5");
Manual2->AddString("2.6");
Manual2->AddString("2.7");
Manual2->AddString("2.8");
Manual2->AddString("2.9");
Manual2->AddString("3.0");
Manual2->AddString("3.1");
Manual2->AddString("3.2");
Manual2->AddString("3.3");
Manual2->AddString("3.4");
Manual2->AddString("3.5");
Manual2->AddString("3.6");
Manual2->AddString("3.7");
Manual2->AddString("3.8");
Manual2->AddString("3.9");
Manual2->AddString("4.0");
Manual2->AddString("4.1");
Manual2->AddString("4.2");
Manual2->AddString("4.3");
Manual2->AddString("Suffuse");
Manual2->AddString("4.4");
Manual2->AddString("4.5");
Manual2->AddString("4.6");
Manual2->AddString("4.7");
Manual2->AddString("4.8");
Manual2->AddString("4.9");
Manual2->AddString("5.0");
Manual2->AddString("5.1");
Manual2->AddString("5.2");
Manual2->AddString("5.3");
Manual2->AddString("Diffuse");
Manual2->AddString("5.4");
Manual2->AddString("5.5");
Manual2->AddString("5.6");
Manual2->AddString("5.7");
Manual2->AddString("5.8");
Manual2->AddString("5.9");
Manual2->AddString("6.0");

Manual3->AddString("0.0");
Manual3->AddString("Reflect");
Manual3->AddString("0.1");
Manual3->AddString("0.2");
Manual3->AddString("0.3");
Manual3->AddString("0.4");
Manual3->AddString("0.5");
Manual3->AddString("0.6");
Manual3->AddString("0.7");
Manual3->AddString("0.8");
Manual3->AddString("0.9");
Manual3->AddString("1.0");
Manual3->AddString("1.1");
```

```
Manual3->AddString("1.2");
Manual3->AddString("1.3");
Manual3->AddString("1.4");
Manual3->AddString("1.5");
Manual3->AddString("1.6");
Manual3->AddString("1.7");
Manual3->AddString("1.8");
Manual3->AddString("1.9");
Manual3->AddString("2.0");
Manual3->AddString("2.1");
Manual3->AddString("2.2");
Manual3->AddString("2.3");
Manual3->AddString("2.4");
Manual3->AddString("2.5");
Manual3->AddString("2.6");
Manual3->AddString("2.7");
Manual3->AddString("2.8");
Manual3->AddString("2.9");
Manual3->AddString("3.0");
Manual3->AddString("3.1");
Manual3->AddString("3.2");
Manual3->AddString("3.3");
Manual3->AddString("3.4");
Manual3->AddString("3.5");
Manual3->AddString("3.6");
Manual3->AddString("3.7");
Manual3->AddString("3.8");
Manual3->AddString("3.9");
Manual3->AddString("4.0");
Manual3->AddString("4.1");
Manual3->AddString("4.2");
Manual3->AddString("4.3");
Manual3->AddString("Suffuse");
Manual3->AddString("4.4");
Manual3->AddString("4.5");
Manual3->AddString("4.6");
Manual3->AddString("4.7");
Manual3->AddString("4.8");
Manual3->AddString("4.9");
Manual3->AddString("5.0");
Manual3->AddString("5.1");
Manual3->AddString("5.2");
Manual3->AddString("5.3");
Manual3->AddString("Diffuse");
Manual3->AddString("5.4");
Manual3->AddString("5.5");
Manual3->AddString("5.6");
Manual3->AddString("5.7");
Manual3->AddString("5.8");
Manual3->AddString("5.9");
Manual3->AddString("6.0");

PositionBox->AddString("0.0");
PositionBox->AddString("Reflect");
PositionBox->AddString("0.1");
PositionBox->AddString("0.2");
PositionBox->AddString("0.3");
PositionBox->AddString("0.4");
PositionBox->AddString("0.5");
PositionBox->AddString("0.6");
PositionBox->AddString("0.7");
PositionBox->AddString("0.8");
```

```
PositionBox->AddString("0.9");
PositionBox->AddString("1.0");
PositionBox->AddString("1.1");
PositionBox->AddString("1.2");
PositionBox->AddString("1.3");
PositionBox->AddString("1.4");
PositionBox->AddString("1.5");
PositionBox->AddString("1.6");
PositionBox->AddString("1.7");
PositionBox->AddString("1.8");
PositionBox->AddString("1.9");
PositionBox->AddString("2.0");
PositionBox->AddString("2.1");
PositionBox->AddString("2.2");
PositionBox->AddString("2.3");
PositionBox->AddString("2.4");
PositionBox->AddString("2.5");
PositionBox->AddString("2.6");
PositionBox->AddString("2.7");
PositionBox->AddString("2.8");
PositionBox->AddString("2.9");
PositionBox->AddString("3.0");
PositionBox->AddString("3.1");
PositionBox->AddString("3.2");
PositionBox->AddString("3.3");
PositionBox->AddString("3.4");
PositionBox->AddString("3.5");
PositionBox->AddString("3.6");
PositionBox->AddString("3.7");
PositionBox->AddString("3.8");
PositionBox->AddString("3.9");
PositionBox->AddString("4.0");
PositionBox->AddString("4.1");
PositionBox->AddString("4.2");
PositionBox->AddString("4.3");
PositionBox->AddString("Suffuse");
PositionBox->AddString("4.4");
PositionBox->AddString("4.5");
PositionBox->AddString("4.6");
PositionBox->AddString("4.7");
PositionBox->AddString("4.8");
PositionBox->AddString("4.9");
PositionBox->AddString("5.0");
PositionBox->AddString("5.1");
PositionBox->AddString("5.2");
PositionBox->AddString("5.3");
PositionBox->AddString("Diffuse");
PositionBox->AddString("5.4");
PositionBox->AddString("5.5");
PositionBox->AddString("5.6");
PositionBox->AddString("5.7");
PositionBox->AddString("5.8");
PositionBox->AddString("5.9");
PositionBox->AddString("6.0");

WaveBox->AddString("400");
WaveBox->AddString("410");
WaveBox->AddString("420");
WaveBox->AddString("430");
WaveBox->AddString("440");
WaveBox->AddString("450");
WaveBox->AddString("460");
```

```
WaveBox->AddString("470");
WaveBox->AddString("480");
WaveBox->AddString("490");
WaveBox->AddString("500");
WaveBox->AddString("510");
WaveBox->AddString("520");
WaveBox->AddString("530");
WaveBox->AddString("540");
WaveBox->AddString("550");
WaveBox->AddString("560");
WaveBox->AddString("570");
WaveBox->AddString("580");
WaveBox->AddString("590");
WaveBox->AddString("600");
WaveBox->AddString("610");
WaveBox->AddString("620");
WaveBox->AddString("630");
WaveBox->AddString("640");
WaveBox->AddString("650");
WaveBox->AddString("660");
WaveBox->AddString("670");
WaveBox->AddString("680");
WaveBox->AddString("690");
WaveBox->AddString("700");

ReflectOnly->Check();
FinalImage->Check();
ShowWaveBitmaps->Check();

ChamberTemp = ptrSysDevs->UGTSContlr->ReadTemp();
sprintf(mbuf,"%d",ChamberTemp);
PStatDialog->Temperature->SetText(mbuf);

IDValue->SetText("Testing");

HiSep->SetText("65");
LowSep->SetText("65");

PStatDialog->WaveLength->SetText("--");
PStatDialog->LightPosition->SetText("Reflect");

// set up live bitmap winhdc = GetDC(QuickPic->HWindow);
    memhdc = CreateCompatibleDC(NULL);

hloc = LocalAlloc(LMEM_ZEROINIT | LMEM_MOVEABLE, sizeof(BITMAPINFOHEADER));
    ptrPictureInfo = (PBITMAPINFO) LocalLock(hloc);

if (ptrPictureInfo == NULL)
        {
    ::MessageBox( HWindow,"Unable to commit local memory.","System Error." ,
            MB_ICONEXCLAMATION | MB_OK ) ;
            return;
        } ptrPictureInfo->bmiHeader.biSize = sizeof(BITMAPINFOHEADER);
    ptrPictureInfo->bmiHeader.biWidth = 168;
    ptrPictureInfo->bmiHeader.biHeight = 168;
    ptrPictureInfo->bmiHeader.biPlanes = 1;
    ptrPictureInfo->bmiHeader.biBitCount = 24;
    ptrPictureInfo->bmiHeader.biCompression = BI_RGB;
```

```
        ptrPictureInfo->bmiHeader.biSizeImage = 0;
        ptrPictureInfo->bmiHeader.biXPelsPerMeter = 0;
        ptrPictureInfo->bmiHeader.biYPelsPerMeter = 0;
        ptrPictureInfo->bmiHeader.biClrUsed = 0;
        ptrPictureInfo->bmiHeader.biClrImportant = 0;

PictureBmp = CreateDIBitmap(memhdc,(BITMAPINFOHEADER FAR*) ptrPictureInfo, CBM_CREATEDIB,
hLiveBmpPtr, ptrPictureInfo, 0);
//      PictureBmp = CreateDIBitmap(memhdc,(BITMAPINFOHEADER FAR*) NULL, CBM_CREATEDIB, hLiveBmpPtr,
ptrPictureInfo, 0);

if (PictureBmp == NULL)
                {
    ::MessageBox( HWindow,"Unable to create DIBitmap.","System Error." ,
                MB_ICONEXCLAMATION | MB_OK ) ;
                return;
                } hSelBmpObj = SelectObject(memhdc,PictureBmp);

ptrSysDevs->FilterDevice->SetWave(700);
        WaveBox->SetSelString("700",0);
        StoneBox->SetSelString("Unknown",0);
        PositionBox->SetSelString("0.0",0);

TimerState = 0;

SetCurrentSets();

};

//***************************************************************************
//
// Paint Dialog.
//
//***************************************************************************
void TGVDialog::RePaint()
        {

/*
        if (TimerState == 0)
                {
                LightingGroup->Show(SW_HIDE);
                ViewGroup->Show(SW_HIDE);
                SepGroup->Show(SW_HIDE);
                CurrentGroup->Show(SW_HIDE);

NinePosition->Show(SW_HIDE);
                NinePosition->Show(SW_SHOWNORMAL);

SkipSet->Show(SW_HIDE);
                SkipSet->Show(SW_SHOWNORMAL);

ShowWaveBitmaps->Show(SW_HIDE);
                ShowWaveBitmaps->Show(SW_SHOWNORMAL);

DiffuseOnly->Show(SW_HIDE);
                DiffuseOnly->Show(SW_SHOWNORMAL);

ReflectOnly->Show(SW_HIDE);
                ReflectOnly->Show(SW_SHOWNORMAL);
```

```
                CurrentOnly->Show(SW_HIDE);
                CurrentOnly->Show(SW_SHOWNORMAL);

DoubleOnly->Show(SW_HIDE);
                DoubleOnly->Show(SW_SHOWNORMAL);

FinalImage->Show(SW_HIDE);
                FinalImage->Show(SW_SHOWNORMAL);

Set1->Show(SW_HIDE);
                Set1->Show(SW_SHOWNORMAL);

Set2->Show(SW_HIDE);
                Set2->Show(SW_SHOWNORMAL);

Set3->Show(SW_HIDE);
                Set3->Show(SW_SHOWNORMAL);

EnableSep->Show(SW_HIDE);
                EnableSep->Show(SW_SHOWNORMAL);

CompleteAnalysis->Show(SW_HIDE);
                CompleteAnalysis->Show(SW_SHOWNORMAL);

CurrentGroup->Show(SW_SHOWNORMAL);
                LightingGroup->Show(SW_SHOWNORMAL);
                ViewGroup->Show(SW_SHOWNORMAL);
                SepGroup->Show(SW_SHOWNORMAL);

if (PProcDialog != NULL) PProcDialog->RePaint();
                }
        else
                {
                PauseSets->Show(SW_HIDE);
                PauseSets->Show(SW_SHOWNORMAL);

WaveBox->Show(SW_HIDE);
                WaveBox->Show(SW_SHOWNORMAL);

PositionBox->Show(SW_HIDE);
                PositionBox->Show(SW_SHOWNORMAL);
                }
*/
        };

//****************************************************************************
//
//
//****************************************************************************
HBRUSH  TGVDialog::EvCtlColor(HDC hdc, HWND hWndChild, UINT ctlType)
        { int ResID;

ResID = ::GetDlgCtrlID(hWndChild);

if ((ResID == IDC_WAVELENGTHS) || (ResID == IDC_POSITIONS) || (ResID == IDC_QUICKPIC))
                {
                ::SetTextColor(hdc,RGB(0,255,0));
                ::SetBkColor(hdc,RGB(0,0,0));
                return backBlack;
```

```
            } return FALSE;

};

//**************************************************************************
LRESULT TGVDialog::NextCapMsg(WPARAM,LPARAM)
    {

StopBtn->EnableWindow(0);
        StartBtn->EnableWindow(1);
        ReflectOnly->EnableWindow(1);
        DiffuseOnly->EnableWindow(1);
        CurrentOnly->EnableWindow(1);
        CompleteAnalysis->EnableWindow(1);
        DoubleOnly->EnableWindow(1);
        NinePosition->EnableWindow(1);
        SkipSet->EnableWindow(1);
        StoneBox->EnableWindow(1);
        FinalImage->EnableWindow(1);
        EnableSep->EnableWindow(1);
        Set1->EnableWindow(1);
        Set2->EnableWindow(1);
        Set3->EnableWindow(1);
        IDValue->EnableWindow(1);
        if (EnableSep->GetCheck() == 1)
            {
                LowSep->EnableWindow(1);
                HiSep->EnableWindow(1);
            }

Cap_Flag = 0;

return TRUE;

}

//**************************************************************************
LRESULT TGVDialog::CloseProcMsg(WPARAM,LPARAM)
    { if (Cap_Flag)
            {
                ExitMsg();
            }
        else
            {
         ptrMainApp->EnableCtl3dAutosubclass(TRUE);
                PProcDialog->ShowWindow(SW_HIDE);
                ptrMainApp->EnableCtl3dAutosubclass(FALSE);
            } return TRUE;

}

//**************************************************************************
void TGVDialog::DoCap()
    {
```

```
int x,y,w,h;
int pixx, pixy;
int moStep;
int CurrentTemp;

char StoneText[100];
LPSTR ptrStoneText = StoneText;

if (TimerState == 1)
        {
        StopLiveThread();
        QuickPic->Show(SW_HIDE);
        TimerState = 0;
        }

StartBtn->EnableWindow(0);
StopBtn->EnableWindow(1);

LiveBtn->Show(SW_HIDE);
StartBtn->Show(SW_SHOWNORMAL);

//      ::InvalidateRect(this->HWindow,NULL,TRUE);

ReflectOnly->EnableWindow(0);
DiffuseOnly->EnableWindow(0);
CurrentOnly->EnableWindow(0);
DoubleOnly->EnableWindow(0);
CompleteAnalysis->EnableWindow(0);
NinePosition->EnableWindow(0);
SkipSet->EnableWindow(0);
StoneBox->EnableWindow(0);
FinalImage->EnableWindow(0);
EnableSep->EnableWindow(0);
LowSep->EnableWindow(0);
HiSep->EnableWindow(0);
Set1->EnableWindow(0);
Set2->EnableWindow(0);
Set3->EnableWindow(0);
Manual1->EnableWindow(0);
Manual2->EnableWindow(0);
Manual3->EnableWindow(0);
IDValue->EnableWindow(0);

LightingGroup->Show(SW_SHOWNORMAL);
LightingGroup->Show(SW_HIDE);
LightingGroup->Show(SW_SHOWNORMAL);

ViewGroup->Show(SW_SHOWNORMAL);
SepGroup->Show(SW_SHOWNORMAL);
CurrentGroup->Show(SW_SHOWNORMAL);
ShowWaveBitmaps->Show(SW_SHOWNORMAL);
DiffuseOnly->Show(SW_SHOWNORMAL);
ReflectOnly->Show(SW_SHOWNORMAL);
CurrentOnly->Show(SW_SHOWNORMAL);
DoubleOnly->Show(SW_SHOWNORMAL);
FinalImage->Show(SW_SHOWNORMAL);
Set1->Show(SW_SHOWNORMAL);
Set2->Show(SW_SHOWNORMAL);
Set3->Show(SW_SHOWNORMAL);
EnableSep->Show(SW_SHOWNORMAL);
CompleteAnalysis->Show(SW_SHOWNORMAL);
NinePosition->Show(SW_SHOWNORMAL);
```

```
        SkipSet->Show(SW_SHOWNORMAL);
        Static_Text1->Show(SW_SHOWNORMAL);
        Static_Text2->Show(SW_SHOWNORMAL);
        Static_Text3->Show(SW_SHOWNORMAL);
        Static_Text4->Show(SW_SHOWNORMAL);
        Static_Text5->Show(SW_SHOWNORMAL);
        Static_Text6->Show(SW_SHOWNORMAL);
        Manual1->Show(SW_SHOWNORMAL);
        Manual2->Show(SW_SHOWNORMAL);
        Manual3->Show(SW_SHOWNORMAL);
        LowSep->Show(SW_SHOWNORMAL);
        HiSep->Show(SW_SHOWNORMAL);
        StoneBox->Show(SW_SHOWNORMAL);
        IDValue->Show(SW_SHOWNORMAL);

GetCurrentSets();

CurLightPos = 2;
        Cap_Flag = 1;
ptrMainApp->EnableCtl3dAutosubclass(TRUE);
        if (PProcDialog == NULL)
                {
                PProcDialog = new TProcDialog(Client, this,DIALOG_PROCESS_ID,31,ptrSysDevs);
                PProcDialog->Create();
                }
        PProcDialog->ShowWindow(SW_SHOW);
        ptrMainApp->EnableCtl3dAutosubclass(FALSE);

switch (CalState)
                {
                case 1:
                        ::PostMessage(PProcDialog->HWindow,WM_USER + 285,12,12);
                        break;
                case 0:
                        ::PostMessage(PProcDialog->HWindow,WM_USER + 225,12,12);
                        break;
                case 2:
                        ::PostMessage(PProcDialog->HWindow,WM_USER + 286,12,12);
                        break;

}

}

//***************************************************************************
void TGVDialog::EvTimer(UINT timerId)
        {
        int xpix;
        int     ypix;
        int xoff;
        int     yoff;
        int boxsize;
        int xcntr;
        int ycntr;

POINT           tic_points[2];
        LPPOINT         Poly_points;
        HPEN                            penOld;
        HPEN                            penYellow;

yoff = BoxUprYPos + BoxYOffset - 20;
        xoff = BoxUprXPos + BoxXOffset;
```

```
        boxsize = 168;

ptrSysDevs->ImageDevice->LiveFrame(CurLightPos,0,hLiveMemPtr,ptrSysDevs->UGTSContlr);

ycntr = 0;
        for (ypix = 1; ypix < boxsize * 2; ypix = ypix + 2)
            {
            xcntr = 0;
            for (xpix = 1; xpix < boxsize * 2; xpix = xpix + 2)
                {
                memcpy((PUCHAR) hLiveBmpPtr + ycntr*3*boxsize + xcntr*3,(PUCHAR) hLiveMemPtr +
(ypix+yoff)*640 + (xpix+xoff),1);
                memcpy((PUCHAR) hLiveBmpPtr + ycntr*3*boxsize + xcntr*3 + 1,(PUCHAR) hLiveMemPtr +
(ypix+yoff)*640 + (xpix+xoff),1);
                memcpy((PUCHAR) hLiveBmpPtr + ycntr*3*boxsize + xcntr*3 + 2,(PUCHAR) hLiveMemPtr +
(ypix+yoff)*640 + (xpix+xoff),1);
                xcntr = xcntr + 1;
                }
            ycntr = ycntr + 1;
            }

SetBitmapBits(PictureBmp,(DWORD) 84672,(PUCHAR) hLiveBmpPtr);
        BitBlt(winhdc,1,1,168,168,memhdc,0,0,SRCCOPY);

penYellow = CreatePen(PS_SOLID,1,RGB(0,255,255));
        penOld = (HPEN) SelectObject(winhdc,penYellow);

tic_points[0].x = 0;
        tic_points[0].y = 168/2;
        tic_points[1].x = 168;
        tic_points[1].y = 168/2;
        Poly_points = tic_points;
        Polyline(winhdc,Poly_points,2);

tic_points[0].x = 168/2;
        tic_points[0].y = 0;
        tic_points[1].x = 168/2;
        tic_points[1].y = 168;
        Poly_points = tic_points;
        Polyline(winhdc,Poly_points,2);

SelectObject(winhdc,penOld);

}

//****************************************************************************
void TGVDialog::SetCurrentSets()
    {
    char mbuf[10];

switch (Set_Number)
        {
        case 0:
            Set1->Check();
            break;
        case 1:
            Set2->Check();
            break;
        case 2:
            Set3->Check();
            break;
        }
```

```
CompleteAnalysis->Uncheck();
DiffuseOnly->Uncheck();
ReflectOnly->Uncheck();
DoubleOnly->Uncheck();
CurrentOnly->Uncheck();
NinePosition->Uncheck();
SkipSet->Uncheck();

Manual1->EnableWindow(0);
Manual2->EnableWindow(0);
Manual3->EnableWindow(0);

switch (Set_States[Set_Number])
    {
        case 0:
            CompleteAnalysis->Check();
            break;
        case 1:
            DiffuseOnly->Check();
            break;
        case 2:
            ReflectOnly->Check();
            break;
        case 3:
            DoubleOnly->Check();
            break;
        case 4:
            CurrentOnly->Check();
            Manual1->EnableWindow(1);
            Manual2->EnableWindow(1);
            Manual3->EnableWindow(1);
            break;
        case 5:
            NinePosition->Check();
            break;
        case 6:
            SkipSet->Check();
            break;
    } sprintf(mbuf,"%1.1f",Set_Manuals[Set_Number][0]);
Manual1->SetSelString(mbuf,0);
sprintf(mbuf,"%1.1f",Set_Manuals[Set_Number][1]);
Manual2->SetSelString(mbuf,0);
sprintf(mbuf,"%1.1f",Set_Manuals[Set_Number][2]);
Manual3->SetSelString(mbuf,0);

}

//************************************************************************
void TGVDialog::GetCurrentSets()
    {
        char mbuf[10], *endptr;

if (CompleteAnalysis->GetCheck() == 1) Set_States[Set_Number] = 0;
        if (DiffuseOnly->GetCheck() == 1) Set_States[Set_Number] = 1;
        if (ReflectOnly->GetCheck() == 1) Set_States[Set_Number] = 2;
        if (DoubleOnly->GetCheck() == 1) Set_States[Set_Number] = 3;
        if (CurrentOnly->GetCheck() == 1) Set_States[Set_Number] = 4;
        if (NinePosition->GetCheck() == 1) Set_States[Set_Number] = 5;
```

```
        if (SkipSet->GetCheck() == 1) Set_States[Set_Number] = 6;

Manual1->GetText(mbuf,10);
    Set_Manuals[Set_Number][0] = strtod(mbuf, &endptr);
    Manual2->GetText(mbuf,10);
    Set_Manuals[Set_Number][1] = strtod(mbuf, &endptr);
    Manual3->GetText(mbuf,10);
    Set_Manuals[Set_Number][2] = strtod(mbuf, &endptr);

}

//***************************************************************************
void TGVDialog::SetSet1()
    {

GetCurrentSets();
    Set_Number = 0;
    SetCurrentSets();

}

//***************************************************************************
void TGVDialog::SetSet2()
    {

GetCurrentSets();
    Set_Number = 1;
    SetCurrentSets();

}

//***************************************************************************
void TGVDialog::SetSet3()
    {

GetCurrentSets();
    Set_Number = 2;
    SetCurrentSets();

}

//***************************************************************************
void TGVDialog::DisableManual()
    {

Manual1->EnableWindow(0);
    Manual2->EnableWindow(0);
    Manual3->EnableWindow(0);

}

//***************************************************************************
void TGVDialog::EnableManual()
    {

Manual1->EnableWindow(1);
    Manual2->EnableWindow(1);
    Manual3->EnableWindow(1);

}

//***************************************************************************
```

```
void TGVDialog::WaveProcess()
    {
    char mbuf[10], *endptr;
    int wave_number = 400;

WaveBox->GetString(mbuf,WaveBox->GetSelIndex());
    wave_number = strtod(mbuf, &endptr);
    ptrSysDevs->FilterDevice->SetWave(wave_number);

}

//*************************************************************
void TGVDialog::PosProcess()
    {
    int curpos;
    int newpos;
    int difpos;
    int cntr;
    char mbuf[10], *endptr;

curpos = ptrSysDevs->MotionDevice->GetPos();
    PositionBox->GetString(mbuf,PositionBox->GetSelIndex());
    newpos = strtod(mbuf, &endptr)*10;
    difpos = newpos - curpos;

if (difpos > 0)
        {
        for (cntr = 0;cntr < difpos;cntr++)
            {
            if (ptrSysDevs->MotionDevice->moMovementStep != 0)
                {
                ptrSysDevs->MotionDevice->moMovementStep = 0;
                ptrSysDevs->MotionDevice->Move();
                Sleep(200);
                }
            else
                {
                ptrSysDevs->MotionDevice->Move();
                Sleep(100);
                }
            }
        } if (difpos < 0)
        {
        for (cntr = 0;cntr < abs(difpos);cntr++)
            {
            if (ptrSysDevs->MotionDevice->moMovementStep != 8)
                {
                ptrSysDevs->MotionDevice->moMovementStep = 8;
                ptrSysDevs->MotionDevice->Move();
                Sleep(200);
                }
            else
                {
                ptrSysDevs->MotionDevice->Move();
                Sleep(100);
                }
            }
        }

}
```

```
//****************************************************************************
void TGVDialog::WaveProcessEdit()
        {
        char mbuf[10], *endptr;
        int wave_number = 400;

WaveBox->GetText(mbuf,10);

wave_number = strtod(mbuf, &endptr);
        if ((wave_number > 700) || (wave_number < 400))
                {
//              Beep(3000,250);
                }
        else
                {
                ptrSysDevs->FilterDevice->SetWave(wave_number);
                }

}
//****************************************************************************
void TGVDialog::PosProcessEdit()
        {

}

//****************************************************************************
DWORD FAR PASCAL LivehProc(TGVDialog* ptrParent)
        {
        DWORD           rtnStatus = 1;

Sleep(1000);
        ptrParent->ptrSysDevs->MotionDevice->Home();
        Sleep(1000);
        while (LiveState == 1)
                {
                ptrParent->DoLive();
                } return rtnStatus;
        }

//****************************************************************************
void TGVDialog::DoLive()
        {
        int xpix;
        int     ypix;
        int xoff;
        int     yoff;
        int boxsize;
        int xcntr;
        int ycntr;

POINT           tic_points[2];
        LPPOINT         Poly_points;
        HPEN                            penOld;
        HPEN                            penYellow;

yoff = BoxUprYPos + BoxYOffset;
        xoff = BoxUprXPos + BoxXOffset;
```

```
            boxsize = 168;

ptrSysDevs->ImageDevice->LiveFrame(CurLightPos,0,hLiveMemPtr,ptrSysDevs->UGTSContlr);

ycntr = 0;
            for (ypix = 1; ypix < boxsize * 2; ypix = ypix + 2)
                {
                xcntr = 0;
                for (xpix = 1; xpix < boxsize * 2; xpix = xpix + 2)
                    {
                    memcpy((PUCHAR) hLiveBmpPtr + ycntr*3*boxsize + xcntr*3,(PUCHAR) hLiveMemPtr +
(ypix+yoff)*640 + (xpix+xoff),1);
                    memcpy((PUCHAR) hLiveBmpPtr + ycntr*3*boxsize + xcntr*3 + 1,(PUCHAR) hLiveMemPtr +
(ypix+yoff)*640 + (xpix+xoff),1);
                    memcpy((PUCHAR) hLiveBmpPtr + ycntr*3*boxsize + xcntr*3 + 2,(PUCHAR) hLiveMemPtr +
(ypix+yoff)*640 + (xpix+xoff),1);
                    xcntr = xcntr + 1;
                    }
                ycntr = ycntr + 1;
                }

SetBitmapBits(PictureBmp,(DWORD) 84672,(PUCHAR) hLiveBmpPtr);

penYellow = CreatePen(PS_SOLID,1,RGB(255,0,0));
//          penYellow = CreatePen(PS_SOLID,1,RGB(0,255,255));
            penOld = (HPEN) SelectObject(memhdc,penYellow);

tic_points[0].x = 0;
            tic_points[0].y = 168/2;
            tic_points[1].x = 168;
            tic_points[1].y = 168/2;
            Poly_points = tic_points;
            Polyline(memhdc,Poly_points,2);

tic_points[0].x = 168/2;
            tic_points[0].y = 0;
            tic_points[1].x = 168/2;
            tic_points[1].y = 168;
            Poly_points = tic_points;
            Polyline(memhdc,Poly_points,2);

SelectObject(memhdc,penOld);

BitBlt(winhdc,1,1,168,168,memhdc,0,0,SRCCOPY);

}

//**************************************************************************
void TGVDialog::StartLiveThread()
    { if (NULL == (hLiveThread =
                                            CreateThread( (LPSECURITY_ATTRIBUTES) NULL,
                                            0,
                                            (LPTHREAD_START_ROUTINE) LivehProc,
                                            this,
                                            0, &dwThreadID )))
            {
    ::MessageBox( HWindow,"No Live Thread Creation.","System Error" ,
            MB_ICONEXCLAMATION | MB_OK );
//              CaptureState = 0;
```

```
                    }
        else
                    {
//                  CaptureState = 1;
                    }
        }
//*************************************************************************
void TGVDialog::StopLiveThread()
        {
                LiveState = 0;
        }
//*************************************************************************
void TGVDialog::EvPaint()
        {
        BeginPaint(HWindow,&ps);
        if ((ps.rcPaint.left != 0) || (ps.rcPaint.top != 0))
                    {
                    ::InvalidateRect(HWindow,NULL,FALSE);
                    ::InvalidateRect(LightingGroup->HWindow,NULL,FALSE);
                    ::InvalidateRect(SepGroup->HWindow,NULL,FALSE);
                    ::InvalidateRect(CurrentGroup->HWindow,NULL,FALSE);
                    ::InvalidateRect(ViewGroup->HWindow,NULL,FALSE);
                    ::InvalidateRect(DiffuseOnly->HWindow,NULL,FALSE);
                    ::InvalidateRect(ReflectOnly->HWindow,NULL,FALSE);
                    ::InvalidateRect(CurrentOnly->HWindow,NULL,FALSE);
                    ::InvalidateRect(DoubleOnly->HWindow,NULL,FALSE);
                    ::InvalidateRect(CompleteAnalysis->HWindow,NULL,FALSE);
                    ::InvalidateRect(NinePosition->HWindow,NULL,FALSE);
                    ::InvalidateRect(SkipSet->HWindow,NULL,FALSE);
                    ::InvalidateRect(Set1->HWindow,NULL,FALSE);
                    ::InvalidateRect(Set2->HWindow,NULL,FALSE);
                    ::InvalidateRect(Set3->HWindow,NULL,FALSE);
                    ::InvalidateRect(PauseSets->HWindow,NULL,FALSE);
                    ::InvalidateRect(Manual1->HWindow,NULL,FALSE);
                    ::InvalidateRect(Manual2->HWindow,NULL,FALSE);
                    ::InvalidateRect(Manual3->HWindow,NULL,FALSE);
                    ::InvalidateRect(LowSep->HWindow,NULL,FALSE);
                    ::InvalidateRect(HiSep->HWindow,NULL,FALSE);
                    ::InvalidateRect(ShowWaveBitmaps->HWindow,NULL,FALSE);
                    ::InvalidateRect(EnableSep->HWindow,NULL,FALSE);
                    ::InvalidateRect(FinalImage->HWindow,NULL,FALSE);
                    ::InvalidateRect(Static_Text3->HWindow,NULL,FALSE);
                    ::InvalidateRect(Static_Text4->HWindow,NULL,FALSE);
                    ::InvalidateRect(Static_Text5->HWindow,NULL,FALSE);
                    ::InvalidateRect(Static_Text6->HWindow,NULL,FALSE);
                    ::InvalidateRect(QuitBtn->HWindow,NULL,FALSE);

::UpdateWindow(HWindow);

}

EndPaint(HWindow,&ps);

}
//*************************************************************************
```

```
void TGVDialog::EvMove(TPoint &clientOrigin)
    {

::SetWindowPos(HWindow,0,0,0,508,230,SWP_NOZORDER);

}

//**************************************************************************
BOOL TGVDialog::EvEraseBkgnd(HDC painthdc)
    {
    RECT        fillRect;

fillRect.left = 0;
    fillRect.top = 0;
    fillRect.right = 550;
    fillRect.bottom = 550;

::FillRect(GetDC(HWindow),&fillRect,(HBRUSH) GetStockObject(LTGRAY_BRUSH));
    ::FillRect(GetDC(LightingGroup->HWindow),&fillRect,(HBRUSH) GetStockObject(LTGRAY_BRUSH));
    ::FillRect(GetDC(PauseSets->HWindow),&fillRect,(HBRUSH) GetStockObject(LTGRAY_BRUSH));
    return 0;

}

//----------------------------------------------------------------------------
// Gem Vision - (C) Copyright 1995 by LambdaSpec Instruments
// TProcDlg
//---------------------------------------------------------------------------- include <owl\owlpch.h>
include <float.h>
#include <owl\dialog.h>
#include <owl\checkbox.h>
#include <owl\groupbox.h>
#include <owl\static.h>
#include <owl\edit.h>
#include <owl\button.h>
#include <owl\radiobut.h>
#include <owl\combobox.h>
#include <owl\mdi.h>
include <owl\statusba.h>
include <stdio.h>
#include <owl\point.h>
#include <owl\printer.h>
#include "math.h"

#include "mdifile.h"

#include "TFiltDev.h"       // Filter System Control.
#include "TMotDev.h"        // Motion System Control.
#include "TUGTSCN.h"                // UGTS Device Control.
#include "TImageDv.h"               // Capture Device Control.

extern TStatusBar* sb;
extern TTextGadget*     FrameView;
extern TTextGadget*     CompletePercent;
//extern int IsPoints[3][640][480];
extern int      ChamberTemp;
extern int      UseLowWaveLengths;

typedef struct
    {
```

```
    TMotionDevice* MotionDevice;
    TFilterDevice* FilterDevice;
    TUGTSDevice* UGTSContlr;
    TImageDevice* ImageDevice;
} SystemDevices;

#include "TCapDlg.h"              // Cap Dialog.

//#include "TVision.h"             // Vision Object.
//#include "TStatDlg.h"            // Stats dialog.

#if !defined(__UGTSPROCDLG_H)
define __UGTSPROCDLG_H include "rectext.h"

class PrintGemSpec : public TPrintout

{
        public:
            PrintGemSpec(const char* title,TWindow* window);
            void PrintPage(int page, TRect& rect, unsigned flags);
            BOOL HasPage(int pageNumber) {return pageNumber == 1;}
    void GetDialogInfo(int& minPage, int& maxPage,
            int& selFromPage, int& selToPage);
    void SetBanding(BOOL b) {Banding = b;}

TWindow*        ProcWindow;
            BOOL            Scale;
    };

typedef struct
    {
    char     title[100];
    } FrameData;

//**************************************************************************
//
// Creates Dialog box from rc file.
//
//**************************************************************************
class TProcDialog : public TDialog {
    private:
        PBITMAPINFO   ptrPictureInfo;
        HGDIOBJ                   hSelBmpObj;
        HANDLE                    hloc;
        DWORD                     givemebytes;
        TVision*         PVision[9];

int                       oldROPmode;
        int                       ImButtonDown;

TGroupBox*    LightGroup;
        TGroupBox*    StdGroup;
        TGroupBox*    SetGroup;

TStatic*      Frame1;
```

```
        TStatic*             Frame2;
        TStatic*             Frame3;

HBRUSH                          backBlack;
        HBRUSH                          backRed;
        HBRUSH                          backGreen;

HPEN                            penYellow;
        HPEN                            penMagenta;
        HPEN                            penAqua;

PAINTSTRUCT          ps;
        PrintGemSpec*  PrintRpt;
        TPrinter*            Printer;

TButton*             Single;
        TButton*             Construct;
        TButton*             HueGraph;
        TButton*             ToneGraph;
        TButton*             xyYGraph;
        TButton*             LabGraph;
        TButton*             uvGraph;
        TButton*             MoreGraph;
        TButton*             SaveBtn;
        TButton*             CloseBtn;

LPVOID                          ptrConstructBMP;
        LPVOID                          ptrConstructIMG;
        LPVOID                          ptrConstructXYZ;
        LPVOID                          ptrConstructRGB;

public:

BYTE IsPoints[3][640][480];

SystemDevices*  ptrSysDevs;
        Cie_Loci             cie_locus[322];

LPVOID                          hBmpMemPtr;
        HBITMAP              PictureBmp;
        HPEN                            penGreen;
        TPoint*              startPoint;
        TPoint*              endPoint;

TRadioButton*  LightA;
        TRadioButton*  LightB;
        TRadioButton*  LightC;
        TRadioButton*  LightD;
        TRadioButton*  Std1964;
        TRadioButton*  Std1931;
        TRadioButton*  SetBtn1;
        TRadioButton*  SetBtn2;
        TRadioButton*  SetBtn3;

TEdit*               Image1;
        TEdit*               Image2;
        TEdit*               Image3;
        TEdit*               ImageMain;

TEdit*               f1_CIExData;
        TEdit*               f2_CIExData;
        TEdit*               f3_CIExData;
```

```
TEdit*              f4_CIExData;

TEdit*              f1_CIEyData;
TEdit*              f2_CIEyData;
TEdit*              f3_CIEyData;
TEdit*              f4_CIEyData;

TEdit*              f1_CIEYData;
TEdit*              f2_CIEYData;
TEdit*              f3_CIEYData;
TEdit*              f4_CIEYData;

TEdit*              f1_CIELData;
TEdit*              f2_CIELData;
TEdit*              f3_CIELData;
TEdit*              f4_CIELData;

TEdit*              f1_CIEaData;
TEdit*              f2_CIEaData;
TEdit*              f3_CIEaData;
TEdit*              f4_CIEaData;

TEdit*              f1_CIEbData;
TEdit*              f2_CIEbData;
TEdit*              f3_CIEbData;
TEdit*              f4_CIEbData;

TEdit*              f1_SatData;
TEdit*              f2_SatData;
TEdit*              f3_SatData;
TEdit*              f4_SatData;

TEdit*              f1_DWLData;
TEdit*              f2_DWLData;
TEdit*              f3_DWLData;
TEdit*              f4_DWLData;

TEdit*              f1_ToneData;
TEdit*              f2_ToneData;
TEdit*              f3_ToneData;
TEdit*              f4_ToneData;

TEdit*              f1_Color;
TEdit*              f2_Color;
TEdit*              f3_Color;
TEdit*              f4_Color;

TEdit*              f1_Title;
TEdit*              f2_Title;
TEdit*              f3_Title;

UINT                Set_Number;

public:

TProcDialog::TProcDialog(TMDIClient* MainWindow, TGVDialog* ControlWindow, int dialogID, int Planes,
SystemDevices* SysDevices);
    ~TProcDialog();
    BOOL CanClose();
    void CommitMemory();
    void DeCommitMemory();
    LRESULT StartProcMsg(WPARAM,LPARAM);
```

```
LRESULT StopProcMsg(WPARAM,LPARAM);
LRESULT CalLighting(WPARAM,LPARAM);
LRESULT CalBacking(WPARAM,LPARAM);
LRESULT PrintCert(WPARAM,LPARAM);
friend DWORD FAR PASCAL Capture_hProc(TProcDialog* ptrParent);
friend DWORD FAR PASCAL Analyze_hProc(TProcDialog* ptrParent);
friend DWORD FAR PASCAL Crunch_hProc(TProcDialog* ptrParent);
void EvPaint();
HBRUSH  EvCtlColor(HDC hdc, HWND hWndChild, UINT ctlType);
void EvMove(TPoint &clientOrigin);
BOOL EvEraseBkgnd(HDC painthdc);
void EvActivate(UINT active,BOOL minimized,HWND hWndOther);
void EvMouseMove(UINT modkeys, TPoint & point);
void EvLButtonUp(UINT modkeys, TPoint & point);
void EvLButtonDown(UINT modkeys, TPoint & point);

void SetupWindow();
void RePaint();
void CloseProc();
void SetSet1();
void SetSet2();
void SetSet3();
void SetCurrentSets();
void GetCurrentSets();
void SetImage1();
void SetImage2();
void SetImage3();

void StartProcThreads();
void StopProcThreads();
int StartCapture();
void CaptureLoop();
void CrunchCapture();
int AnalyzeMsg();

void GraphCIExyY();
void GraphCIELab();
void ReProcess();
void StartConstruct();
void SaveGroup();

DWORD           dwThreadID_Capture;
DWORD           dwThreadID_Analyze;
DWORD           dwThreadID_Crunch;
HANDLE          hThread_Capture;
HANDLE          hThread_Analyze;
HANDLE          hThread_Crunch;

LPVOID          ptrBitmapMem[9];
LPVOID          ptrImageMem[9];
LPVOID          ptrXYZMem[9];
LPVOID          ptrRGBMem[9];
LPVOID          hImageMemAlloc;
LPVOID          hImageMemBegin;
LPVOID          hImageMemStart;
HDC             image_winhdc[9];
HDC             image_memhdc[9];
int             Current_Calibration;

UINT            Current_Frame;
FrameData       frameData[9];
FrameData*      frmData[9];
```

```
            FLOAT              ConstructBackVals[31][3];

int                BoxXOffset;
            int                BoxYOffset;
            int                BoxUprXPos;
            int                BoxUprYPos;
            int                BoxLowXPos;
            int                BoxLowYPos;
            int                BoxMaxX;
            int                BoxMaxY;
            int                WinRowStart;
            int                WinRowEnd;
            int                WinColStart;
            int                WinColEnd;
            int                WinXSize;
            int                WinYSize;

HDC                winhdc;
            HDC                memhdc;

int                ShowWholeWindow;
            int                Total_Planes;
            TGVDialog*    ControlWin;

int                UseLargeImage;

DECLARE_RESPONSE_TABLE(TProcDialog);

};

#endif

//*****************************************************************************
DEFINE_RESPONSE_TABLE1(TProcDialog, TDialog)
        EV_WM_CTLCOLOR,
    EV_COMMAND(IDC_CLOSE, CloseProc),
    EV_MESSAGE(WM_USER+225, StartProcMsg),
    EV_MESSAGE(WM_USER+226, StopProcMsg),
    EV_MESSAGE(WM_USER+285, CalLighting),
    EV_MESSAGE(WM_USER+286, CalBacking),
    EV_MESSAGE(WM_USER+401, PrintCert),
        EV_WM_PAINT,
        EV_WM_MOVE,
        EV_WM_ERASEBKGND,
    EV_COMMAND(IDC_SETBUTTON1, SetSet1),
    EV_COMMAND(IDC_SETBUTTON2, SetSet2),
    EV_COMMAND(IDC_SETBUTTON3, SetSet3),
    EV_COMMAND(IDC_LIGHTA, ReProcess),
    EV_COMMAND(IDC_LIGHTB, ReProcess),
    EV_COMMAND(IDC_LIGHTC, ReProcess),
    EV_COMMAND(IDC_LIGHTD, ReProcess),
    EV_COMMAND(IDC_STD10DEGREE, ReProcess),
    EV_COMMAND(IDC_STD2DEGREE, ReProcess),
    EV_EN_SETFOCUS(IDC_IMAGE1, SetImage1),
    EV_EN_SETFOCUS(IDC_IMAGE2, SetImage2),
    EV_EN_SETFOCUS(IDC_IMAGE3, SetImage3),
    EV_COMMAND(IDC_XYYGRAPH, GraphCIExyY),
    EV_COMMAND(IDC_LABGRAPH, GraphCIELab),
    EV_COMMAND(IDC_CONSTRUCT, StartConstruct),
    EV_COMMAND(IDOK, SaveGroup),
        EV_WM_LBUTTONDOWN,
```

```
        EV_WM_LBUTTONUP,
        EV_WM_MOUSEMOVE,
//      EV_WM_ACTIVATE,
END_RESPONSE_TABLE;

//****************************************************************************
TProcDialog::TProcDialog(TMDIClient* MainWindow, TGVDialog* ControlWindow, int dialogID, int Planes, SystemDevices*
SysDevices) :TDialog(MainWindow,dialogID), TWindow(MainWindow)
        {
        DWORD                           givemebytes;
        int                             q;
        int     CicLocusFile;
        int     i;
        SYSTEM_INFO sysInfo;

typedef struct CBuffer
                {
                char  a[4];
                char  b[10];
                char  c[10];
                char  d[1];
                } CBUF;

CBUF cBuf;

ptrSysDevs = SysDevices;

ControlWin = ControlWindow;

Set_Number = 0;

ShowWholeWindow = 0;
        Total_Planes = Planes;
        UseLargeImage = 0;
        Current_Frame = 0;

startPoint = new TPoint();
        endPoint = new TPoint();

frmData[0] = &frameData[0];
        frmData[1] = &frameData[1];
        frmData[2] = &frameData[2];
        frmData[3] = &frameData[3];
        frmData[4] = &frameData[4];
        frmData[5] = &frameData[5];
        frmData[6] = &frameData[6];
        frmData[7] = &frameData[7];
        frmData[8] = &frameData[8];

// see timagedev constructor for values!
        BoxYOffset = ptrSysDevs->ImageDevice->BoxYOffset;
        BoxXOffset = ptrSysDevs->ImageDevice->BoxXOffset;
        BoxUprXPos = ptrSysDevs->ImageDevice->BoxUprXPos;
        BoxUprYPos = ptrSysDevs->ImageDevice->BoxUprYPos;
        BoxLowXPos = ptrSysDevs->ImageDevice->BoxLowXPos;
        BoxLowYPos = ptrSysDevs->ImageDevice->BoxLowYPos;

if (ShowWholeWindow == 1)
                {
                WinRowStart = 0;
                WinRowEnd = 480;
                WinColStart = 0;
```

```
                WinColEnd = 640;
                }
        else
                {
                WinRowStart = BoxUprYPos + BoxYOffset;
                WinRowEnd = BoxLowYPos + BoxYOffset;
                WinColStart = BoxUprXPos + BoxXOffset;
                WinColEnd = BoxLowXPos + BoxXOffset;
                }
        WinYSize = WinRowEnd - WinRowStart;
        WinXSize = WinColEnd - WinColStart;

backBlack = CreateSolidBrush(RGB(0,0,0));
        backRed = CreateSolidBrush(RGB(255,0,0));
        backGreen = CreateSolidBrush(RGB(0,255,0));
        penGreen = CreatePen(PS_SOLID,1,RGB(0,255,0));
        penYellow = CreatePen(PS_SOLID,1,RGB(255,255,0));
        penMagenta = CreatePen(PS_SOLID,1,RGB(255,0,255));
        penAqua = CreatePen(PS_SOLID,1,RGB(0,255,255));

LightGroup = new TGroupBox(this, IDC_LIGHTGROUP);
        StdGroup = new TGroupBox(this, IDC_STDGROUP);
        SetGroup = new TGroupBox(this, IDC_SETGROUP);

Frame1 = new TStatic(this, IDC_FRAME1);
        Frame2 = new TStatic(this, IDC_FRAME2);
        Frame3 = new TStatic(this, IDC_FRAME3);

LightA = new TRadioButton(this, IDC_LIGHTA, LightGroup);
        LightB = new TRadioButton(this, IDC_LIGHTB, LightGroup);
        LightC = new TRadioButton(this, IDC_LIGHTC, LightGroup);
        LightD = new TRadioButton(this, IDC_LIGHTD, LightGroup);
        Std1964 = new TRadioButton(this, IDC_STD10DEGREE, StdGroup);
        Std1931 = new TRadioButton(this, IDC_STD2DEGREE, StdGroup);
        SetBtn1 = new TRadioButton(this, IDC_SETBUTTON1, StdGroup);
        SetBtn2 = new TRadioButton(this, IDC_SETBUTTON2, StdGroup);
        SetBtn3 = new TRadioButton(this, IDC_SETBUTTON3, StdGroup);

Single = new TButton(this, IDC_SINGLEBTN);
        Construct = new TButton(this, IDC_CONSTRUCT);
        HueGraph = new TButton(this, IDC_HUEGRAPH);
        ToneGraph = new TButton(this, IDC_TONEGRAPH);
        xyYGraph = new TButton(this, IDC_XYYGRAPH);
        LabGraph = new TButton(this, IDC_LABGRAPH);
        uvGraph = new TButton(this, IDC_UVGRAPH);
        MoreGraph = new TButton(this, IDC_MOREGRAPH);
        SaveBtn = new TButton(this, IDOK);
        CloseBtn = new TButton(this, IDC_CLOSE);

Image1 = new TEdit(this, IDC_IMAGE1);
        Image2 = new TEdit(this, IDC_IMAGE2);
        Image3 = new TEdit(this, IDC_IMAGE3);
        ImageMain = new TEdit(this, IDC_MAINIMAGE);

f1_SatData = new TEdit(this, IDC_F1_SAT);
        f2_SatData = new TEdit(this, IDC_F2_SAT);
        f3_SatData = new TEdit(this, IDC_F3_SAT);
        f4_SatData = new TEdit(this, IDC_F4_SAT);

f1_DWLData = new TEdit(this, IDC_F1_DWL);
        f2_DWLData = new TEdit(this, IDC_F2_DWL);
        f3_DWLData = new TEdit(this, IDC_F3_DWL);
```

```
f4_DWLData = new TEdit(this, IDC_F4_DWL);

f1_ToneData = new TEdit(this, IDC_F1_TONE);
f2_ToneData = new TEdit(this, IDC_F2_TONE);
f3_ToneData = new TEdit(this, IDC_F3_TONE);
f4_ToneData = new TEdit(this, IDC_F4_TONE);

f1_Color = new TEdit(this, IDC_F1_COLOR);
f2_Color = new TEdit(this, IDC_F2_COLOR);
f3_Color = new TEdit(this, IDC_F3_COLOR);
f4_Color = new TEdit(this, IDC_F4_COLOR);

f1_CIExData = new TEdit(this, IDC_F1_CIE_X);
f2_CIExData = new TEdit(this, IDC_F2_CIE_X);
f3_CIExData = new TEdit(this, IDC_F3_CIE_X);
f4_CIExData = new TEdit(this, IDC_F4_CIE_X);

f1_CIEyData = new TEdit(this, IDC_F1_CIE_Y);
f2_CIEyData = new TEdit(this, IDC_F2_CIE_Y);
f3_CIEyData = new TEdit(this, IDC_F3_CIE_Y);
f4_CIEyData = new TEdit(this, IDC_F4_CIE_Y);

f1_CIEYData = new TEdit(this, IDC_F1_CIE_BIGY);
f2_CIEYData = new TEdit(this, IDC_F2_CIE_BIGY);
f3_CIEYData = new TEdit(this, IDC_F3_CIE_BIGY);
f4_CIEYData = new TEdit(this, IDC_F4_CIE_BIGY);

f1_CIELData = new TEdit(this, IDC_F1_CIE_L);
f2_CIELData = new TEdit(this, IDC_F2_CIE_L);
f3_CIELData = new TEdit(this, IDC_F3_CIE_L);
f4_CIELData = new TEdit(this, IDC_F4_CIE_L);

f1_CIEaData = new TEdit(this, IDC_F1_CIE_A);
f2_CIEaData = new TEdit(this, IDC_F2_CIE_A);
f3_CIEaData = new TEdit(this, IDC_F3_CIE_A);
f4_CIEaData = new TEdit(this, IDC_F4_CIE_A);

f1_CIEbData = new TEdit(this, IDC_F1_CIE_B);
f2_CIEbData = new TEdit(this, IDC_F2_CIE_B);
f3_CIEbData = new TEdit(this, IDC_F3_CIE_B);
f4_CIEbData = new TEdit(this, IDC_F4_CIE_B);

f1_Title = new TEdit(this, IDC_TITLE1);
f2_Title = new TEdit(this, IDC_TITLE2);
f3_Title = new TEdit(this, IDC_TITLE3);

Printer = new TPrinter();

//      PrintRpt = new PrintGemSpec("John is back!",this);
//      PrintRpt->SetBanding(TRUE);
//      Printer->Print(this,PrintRpt,FALSE);
//      PrintRpt = new PrintGemSpec("John is back!",this);

// Allocate Virtual memory

GetSystemInfo(&sysInfo);

givemebytes = 10*((     Total_Planes * WinXSize*WinYSize) + (338 * 336 * 3) + (168 * 168 * 3) +
(WinXSize*WinYSize * 3 * 4) ) + (338 * 336 * 3) + sysInfo.dwPageSize*60;
        hImageMemAlloc = VirtualAlloc((LPVOID) NULL, givemebytes, MEM_RESERVE, PAGE_READWRITE);
```

```
            if (hImageMemAlloc == NULL)
                {
        ::MessageBox( HWindow,"Unable to allocate Process memory.","System Error.",
                MB_ICONEXCLAMATION | MB_OK );
                    CloseWindow();
                    return;
                } hImageMemBegin = hImageMemAlloc;

// Commit amount actually needed now givemebytes = 338 * 336 * 3;
            givemebytes = (givemebytes/sysInfo.dwPageSize);
            givemebytes = (givemebytes+1)*sysInfo.dwPageSize;
            hBmpMemPtr = VirtualAlloc(hImageMemAlloc, givemebytes, MEM_COMMIT, PAGE_READWRITE);
            (PUCHAR) hImageMemAlloc = (PUCHAR) hImageMemAlloc + givemebytes;

givemebytes = 168 * 168 * 3;
            givemebytes = (givemebytes/sysInfo.dwPageSize);
            givemebytes = (givemebytes+1)*sysInfo.dwPageSize;
            ptrConstructBMP = VirtualAlloc(hImageMemAlloc, givemebytes, MEM_COMMIT, PAGE_READWRITE);
            (PUCHAR) hImageMemAlloc = (PUCHAR) hImageMemAlloc + givemebytes;

givemebytes = Total_Planes * WinXSize*WinYSize;
            givemebytes = (givemebytes/sysInfo.dwPageSize);
            givemebytes = (givemebytes+1)*sysInfo.dwPageSize;
            ptrConstructIMG = VirtualAlloc(hImageMemAlloc, givemebytes, MEM_COMMIT, PAGE_READWRITE);
            (PUCHAR) hImageMemAlloc = (PUCHAR) hImageMemAlloc + givemebytes;

givemebytes = WinXSize*WinYSize * 3 * 4;
            givemebytes = (givemebytes/sysInfo.dwPageSize);
            givemebytes = (givemebytes+1)*sysInfo.dwPageSize;
            ptrConstructXYZ = VirtualAlloc(hImageMemAlloc, givemebytes, MEM_COMMIT, PAGE_READWRITE);
            (PUCHAR) hImageMemAlloc = (PUCHAR) hImageMemAlloc + givemebytes;

givemebytes = 338 * 336 * 3;
            givemebytes = (givemebytes/sysInfo.dwPageSize);
            givemebytes = (givemebytes+1)*sysInfo.dwPageSize;
            ptrConstructRGB = VirtualAlloc(hImageMemAlloc, givemebytes, MEM_COMMIT, PAGE_READWRITE);
            (PUCHAR) hImageMemAlloc = (PUCHAR) hImageMemAlloc + givemebytes;

hImageMemStart = hImageMemAlloc;

CieLocusFile = _lopen("CIELOCUS",OF_READ);
            if (CieLocusFile == 0)
                {
        ::MessageBox( HWindow,"Unable to open CIELOCUS file!.","System Error.",
                MB_ICONEXCLAMATION | MB_OK );
                }
            for (i = 0;i < 321;i++)
                {
                    _lread(CieLocusFile,(LPSTR) &cBuf,25);
                    cBuf.a[3] = NULL;
                    cBuf.b[9] = NULL;
                    cBuf.c[9] = NULL;
                    cie_locus[i].dwI = atoi(cBuf.a);
                    cie_locus[i].fx = atof(cBuf.b);
                    cie_locus[i].fy = atof(cBuf.c);
                }
            _lclose(CieLocusFile);
```

```
          };
//*****************************************************************
TProcDialog::~TProcDialog()
        {

SelectObject(memhdc,hSelBmpObj);
        DeleteObject(PictureBmp);

DeleteDC(memhdc);
        ReleaseDC(HWindow,winhdc);

if (hImageMemStart != NULL)
                {
                VirtualFree(hImageMemBegin, 0, MEM_RELEASE);
                }

}

//*****************************************************************
void TProcDialog::CommitMemory()
        {
        DWORD                   givemebytes;
        int                     q;
        SYSTEM_INFO  sysInfo;
        char            tbuff[100];

GetSystemInfo(&sysInfo);

//              sprintf(tbuff,"%d",sysInfo.dwPageSize);
//              f4_ClExData->SetText(tbuff);
//      UpdateWindow();
//
//      ::MessageBox( HWindow,"Paused.","System Error." ,
//              MB_ICONEXCLAMATION | MB_OK ) ;

hImageMemAlloc = hImageMemStart;

for (q = 0;q < 3;q++)
                {
                switch (ControlWin->Set_States[q])
                        {
                        case 1:
                                givemebytes = 168 * 168 * 3;
                                givemebytes = (givemebytes/sysInfo.dwPageSize);
                                givemebytes = (givemebytes+1)*sysInfo.dwPageSize;
                                ptrBitmapMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = Total_Planes * WinXSize*WinYSize;
                                givemebytes = (givemebytes/sysInfo.dwPageSize);
                                givemebytes = (givemebytes+1)*sysInfo.dwPageSize;
                                ptrImageMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = WinXSize*WinYSize * 3 * 4;
                                givemebytes = (givemebytes/sysInfo.dwPageSize);
                                givemebytes = (givemebytes+1)*sysInfo.dwPageSize;
```

```
                    ptrXYZMem[q*3] = VirtualAlloc(hImageMemAlloc, givemebytes, MEM_COMMIT,
PAGE_READWRITE);
                    (PUCHAR) hImageMemAlloc = (PUCHAR) hImageMemAlloc + givemebytes;

givemebytes = 338 * 336 * 3;
                    givemebytes = (givemebytes/sysInfo.dwPageSize);
                    givemebytes = (givemebytes+1)*sysInfo.dwPageSize;
                    ptrRGBMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                    break;
             case 2:
                    givemebytes = 168 * 168 * 3;
                    givemebytes = (givemebytes/sysInfo.dwPageSize);
                    givemebytes = (givemebytes+1)*sysInfo.dwPageSize;
                    ptrBitmapMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = Total_Planes * WinXSize*WinYSize;
                    givemebytes = (givemebytes/sysInfo.dwPageSize);
                    givemebytes = (givemebytes+1)*sysInfo.dwPageSize;
                    ptrImageMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = WinXSize*WinYSize * 3 * 4;
                    givemebytes = (givemebytes/sysInfo.dwPageSize);
                    givemebytes = (givemebytes+1)*sysInfo.dwPageSize;
                    ptrXYZMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = 338 * 336 * 3;
                    givemebytes = (givemebytes/sysInfo.dwPageSize);
                    givemebytes = (givemebytes+1)*sysInfo.dwPageSize;
                    ptrRGBMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                    break;
             case 3:
                    givemebytes = 168 * 168 * 3;
                    givemebytes = (givemebytes/sysInfo.dwPageSize);
                    givemebytes = (givemebytes+1)*sysInfo.dwPageSize;
                    ptrBitmapMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = Total_Planes * WinXSize*WinYSize;
                    givemebytes = (givemebytes/sysInfo.dwPageSize);
                    givemebytes = (givemebytes+1)*sysInfo.dwPageSize;
                    ptrImageMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = WinXSize*WinYSize * 3 * 4;
                    givemebytes = (givemebytes/sysInfo.dwPageSize);
                    givemebytes = (givemebytes+1)*sysInfo.dwPageSize;
                    ptrXYZMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
```

```
                                    givemebytes = 338 * 336 * 3;
                                    givemebytes = (givemebytes/sysInfo.dwPageSize);
                                    givemebytes = (givemebytes+1)*sysInfo.dwPageSize;
                                    ptrRGBMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    break;
                            case 0:
                                    givemebytes = 168 * 168 * 3;
                                    givemebytes = (givemebytes/sysInfo.dwPageSize);
                                    givemebytes = (givemebytes+1)*sysInfo.dwPageSize;
                                    ptrBitmapMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    ptrBitmapMem[q*3+1] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    ptrBitmapMem[q*3+2] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = Total_Planes * WinXSize*WinYSize;
                                    givemebytes = (givemebytes/sysInfo.dwPageSize);
                                    givemebytes = (givemebytes+1)*sysInfo.dwPageSize;
                                    ptrImageMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    ptrImageMem[q*3+1] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    ptrImageMem[q*3+2] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = WinXSize*WinYSize * 3 * 4;
                                    givemebytes = (givemebytes/sysInfo.dwPageSize);
                                    givemebytes = (givemebytes+1)*sysInfo.dwPageSize;
                                    ptrXYZMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    ptrXYZMem[q*3+1] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    ptrXYZMem[q*3+2] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = 338 * 336 * 3;
                                    givemebytes = (givemebytes/sysInfo.dwPageSize);
                                    givemebytes = (givemebytes+1)*sysInfo.dwPageSize;
                                    ptrRGBMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    ptrRGBMem[q*3+1] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    ptrRGBMem[q*3+2] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                                    break;
                            case 4:
                                    givemebytes = 168 * 168 * 3;
```

```
                              givemebytes = (givemebytes/sysInfo.dwPageSize);
                              givemebytes = (givemebytes+1)*sysInfo.dwPageSize;
                              ptrBitmapMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              ptrBitmapMem[q*3+1] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              ptrBitmapMem[q*3+2] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = Total_Planes * WinXSize*WinYSize;
                              givemebytes = (givemebytes/sysInfo.dwPageSize);
                              givemebytes = (givemebytes+1)*sysInfo.dwPageSize;
                              ptrImageMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              ptrImageMem[q*3+1] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              ptrImageMem[q*3+2] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = WinXSize*WinYSize * 3 * 4;
                              givemebytes = (givemebytes/sysInfo.dwPageSize);
                              givemebytes = (givemebytes+1)*sysInfo.dwPageSize;
                              ptrXYZMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              ptrXYZMem[q*3+1] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              ptrXYZMem[q*3+2] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;

givemebytes = 338 * 336 * 3;
                              givemebytes = (givemebytes/sysInfo.dwPageSize);
                              givemebytes = (givemebytes+1)*sysInfo.dwPageSize;
                              ptrRGBMem[q*3] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              ptrRGBMem[q*3+1] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              ptrRGBMem[q*3+2] = VirtualAlloc(hImageMemAlloc, givemebytes, MEM_COMMIT,
PAGE_READWRITE);

(PUCHAR) hImageMemAlloc = (PUCHAR) hImageMemAlloc + givemebytes;
                              break;
                     }
            }
     }

//*********************************************************************
void TProcDialog::DeCommitMemory()
     {
     DWORD                    givemebytes;
     int                      q;
     int                      i1;
```

```
SYSTEM_INFO sysInfo;

GetSystemInfo(&sysInfo);

for (i1 = 0;i1 < 10;i1++)
        {
        ControlWin->PStatDialog->SetSpectralFrame(i1,0);
        }
ControlWin->PStatDialog->GraphSpectral();

ZeroMemory(hBmpMemPtr,340704);
SetBitmapBits(PictureBmp,(DWORD) 340704,(PUCHAR) hBmpMemPtr);
BitBlt(winhdc,1,1,338,335,memhdc,0,0,SRCCOPY);

for (q = 0;q < 9;q++)
        {
        if (PVision[q] != NULL)
                {
                delete PVision[q];

PVision[q] = NULL;

/*
                givemebytes = 338 * 336 * 3;
                givemebytes = (givemebytes/sysInfo.dwPageSize);
                givemebytes = (givemebytes+1)*sysInfo.dwPageSize;
                VirtualFree(ptrRGBMem[q], givemebytes, MEM_DECOMMIT);

givemebytes = WinXSize*WinYSize * 3 * 4;
                givemebytes = (givemebytes/sysInfo.dwPageSize);
                givemebytes = (givemebytes+1)*sysInfo.dwPageSize;
                VirtualFree(ptrXYZMem[q], givemebytes, MEM_DECOMMIT);

givemebytes = Total_Planes * WinXSize*WinYSize;
                givemebytes = (givemebytes/sysInfo.dwPageSize);
                givemebytes = (givemebytes+1)*sysInfo.dwPageSize;
                VirtualFree(ptrImageMem[q], givemebytes, MEM_DECOMMIT);

givemebytes = 168 * 168 * 3;
                givemebytes = (givemebytes/sysInfo.dwPageSize);
                givemebytes = (givemebytes+1)*sysInfo.dwPageSize;
                VirtualFree(ptrBitmapMem[q], givemebytes, MEM_DECOMMIT);
*/

}
        } hImageMemAlloc = hImageMemStart;
    givemebytes = 9*((338 * 336 * 3) + (WinXSize*WinYSize * 3 * 4) + (Total_Planes * WinXSize*WinYSize) + (168 * 168 * 3));
    givemebytes = (givemebytes/sysInfo.dwPageSize);
    givemebytes = (givemebytes+9*4)*sysInfo.dwPageSize;

if (!VirtualFree(hImageMemAlloc, givemebytes, MEM_DECOMMIT))
            {
    ::MessageBox( HWindow,"Unable to release Process memory.","System Error." ,
            MB_ICONEXCLAMATION | MB_OK );
            }

}

//*********************************************************************
```

```
//
// Close out Window.
//
//*************************************************************************
BOOL TProcDialog::CanClose()

{
//              ::MessageBox( HWindow,"CanClose.","System Error." ,
//                      MB_ICONEXCLAMATION | MB_OK ) ;

return 1;

};

//*************************************************************************
//
// Setup Dialog.
//
//*************************************************************************
void TProcDialog::SetupWindow()

{
        char            TitleText[100];
        char            tempText[100];
        char            StoneType[100];
        LPSTR           ptrStoneType;

TDialog::SetupWindow();

SetBtn1->Check();
        Std1931->Check();
        LightD->Check();

winhdc = GetDC(ImageMain->HWindow);
        memhdc = CreateCompatibleDC(NULL);

hloc = LocalAlloc(LMEM_ZEROINIT | LMEM_MOVEABLE,sizeof(BITMAPINFOHEADER));
        ptrPictureInfo = (PBITMAPINFO) LocalLock(hloc);

if (ptrPictureInfo == NULL)
                {
        ::MessageBox( HWindow,"Unable to commit local memory.","System Error." ,
                MB_ICONEXCLAMATION | MB_OK ) ;
                CloseWindow();
                return;
                } ptrPictureInfo->bmiHeader.biSize = sizeof(BITMAPINFOHEADER);
        ptrPictureInfo->bmiHeader.biWidth = 338;
        ptrPictureInfo->bmiHeader.biHeight = 336;
        ptrPictureInfo->bmiHeader.biPlanes = 1;
        ptrPictureInfo->bmiHeader.biBitCount = 24;
        ptrPictureInfo->bmiHeader.biCompression = BI_RGB;
        ptrPictureInfo->bmiHeader.biSizeImage = 0;
        ptrPictureInfo->bmiHeader.biXPelsPerMeter = 0;
        ptrPictureInfo->bmiHeader.biYPelsPerMeter = 0;
        ptrPictureInfo->bmiHeader.biClrUsed = 0;
        ptrPictureInfo->bmiHeader.biClrImportant = 0;

PictureBmp = CreateDIBitmap(memhdc,(BITMAPINFOHEADER FAR*) ptrPictureInfo, CBM_CREATEDIB,
hBmpMemPtr, ptrPictureInfo, 0);
```

```
        if (PictureBmp == NULL)
            {
    ::MessageBox( HWindow,"Unable to create DIBitmap.","System Error.",
            MB_ICONEXCLAMATION | MB_OK );
                return;
                } hSelBmpObj = SelectObject(memhdc,PictureBmp);

ptrStoneType = StoneType;
        ControlWin->StoneBox->GetText(ptrStoneType,100);
        strcpy(TitleText,ptrStoneType);
        strcat(TitleText," - ");
        ControlWin->IDValue->GetText(tempText,99);
        strcat(TitleText,tempText);
        SetCaption(TitleText);
        SetCurrentSets();

Image1->SetCursor(0,IDC_ARROW);
        Image2->SetCursor(0,IDC_ARROW);
        Image3->SetCursor(0,IDC_ARROW);
        ImageMain->SetCursor(0,IDC_ARROW);

};

//*****************************************************************************
//
// Paint Dialog.
//
//*****************************************************************************
void TProcDialog::RePaint()
        {
        int             image_cntr = 0;
        RECT    main_image_rect;
        int il;

BitBlt(winhdc,1,1,338,336,memhdc,0,0,SRCCOPY);

switch (Set_Number)
                {
                case 0:
                        for (i1 = 0;i1 < 3;i1++)
                                {
                                if (PVision[i1] != NULL)
                                        {
                                        PVision[i1]->PaintImage();
                                        PVision[i1]->ShowData();
                                        }
                                }
                        break;
                case 1:
                        for (i1 = 3;i1 < 6;i1++)
                                {
                                if (PVision[i1] != NULL)
                                        {
                                        PVision[i1]->PaintImage();
                                        PVision[i1]->ShowData();
                                        }
                                }
                        break;
                case 2:
```

```
                        for (i1 = 6;i1 < 9;i1++)
                            {
                            if (PVision[i1] != NULL)
                                {
                                PVision[i1]->PaintImage();
                                PVision[i1]->ShowData();
                                }
                            }
                        break;
                    }
            };

//****************************************************************************
//
//
//****************************************************************************
HBRUSH TProcDialog::EvCtlColor(HDC hdc, HWND hWndChild, UINT ctlType)
        { int ResID;
        int     yo=0;

ResID = ::GetDlgCtrlID(hWndChild);

switch (ResID)
                {
                case IDC_TITLE1:
                        ::SetTextColor(hdc,RGB(255,255,0));
                        yo = 1;
                        break;
                case IDC_TITLE2:
                        ::SetTextColor(hdc,RGB(255,0,255));
                        yo = 1;
                        break;
                case IDC_TITLE3:
                        ::SetTextColor(hdc,RGB(0,255,255));
                        yo = 1;
                        break;
                case IDC_IMAGE1:
                        ::SetTextColor(hdc,RGB(0,255,0));
                        yo = 1;
                        break;
                case IDC_IMAGE2:
                        ::SetTextColor(hdc,RGB(0,255,0));
                        yo = 1;
                        break;
                case IDC_IMAGE3:
                        ::SetTextColor(hdc,RGB(0,255,0));
                        yo = 1;
                        break;
                case IDC_MAINIMAGE:
                        ::SetTextColor(hdc,RGB(0,255,0));
                        yo = 1;
                        break;
                } if (yo == 1)
                {
                ::SetBkColor(hdc,RGB(0,0,0));
                return backBlack;
                }
```

```
                return FALSE;
        };

//***************************************************************************
//
// Close out proc.
//
//***************************************************************************
void TProcDialog::CloseProc()
        { if (!ControlWin->Cap_Flag) DeCommitMemory();
        ::PostMessage(ControlWin->HWindow,WM_USER + 201,12,12);

};

//***************************************************************************
LRESULT TProcDialog::StartProcMsg(WPARAM,LPARAM)
        {
        int i1;
        RECT            fillRect;

LightA->EnableWindow(0);
        LightB->EnableWindow(0);
        LightC->EnableWindow(0);
        LightD->EnableWindow(0);
        Std1964->EnableWindow(0);
        Std1931->EnableWindow(0);
        SetBtn1->EnableWindow(0);
        SetBtn2->EnableWindow(0);
        SetBtn3->EnableWindow(0);

Single->EnableWindow(0);
        Construct->EnableWindow(0);
        HueGraph->EnableWindow(0);
        ToneGraph->EnableWindow(0);
        xyYGraph->EnableWindow(0);
        LabGraph->EnableWindow(0);
        uvGraph->EnableWindow(0);
        MoreGraph->EnableWindow(0);
        SaveBtn->EnableWindow(0);
//      CloseBtn->EnableWindow(0);

CommitMemory();

StartProcThreads();

return TRUE;

}

//***************************************************************************
LRESULT TProcDialog::StopProcMsg(WPARAM,LPARAM)
        {

StopProcThreads();

return TRUE;

}
```

```cpp
//*****************************************************************
DWORD FAR PASCAL Capture_hProc(TProcDialog* ptrParent)
    {
        DWORD       rtnStatus = 1;
        int         strtn;

/*
        strtn = SetPriorityClass(GetCurrentProcess(),REALTIME_PRIORITY_CLASS);
        if (strtn == FALSE)
            {
    ::MessageBox( ptrParent->HWindow,"Unable to set priority class.","System Error.",
                MB_ICONEXCLAMATION | MB_OK ) ;
            }
*/ ptrParent->CaptureLoop();

/*
        strtn = SetPriorityClass(GetCurrentProcess(),NORMAL_PRIORITY_CLASS);
        if (strtn == FALSE)
            {
    ::MessageBox( ptrParent->HWindow,"Unable to reset priority class.","System Error.",
                MB_ICONEXCLAMATION | MB_OK ) ;
            }
*/ return rtnStatus;
    }

//*****************************************************************
DWORD FAR PASCAL Analyze_hProc(TProcDialog* ptrParent)
    {
        DWORD       rtnStatus = 1;
        int                     capStatus = 0;

capStatus = ptrParent->StartCapture();

return rtnStatus;
    }

//*****************************************************************
DWORD FAR PASCAL Crunch_hProc(TProcDialog* ptrParent)
    {
        DWORD       rtnStatus = 1;

ptrParent->CrunchCapture();

return rtnStatus;
    }

//*****************************************************************
void TProcDialog::StartProcThreads()
    {
        if (NULL == (hThread_Capture =
                                    CreateThread( (LPSECURITY_ATTRIBUTES) NULL,
                                    0,
                                    (LPTHREAD_START_ROUTINE) Capture_hProc,
                                    this,
                                    0, &dwThreadID_Capture )))
            {
```

```
::MessageBox( HWindow,"Capture Thread Creation Failed.","System Error" ,
    MB_ICONEXCLAMATION | MB_OK ) ;
        CloseWindow();
        return;
        }
    else
        {
        } if (NULL == (hThread_Analyze =
                                    CreateThread( (LPSECURITY_ATTRIBUTES) NULL,
                                    0,
                                    (LPTHREAD_START_ROUTINE) Analyze_hProc,
                                    this,
                                    0, &dwThreadID_Analyze )))
        {
::MessageBox( HWindow,"Analyze Thread Creation Failed.","System Error" ,
    MB_ICONEXCLAMATION | MB_OK ) ;
        CloseWindow();
        return;
        }
    else
        {
        } if (NULL == (hThread_Crunch =
                                    CreateThread( (LPSECURITY_ATTRIBUTES) NULL,
                                    0,
                                    (LPTHREAD_START_ROUTINE) Crunch_hProc,
                                    this,
                                    0, &dwThreadID_Crunch )))
        {
::MessageBox( HWindow,"Crunch Thread Creation Failed.","System Error" ,
    MB_ICONEXCLAMATION | MB_OK ) ;
        CloseWindow();
        return;
        }
    else
        {
        }
    }
//****************************************************************************
//
//
//****************************************************************************
void TProcDialog::StopProcThreads()
    {

PostThreadMessage(dwThreadID_Analyze,WM_USER+399,0,0);

}

//****************************************************************************
//
//
//****************************************************************************
void TProcDialog::CaptureLoop()
    {
    int done_code = 0;
    MSG     proc_msg;
```

```
FrameView->SetText("Initialize");
while (done_code == 0)
        {
        GetMessage(&proc_msg,NULL,0,0);
        switch (proc_msg.message)
                {
                case WM_USER+305:   // launch a capture
                        done_code = 0;
                        FrameView->SetText("Start Frame");
                        PVision[Current_Frame] = new TVision(this,Total_Planes,ptrSysDevs);
                        if (!PVision[Current_Frame]->CaptureVision())
                                {
                                PostThreadMessage(dwThreadID_Analyze,WM_USER+345,0,0);
                                return;
                                }
                        FrameView->SetText("End Frame");
                        PostThreadMessage(dwThreadID_Analyze,WM_USER+312,0,0);
                        break;
                case WM_USER+310:       // exit, we are all done
                        FrameView->SetText("");
                        done_code = 1;
                        break;
                case WM_USER+315:       // dummy, extra to make sure every thing is clear
                        done_code = 0;
                        break;
                }
        }

}

//*********************************************************************
//
//
//*********************************************************************
void TProcDialog::CrunchCapture()
{
int done_code = 0;
MSG    proc_msg;

CompletePercent->SetText("Initialize");
while (done_code == 0)
        {
        GetMessage(&proc_msg,NULL,0,0);
        switch (proc_msg.message)
                {
                case WM_USER+335:  // launch a crunch
                        done_code = 0;
                        CompletePercent->SetText("Start Frame");
                        if (!PVision[Current_Frame]->ProcessVision())
                                {
                                PostThreadMessage(dwThreadID_Analyze,WM_USER+346,0,0);
                                return;
                                }
                        CompletePercent->SetText("End Frame");
                        break;
                case WM_USER+310:       // exit, we are all done
                        CompletePercent->SetText("");
                        done_code = 1;
                        break;
                case WM_USER+316:       // asked for status, return that we are done
                        done_code = 0;
```

```
                                PostThreadMessage(dwThreadID_Analyze,WM_USER+313,0,0);
                                break;
                    case WM_USER+315:      // dummy, extra to make sure every thing is clear
                                done_code = 0;
                                break;
                    case WM_USER+399:      // cancel all!
                                done_code = 1;
                                CompletePercent->SetText("Canceled");
                                return;
//                              break;
                    }
            }
    }

//*************************************************************************
//
//      Send and process messages for the Analyze thread
//
//*************************************************************************
int TProcDialog::AnalyzeMsg()
    {
    int done_code = 0;
    MSG     proc_msg;

//*************************************************************************
//      Tell Capture thread to start
//*************************************************************************
    PostThreadMessage(dwThreadID_Capture,WM_USER+305,0,0);

//*************************************************************************
//      Wait for message that Capture thread is done or a cancel has occurred
//*************************************************************************
    done_code = 0;
    while (done_code == 0)
            {
            GetMessage(&proc_msg,NULL,0,0);
            switch (proc_msg.message)
                    {
                    case WM_USER+312:
                                done_code = 1;
                                break;
                    case WM_USER+399:      // cancel all!
                                done_code = 1;
                                sb->SetText("Process Being Cancelled!");
                                PostThreadMessage(dwThreadID_Capture,WM_USER+399,0,0);
                                PostThreadMessage(dwThreadID_Crunch,WM_USER+399,0,0);
                                GetMessage(&proc_msg,NULL,WM_USER+345,WM_USER+346);
                                GetMessage(&proc_msg,NULL,WM_USER+345,WM_USER+346);
                                for (int g1 = 0;g1 < 10;g1++)
                                        {
                                        ControlWin->PStatDialog->SetSpectralFrame(g1,0);
                                        }
                                ControlWin->PStatDialog->GraphSpectral();
                                sb->SetText("Processing Cancelled By User!");

DeCommitMemory();

return FALSE;
//                              break;
                    }
            }
```

```
        return TRUE;
    }

//*************************************************************************
//
//
//*************************************************************************
int TProcDialog::StartCapture()
    {
        int         q;
        int         done_code = 0;
        MSG         proc_msg;
        int         firstFrame = 10;
        RECT        fillRect;
        int         isentr_x;
        int         isentr_y;

Set_Number = 0;
        Current_Frame = 0;
        sb->SetText("Processing Stone...");
        Image1->SetCursor(0,IDC_NO);
        Image2->SetCursor(0,IDC_NO);
        Image3->SetCursor(0,IDC_NO);
        ImageMain->SetCursor(0,IDC_NO);

PostThreadMessage(dwThreadID_Capture,WM_USER+315,0,0);
        PostThreadMessage(dwThreadID_Crunch,WM_USER+315,0,0);

f4_CIExData->Clear();
        f4_CIEyData->Clear();
        f4_CIEYData->Clear();
        f4_CIELData->Clear();
        f4_CIEaData->Clear();
        f4_CIEbData->Clear();
        f4_SatData->Clear();
        f4_DWLData->Clear();
        f4_ToneData->Clear();
        f4_Color->Clear();

SetCursor(0,IDC_WAIT);

SetCurrentSets();

::GetClientRect(ImageMain->HWindow,&fillRect);
        ::FillRect(winhdc,&fillRect,(HBRUSH) GetStockObject(BLACK_BRUSH));

//      ZeroMemory(&IsPoints,3*640*480);

for (q = 0;q < 3;q++)
            {

Set_Number = q;

for (isentr_y = 0; isentr_y < 480; isentr_y++)
                    {
                        for (isentr_x = 0; isentr_x < 640; isentr_x++)
                            {
                                IsPoints[Set_Number][isentr_x][isentr_y] = 0;
                            }
                    }
```

```
     if ((Set_Number != 0) && (ControlWin->PauseSets->GetCheck()) && (ControlWin->Set_States[Set_Number] !=
6))
     {
       ControlWin->ptrMainApp->EnableCtl3dAutosubclass(TRUE);
       if (::MessageBox( HWindow,"Chamber can now be opened. OK to continue.","Set Paused",
MB_ICONEXCLAMATION | MB_OKCANCEL ) == IDCANCEL)
         {
           ::PostMessage(ControlWin->HWindow,WM_USER + 201,12,12);
         }
       ControlWin->ptrMainApp->EnableCtl3dAutosubclass(FALSE);
       Sleep(500);
     } if (PeekMessage(&proc_msg,(HWND) -1,WM_USER+399,WM_USER+399,PM_REMOVE))
     {
       return FALSE;
     } if (abs(ptrSysDevs->UGTSContlr->ReadTemp() - ChamberTemp) > 1)
     {
       sb->SetText("Initializing filter, please wait...");
       ptrSysDevs->FilterDevice->Init();
       Beep(2000,1000);
       Sleep(45000);
       Beep(2000,1000);
       ChamberTemp = ptrSysDevs->UGTSContlr->ReadTemp();
     } sb->SetText("Processing Stone...");
     switch (ControlWin->Set_States[q])
     {
       case 1:
         if (Set_Number > 0) SetCurrentSets();
         switch(ControlWin->CurLightPos)
         {
           case 2:
             ptrSysDevs->MotionDevice->moMovementStep = 1;
             ptrSysDevs->MotionDevice->Move();
             Sleep(1500);
             ptrSysDevs->MotionDevice->Move();
             break;
           case 3:
             break;
           case 1:
             ptrSysDevs->MotionDevice->Home();
             Sleep(2000);
             ptrSysDevs->MotionDevice->moMovementStep = 5;
             ptrSysDevs->MotionDevice->Move();
             Sleep(1500);
             ptrSysDevs->MotionDevice->moMovementStep = 1;
             ptrSysDevs->MotionDevice->Move();
         }
         ControlWin->CurLightPos = 3;
         ControlWin->PStatDialog->LightPosition->SetText("Diffuse");
         Sleep(500);

Current_Frame = q*3;
         if (Current_Frame < firstFrame) firstFrame = Current_Frame;
         strcpy(frmData[Current_Frame]->title,"Frame 1 :: Diffuse");
         fl_Title->SetText(frmData[Current_Frame]->title);
         if (!AnalyzeMsg()) return FALSE;
```

```
            break;
case 2:
        if (Set_Number > 0) SetCurrentSets();
        switch(ControlWin->CurLightPos)
                {
                case 1:
                        ptrSysDevs->MotionDevice->moMovementStep = 5;
                        ptrSysDevs->MotionDevice->Move();
                        Sleep(1500);
                        break;
                case 2:
                        break;
                case 3:
                        ptrSysDevs->MotionDevice->Home();
                        Sleep(3000);
                        ptrSysDevs->MotionDevice->moMovementStep = 5;
                        ptrSysDevs->MotionDevice->Move();
                        Sleep(1500);
                }
        ControlWin->CurLightPos = 2;
        ControlWin->PStatDialog->LightPosition->SetText("Suffuse");
        Sleep(500);

Current_Frame = q*3;
        if (Current_Frame < firstFrame) firstFrame = Current_Frame;
        strcpy(frmData[Current_Frame]->title,"Frame 1 :: Suffuse");
        fl_Title->SetText(frmData[Current_Frame]->title);
        if (!AnalyzeMsg()) return FALSE;
        break;
case 3:
        if (Set_Number > 0) SetCurrentSets();
        ptrSysDevs->MotionDevice->Home();
        Sleep(2000);
        ControlWin->CurLightPos = 1;
        ControlWin->PStatDialog->LightPosition->SetText("Reflect");
        Sleep(500);

Current_Frame = q*3;
        if (Current_Frame < firstFrame) firstFrame = Current_Frame;
        strcpy(frmData[Current_Frame]->title,"Frame 1 :: Reflectance");
        fl_Title->SetText(frmData[Current_Frame]->title);
        if (!AnalyzeMsg()) return FALSE;
        break;
case 0:
        if (Set_Number > 0) SetCurrentSets();
        ptrSysDevs->MotionDevice->Home();
        Sleep(3000);
        ControlWin->CurLightPos = 1;
        ControlWin->PStatDialog->LightPosition->SetText("Reflect");

Current_Frame = q*3;
        if (Current_Frame < firstFrame) firstFrame = Current_Frame;
        strcpy(frmData[Current_Frame]->title,"Frame 1 :: Reflectance");
        fl_Title->SetText(frmData[Current_Frame]->title);
        if (!AnalyzeMsg()) return FALSE;

ptrSysDevs->MotionDevice->moMovementStep = 5;
        ptrSysDevs->MotionDevice->Move();
        Sleep(1500);
        ControlWin->CurLightPos = 2;
        ControlWin->PStatDialog->LightPosition->SetText("Suffuse");
```

```
                Current_Frame = q*3+1;
                if (Current_Frame < firstFrame) firstFrame = Current_Frame;
                strcpy(frmData[Current_Frame]->title,"Frame 2 :: Suffuse");
                f2_Title->SetText(frmData[Current_Frame]->title);
                if (!AnalyzeMsg()) return FALSE;

ptrSysDevs->MotionDevice->moMovementStep = 1;
                ptrSysDevs->MotionDevice->Move();
                ControlWin->CurLightPos = 3;
                ControlWin->PStatDialog->LightPosition->SetText("Diffuse");

Current_Frame = q*3+2;
                if (Current_Frame < firstFrame) firstFrame = Current_Frame;
                strcpy(frmData[Current_Frame]->title,"Frame 3 :: Diffuse");
                f3_Title->SetText(frmData[Current_Frame]->title);
                if (!AnalyzeMsg()) return FALSE;

//                     ::MessageBox(HWindow,"Paused for calculations.","System Message."
//                                                         ,MB_OK | MB_ICONEXCLAMATION |
MB_TASKMODAL);

if (ControlWin->EnableSep->GetCheck())
                        {
                        SetCursor(0,IDC_WAIT);
                        PVision[Current_Frame-2]->ReProcessVision(0);
                        PVision[Current_Frame-1]->ReProcessVision(0);
                        SetCursor(0,IDC_ARROW);
                        } break;
        case 4:
                if (Set_Number > 0) SetCurrentSets();
                break;
        case 5:
                if (Set_Number > 0) SetCurrentSets();
                break;
        case 6:
                break;
        }

// ask crunch if finish, if not wait for it
                PostThreadMessage(dwThreadID_Crunch,WM_USER+316,0,0);
                done_code = 0;
                while (done_code == 0)
                        {
                        GetMessage(&proc_msg,NULL,0,0);
                        if (proc_msg.message == WM_USER+313) done_code = 1;
                        }

}

//      PostThreadMessage(dwThreadID_Crunch,WM_USER+316,0,0);
//      done_code = 0;
//      while (done_code == 0)
//              {
//              GetMessage(&proc_msg,NULL,0,0);
//              if (proc_msg.message == WM_USER+313) done_code = 1;
//              }

// tell threads that we are all done
```

```
        PostThreadMessage(dwThreadID_Capture,WM_USER-310,0,0);
        PostThreadMessage(dwThreadID_Crunch,WM_USER-310,0,0);

ptrSysDevs->MotionDevice->Home();
        Set_Number = 0;
        SetCurrentSets();

LightA->EnableWindow(1);
        LightB->EnableWindow(1);
        LightC->EnableWindow(1);
        LightD->EnableWindow(1);
        Std1964->EnableWindow(1);
        Std1931->EnableWindow(1);
        SetBtn1->EnableWindow(1);
        SetBtn2->EnableWindow(1);
        SetBtn3->EnableWindow(1);

Single->EnableWindow(1);
        Construct->EnableWindow(1);
        HueGraph->EnableWindow(1);
        ToneGraph->EnableWindow(1);
        xyYGraph->EnableWindow(1);
        LabGraph->EnableWindow(1);
        uvGraph->EnableWindow(1);
        MoreGraph->EnableWindow(1);
        SaveBtn->EnableWindow(1);
        CloseBtn->EnableWindow(1);

Current_Frame = firstFrame;

// tell capture dialog that all is done
        ::PostMessage(ControlWin->HWindow,WM_USER + 200,12,12);
        sb->SetText("Processing completed.");
        SetCursor(0,IDC_ARROW);

return TRUE;

}

//*********************************************************************
void TProcDialog::EvPaint()
        {
        RECT            objRect;

::GetWindowRect(HWindow,&objRect);
        objRect.right = objRect.right - objRect.left;
        objRect.bottom = objRect.bottom - objRect.top;
        objRect.left = 0;
        objRect.top = 0;

BeginPaint(HWindow,&ps);
        if ((ps.rcPaint.left == 0) && (ps.rcPaint.top == 0) && (ps.rcPaint.right < objRect.right-10) && (ps.rcPaint.bottom <
objRect.bottom-10))
                {

}
        else
                {
                objRect.left = 0;
                objRect.top = 0;
                objRect.right = objRect.right - 25;
```

```
objRect.bottom = objRect.bottom - 25;
::InvalidateRect(HWindow,&objRect,FALSE);

::InvalidateRect(LightGroup->HWindow,NULL,FALSE);
::InvalidateRect(StdGroup->HWindow,NULL,FALSE);
::InvalidateRect(SetGroup->HWindow,NULL,FALSE);
::InvalidateRect(LightA->HWindow,NULL,FALSE);
::InvalidateRect(LightB->HWindow,NULL,FALSE);
::InvalidateRect(LightC->HWindow,NULL,FALSE);
::InvalidateRect(LightD->HWindow,NULL,FALSE);
::InvalidateRect(Std1964->HWindow,NULL,FALSE);
::InvalidateRect(Std1931->HWindow,NULL,FALSE);
::InvalidateRect(SetBtn1->HWindow,NULL,FALSE);
::InvalidateRect(SetBtn2->HWindow,NULL,FALSE);
::InvalidateRect(SetBtn3->HWindow,NULL,FALSE);

::InvalidateRect(f1_CIExData->HWindow,NULL,FALSE);
::InvalidateRect(f2_CIExData->HWindow,NULL,FALSE);
::InvalidateRect(f3_CIExData->HWindow,NULL,FALSE);
::InvalidateRect(f4_CIExData->HWindow,NULL,FALSE);

::InvalidateRect(f1_CIEyData->HWindow,NULL,FALSE);
::InvalidateRect(f2_CIEyData->HWindow,NULL,FALSE);
::InvalidateRect(f3_CIEyData->HWindow,NULL,FALSE);
::InvalidateRect(f4_CIEyData->HWindow,NULL,FALSE);

::InvalidateRect(f1_CIEYData->HWindow,NULL,FALSE);
::InvalidateRect(f2_CIEYData->HWindow,NULL,FALSE);
::InvalidateRect(f3_CIEYData->HWindow,NULL,FALSE);
::InvalidateRect(f4_CIEYData->HWindow,NULL,FALSE);

::InvalidateRect(f1_CIELData->HWindow,NULL,FALSE);
::InvalidateRect(f2_CIELData->HWindow,NULL,FALSE);
::InvalidateRect(f3_CIELData->HWindow,NULL,FALSE);
::InvalidateRect(f4_CIELData->HWindow,NULL,FALSE);

::InvalidateRect(f1_CIEaData->HWindow,NULL,FALSE);
::InvalidateRect(f2_CIEaData->HWindow,NULL,FALSE);
::InvalidateRect(f3_CIEaData->HWindow,NULL,FALSE);
::InvalidateRect(f4_CIEaData->HWindow,NULL,FALSE);

::InvalidateRect(f1_CIEbData->HWindow,NULL,FALSE);
::InvalidateRect(f2_CIEbData->HWindow,NULL,FALSE);
::InvalidateRect(f3_CIEbData->HWindow,NULL,FALSE);
::InvalidateRect(f4_CIEbData->HWindow,NULL,FALSE);

::InvalidateRect(f1_DWLData->HWindow,NULL,FALSE);
::InvalidateRect(f2_DWLData->HWindow,NULL,FALSE);
::InvalidateRect(f3_DWLData->HWindow,NULL,FALSE);
::InvalidateRect(f4_DWLData->HWindow,NULL,FALSE);

::InvalidateRect(f1_SatData->HWindow,NULL,FALSE);
::InvalidateRect(f2_SatData->HWindow,NULL,FALSE);
::InvalidateRect(f3_SatData->HWindow,NULL,FALSE);
::InvalidateRect(f4_SatData->HWindow,NULL,FALSE);

::InvalidateRect(f1_ToneData->HWindow,NULL,FALSE);
::InvalidateRect(f2_ToneData->HWindow,NULL,FALSE);
::InvalidateRect(f3_ToneData->HWindow,NULL,FALSE);
::InvalidateRect(f4_ToneData->HWindow,NULL,FALSE);
```

```
                    ::InvalidateRect(f1_Color->HWindow,NULL,FALSE);
                    ::InvalidateRect(f2_Color->HWindow,NULL,FALSE);
                    ::InvalidateRect(f3_Color->HWindow,NULL,FALSE);
                    ::InvalidateRect(f4_Color->HWindow,NULL,FALSE);

::UpdateWindow(HWindow);
                    RePaint();

}

EndPaint(HWindow,&ps);

}

//*************************************************************************
void TProcDialog::EvMove(TPoint &clientOrigin)
        {

::SetWindowPos(HWindow,0, 0,230,1016,440,SWP_NOZORDER);

}

//*************************************************************************
BOOL TProcDialog::EvEraseBkgnd(HDC painthdc)
        {
        RECT            fillRect;
        HDC             fillhdc;

fillhdc = GetDC(HWindow);
        fillRect.left = 0;
        fillRect.top = 0;
        fillRect.right = 1024;
        fillRect.bottom = 550;
        ::FillRect(fillhdc,&fillRect,(HBRUSH) GetStockObject(LTGRAY_BRUSH));
        ReleaseDC(HWindow,fillhdc);

fillhdc = GetDC(SetGroup->HWindow);
        fillRect.left = 0;
        fillRect.top = 0;
        fillRect.right = 68;
        fillRect.bottom = 95;
        ::FillRect(fillhdc,&fillRect,(HBRUSH) GetStockObject(LTGRAY_BRUSH));
        ReleaseDC(SetGroup->HWindow,fillhdc);

fillhdc = GetDC(StdGroup->HWindow);
        fillRect.left = 0;
        fillRect.top = 0;
        fillRect.right = 69;
        fillRect.bottom = 87;
        ::FillRect(fillhdc,&fillRect,(HBRUSH) GetStockObject(LTGRAY_BRUSH));
        ReleaseDC(StdGroup->HWindow,fillhdc);

fillhdc = GetDC(LightGroup->HWindow);
        fillRect.left = 0;
        fillRect.top = 0;
        fillRect.right = 69;
        fillRect.bottom = 121;
        ::FillRect(fillhdc,&fillRect,(HBRUSH) GetStockObject(LTGRAY_BRUSH));
        ReleaseDC(LightGroup->HWindow,fillhdc);

return 0;
```

```
        }
//*************************************************************************
void TProcDialog::EvActivate(UINT active,BOOL minimized,HWND hWndOther)

{ if (active != WA_INACTIVE)
                {
                RePaint();
                }

}

//*************************************************************************
void TProcDialog::SetCurrentSets()
        {
        char            mbuf[10];
        int             i1;
        RECT            fillRect;
        HDC                     fillhdc;

fillhdc = GetDC(Image1->HWindow);
        ::GetClientRect(Image1->HWindow,&fillRect);
        ::FillRect(fillhdc,&fillRect,(HBRUSH) GetStockObject(BLACK_BRUSH));
        ReleaseDC(Image1->HWindow,fillhdc);

fillhdc = GetDC(Image2->HWindow);
        ::GetClientRect(Image2->HWindow,&fillRect);
        ::FillRect(fillhdc,&fillRect,(HBRUSH) GetStockObject(BLACK_BRUSH));
        ReleaseDC(Image2->HWindow,fillhdc);

fillhdc = GetDC(Image3->HWindow);
        ::GetClientRect(Image3->HWindow,&fillRect);
        ::FillRect(fillhdc,&fillRect,(HBRUSH) GetStockObject(BLACK_BRUSH));
        ReleaseDC(Image3->HWindow,fillhdc);

fillhdc = GetDC(f1_Title->HWindow);
        ::GetClientRect(f1_Title->HWindow,&fillRect);
        ::FillRect(fillhdc,&fillRect,(HBRUSH) GetStockObject(BLACK_BRUSH));
        ReleaseDC(f1_Title->HWindow,fillhdc);

fillhdc = GetDC(f2_Title->HWindow);
        ::GetClientRect(f2_Title->HWindow,&fillRect);
        ::FillRect(fillhdc,&fillRect,(HBRUSH) GetStockObject(BLACK_BRUSH));
        ReleaseDC(f2_Title->HWindow,fillhdc);

fillhdc = GetDC(f3_Title->HWindow);
        ::GetClientRect(f3_Title->HWindow,&fillRect);
        ::FillRect(fillhdc,&fillRect,(HBRUSH) GetStockObject(BLACK_BRUSH));
        ReleaseDC(f3_Title->HWindow,fillhdc);

f1_CIExData->Clear();
        f2_CIExData->Clear();
        f3_CIExData->Clear();

f1_CIEyData->Clear();
        f2_CIEyData->Clear();
        f3_CIEyData->Clear();

f1_CIEYData->Clear();
        f2_CIEYData->Clear();
```

```
f3_CIEYData->Clear();

f1_CIELData->Clear();
f2_CIELData->Clear();
f3_CIELData->Clear();

f1_CIEaData->Clear();
f2_CIEaData->Clear();
f3_CIEaData->Clear();

f1_CIEbData->Clear();
f2_CIEbData->Clear();
f3_CIEbData->Clear();

f1_SatData->Clear();
f2_SatData->Clear();
f3_SatData->Clear();

f1_DWLData->Clear();
f2_DWLData->Clear();
f3_DWLData->Clear();

f1_ToneData->Clear();
f2_ToneData->Clear();
f3_ToneData->Clear();

f1_Color->Clear();
f2_Color->Clear();
f3_Color->Clear();

SetBtn1->Uncheck();
SetBtn2->Uncheck();
SetBtn3->Uncheck();

for (i1 = 0;i1 < 10;i1++)
        {
        ControlWin->PStatDialog->SetSpectralFrame(i1,0);
        }

Image1->SetCursor(0,IDC_NO);
Image2->SetCursor(0,IDC_NO);
Image3->SetCursor(0,IDC_NO);
ImageMain->SetCursor(0,IDC_NO);

switch (Set_Number)
        {
        case 0:
                SetBtn1->Check();
                for (i1 = 0;i1 < 3;i1++)
                        {
                        if (PVision[i1] != NULL)
                                {
                                PVision[i1]->PaintImage();
                                PVision[i1]->ShowData();
                                ControlWin->PStatDialog->SetSpectralFrame(i1,1);
                                }
                        switch (i1)
                                {
                                case 0:
                                        if (PVision[i1] == NULL) strcpy(frmData[i1]->title,"Frame 1 :: Empty");
                                        if (PVision[i1] != NULL) Image1->SetCursor(0,IDC_ARROW);
```

```
                                        f1_Title->SetText(frmData[i1]->title);
                                        break;
                                case 1:
                                        if (PVision[i1] == NULL) strcpy(frmData[i1]->title,"Frame 2 :: Empty");
                                        if (PVision[i1] != NULL) Image2->SetCursor(0,IDC_ARROW);
                                        f2_Title->SetText(frmData[i1]->title);
                                        break;
                                case 2:
                                        if (PVision[i1] == NULL) strcpy(frmData[i1]->title,"Frame 3 :: Empty");
                                        if (PVision[i1] != NULL) Image3->SetCursor(0,IDC_ARROW);
                                        f3_Title->SetText(frmData[i1]->title);
                                        break;
                                }

}
                break;
        case 1:
                SetBtn2->Check();
                for (i1 = 3;i1 < 6;i1++)
                        {
                        if (PVision[i1] != NULL)
                                {
                                PVision[i1]->PaintImage();
                                PVision[i1]->ShowData();
                                ControlWin->PStatDialog->SetSpectralFrame(i1,1);
                                } switch (i1)
                                {
                                case 3:
                                        if (PVision[i1] == NULL) strcpy(frmData[i1]->title,"Frame 1 :: Empty");
                                        if (PVision[i1] != NULL) Image1->SetCursor(0,IDC_ARROW);
                                        f1_Title->SetText(frmData[i1]->title);
                                        break;
                                case 4:
                                        if (PVision[i1] == NULL) strcpy(frmData[i1]->title,"Frame 2 :: Empty");
                                        if (PVision[i1] != NULL) Image2->SetCursor(0,IDC_ARROW);
                                        f2_Title->SetText(frmData[i1]->title);
                                        break;
                                case 5:
                                        if (PVision[i1] == NULL) strcpy(frmData[i1]->title,"Frame 3 :: Empty");
                                        if (PVision[i1] != NULL) Image3->SetCursor(0,IDC_ARROW);
                                        f3_Title->SetText(frmData[i1]->title);
                                        break;
                                }

}
                break;
        case 2:
                SetBtn3->Check();
                for (i1 = 6;i1 < 9;i1++)
                        {
                        if (PVision[i1] != NULL)
                                {
                                PVision[i1]->PaintImage();
                                PVision[i1]->ShowData();
                                ControlWin->PStatDialog->SetSpectralFrame(i1,1);
                                } switch (i1)
                                {
                                case 6:
```

```
                                    if (PVision[i1] == NULL) strcpy(frmData[i1]->title,"Frame 1 :: Empty");
                                    if (PVision[i1] != NULL) Image1->SetCursor(0,IDC_ARROW);
                                    f1_Title->SetText(frmData[i1]->title);
                                    break;
                        case 7:
                                    if (PVision[i1] == NULL) strcpy(frmData[i1]->title,"Frame 2 :: Empty");
                                    if (PVision[i1] != NULL) Image2->SetCursor(0,IDC_ARROW);
                                    f2_Title->SetText(frmData[i1]->title);
                                    break;
                        case 8:
                                    if (PVision[i1] == NULL) strcpy(frmData[i1]->title,"Frame 3 :: Empty");
                                    if (PVision[i1] != NULL) Image3->SetCursor(0,IDC_ARROW);
                                    f3_Title->SetText(frmData[i1]->title);
                                    break;
                        }
                  }
                  break;
            }

ControlWin->PStatDialog->GraphSpectral();

}

//**************************************************************************
void TProcDialog::GetCurrentSets()
      {

}

//**************************************************************************
void TProcDialog::SetSet1()
      {

GetCurrentSets();
            Set_Number = 0;
            SetCurrentSets();

}

//**************************************************************************
void TProcDialog::SetSet2()
      {

GetCurrentSets();
            Set_Number = 1;
            SetCurrentSets();

}

//**************************************************************************
void TProcDialog::SetSet3()
      {

GetCurrentSets();
            Set_Number = 2;
            SetCurrentSets();

}

//**************************************************************************
void TProcDialog::SetImage1()
```

```
       {
       int     yo = 0;

CloseBtn->SetFocus();
       switch (Set_Number)
               {
               case 0:
                       if (PVision[0] != NULL)
                               {
                               Current_Frame = 0;
                               yo = 1;
                               }
                       break;
               case 1:
                       if (PVision[3] != NULL)
                               {
                               Current_Frame = 3;
                               yo = 1;
                               }
                       break;
               case 2:
                       if (PVision[6] != NULL)
                               {
                               Current_Frame = 6;
                               yo = 1;
                               }
                       break;
               } if (yo == 1)
               {
               PVision[Current_Frame]->PaintImage();
               PVision[Current_Frame]->LargeImage();
               }
       else
               {
               Beep(2000,500);
               }

}
//******************************************************************************
void TProcDialog::SetImage2()
       {
       int     yo = 0;

CloseBtn->SetFocus();
       switch (Set_Number)
               {
               case 0:
                       if (PVision[1] != NULL)
                               {
                               Current_Frame = 1;
                               yo = 1;
                               }
                       break;
               case 1:
                       if (PVision[4] != NULL)
                               {
                               Current_Frame = 4;
                               yo = 1;
                               }
```

```
                        break;
                case 2:
                        if (PVision[7] != NULL)
                                {
                                Current_Frame = 7;
                                yo = 1;
                                }
                        break;
                }
        if (yo == 1)
                {
                PVision[Current_Frame]->PaintImage();
                PVision[Current_Frame]->LargeImage();
                }
        else
                {
                Beep(2000,500);
                }

}

//*****************************************************************************
void TProcDialog::SetImage3()
        {
        int     yo = 0;

CloseBtn->SetFocus();
        switch (Set_Number)
                {
                case 0:
                        if (PVision[2] != NULL)
                                {
                                Current_Frame = 2;
                                yo = 1;
                                }
                        break;
                case 1:
                        if (PVision[5] != NULL)
                                {
                                Current_Frame = 5;
                                yo = 1;
                                }
                        break;
                case 2:
                        if (PVision[8] != NULL)
                                {
                                Current_Frame = 8;
                                yo = 1;
                                }
                        break;
                } if (yo == 1)
                {
                PVision[Current_Frame]->PaintImage();
                PVision[Current_Frame]->LargeImage();
                }
        else
                {
                Beep(2000,500);
                }
```

}

//****************************************************************************
//
// Graph cie horseshoe and data points.
//
//****************************************************************************
void TProcDialog::GraphCIExyY()
        {
        POINT    poly[4];
        POINT    tic_points[2];
        POINT    cie_points[322];
        LPPOINT  Poly_points;
        int      i;
        COLORREF crColor;
        int      x, y;
        HRGN     Poly_rgn;
        HPEN                   penOld;
        RECT                   fillRect;

HDC                    hDC;
        int                    stepSize = 30;

hDC = GetDC(ImageMain->HWindow);

penOld = (HPEN) SelectObject(hDC,penGreen);

poly[0].x = 18;
        poly[0].y = 17;

poly[1].x = 18;
        poly[1].y = 317;

poly[2].x = 318;
        poly[2].y = 317;

poly[3].x = 318;
        poly[3].y = 17;

::GetClientRect(ImageMain->HWindow,&fillRect);
        ::FillRect(winhdc,&fillRect,(HBRUSH) GetStockObject(BLACK_BRUSH));

TPaint_TextRecs(hDC,200,10,120,28,6,TA_CENTER,0,18,"CIE 1931 xyY",700,2);

TPaint_TextRecs(hDC,6,10,10,20,0,TA_LEFT,6,12,"1",700,0);

TPaint_TextRecs(hDC,6,310,10,20,0,TA_LEFT,6,12,"0",700,0);

TPaint_TextRecs(hDC,320,320,12,12,0,TA_LEFT,6,12,"1",700,0);

Poly_points = poly;
        Polyline(hDC,Poly_points,3);

for (i = 0; i < 10; i++)
                {
                tic_points[0].x = poly[0].x;
                tic_points[0].y = poly[0].y + i*stepSize;
                tic_points[1].x = poly[0].x - 5;
                tic_points[1].y = poly[0].y + i*stepSize;

```
                    Poly_points = tic_points;
                    Polyline(hDC,Poly_points,2);
                    } for (i = 0; i < 10; i++)
                    {
                    tic_points[0].y = poly[1].y;
                    tic_points[0].x = poly[1].x + i*stepSize + stepSize;
                    tic_points[1].y = poly[1].y + 5;
                    tic_points[1].x = poly[1].x + i*stepSize + stepSize;
                    Poly_points = tic_points;
                    Polyline(hDC,Poly_points,2);
                    } for (i = 0; i <321; i++)
                    {
                    cie_points[i].x = 300*(cie_locus[i].fx) + poly[1].x;
                    cie_points[i].y = 300*(1 - cie_locus[i].fy) + poly[0].y;
                    } cie_points[321].x = 300*(cie_locus[0].fx) + poly[1].x;
       cie_points[321].y = 300*(1 - cie_locus[0].fy) + poly[0].y;

Poly_points = cie_points;
       Polyline(hDC,Poly_points,322);

SelectObject(hDC,penOld);
       ReleaseDC(ImageMain->HWindow,hDC);

PVision[Current_Frame]->GraphPoints_xy();

}

//*****************************************************************
//
// Request a reprocess.
//
//*****************************************************************
void TProcDialog::ReProcess()
       {

SetCursor(0,IDC_WAIT);
       PVision[Current_Frame]->ReProcessVision(0);
       SetCursor(0,IDC_ARROW);

}

//*****************************************************************
//
// Build and process a construct.
//
//*****************************************************************
void TProcDialog::StartConstruct()
       {
       int     cntr;
       int     first = 0;

SetCursor(0,IDC_WAIT);

for (cntr = 0; cntr < 9; cntr++)
              {
```

```
                if (PVision[cntr] != NULL)
                        {
                        if (PVision[cntr]->ConstructMe)
                                {
                                first = first + 1;
                                PVision[cntr]->Construct(ptrConstructIMG, first);
                                }
                        }
                }

PVision[Current_Frame]->ConstructCalc(ptrConstructBMP,ptrConstructIMG,ptrConstructXYZ,ptrConstructRGB,0);
        SetCursor(0,IDC_ARROW);

}

//**********************************************************************
//
// Save group.
//
//**********************************************************************
void TProcDialog::SaveGroup()
        {
        int                     cntr;
        int                     first = 0;
        char            tbuff[100];
        char            cbuff[100];
        HANDLE     TempFile;
        DWORD                   rtnBytes;
        LPSTR                   FileName = tbuff;
        LPSTR                   Name = cbuff;

SetCursor(0,IDC_WAIT);

strcpy(FileName,"c:\\egldata\\");
        ControlWin->IDValue->GetText(Name,99);
        strcat(FileName,Name);

TempFile =
CreateFile(FileName,GENERIC_WRITE,0,NULL,CREATE_ALWAYS,FILE_ATTRIBUTE_NORMAL,NULL);
        if (TempFile == INVALID_HANDLE_VALUE)
                {
   ::MessageBox( GetActiveWindow(),"Unable to open Calibration file!.","System Error." ,
                MB_ICONEXCLAMATION | MB_OK );
                return;
                } for (cntr = 0; cntr < 9; cntr++)
                {
                if (PVision[cntr] != NULL)
                        {
                        first = first + 1;
                        PVision[cntr]->SaveFrame(TempFile, first);
                        }
                }

CloseHandle(TempFile);

SetCursor(0,IDC_ARROW);

}
```

```
//****************************************************************
//
// Left mouse button down.
//
//****************************************************************
void TProcDialog::EvLButtonDown(UINT modkeys, TPoint & point)
    {
    RECT            objRect;
    RECT            winRect;

::GetWindowRect(HWindow,&winRect);
    ::GetWindowRect(ImageMain->HWindow,&objRect);

if (((point.x - (objRect.left - winRect.left) + 6) < 0) || ((point.y - (objRect.top - winRect.top) + 24) < 0))
        {
        lmButtonDown = 0;
        return;
        } if (((point.x - (objRect.left - winRect.left) + 6) > (objRect.right-objRect.left)) || ((point.y - (objRect.top - winRect.top) + 24) >
(objRect.bottom-objRect.top)))
        {
        lmButtonDown = 0;
        return;
        } lmButtonDown = 1;

startPoint->x = point.x - (objRect.left - winRect.left) + 6;
    startPoint->y = point.y - (objRect.top - winRect.top) + 24;
    endPoint->x = point.x - (objRect.left - winRect.left) + 6;
    endPoint->y = point.y - (objRect.top - winRect.top) + 24;

oldROPmode = SetROP2(winhdc,R2_NOT);

}

//****************************************************************
//
// Left mouse button up.
//
//****************************************************************
void TProcDialog::EvLButtonUp(UINT modkeys, TPoint & point)
    {
    POINT    poly[5];
    LPPOINT  Poly_points;
    RECT            objRect;
    RECT            winRect;

lmButtonDown = 0;

::GetWindowRect(HWindow,&winRect);
    ::GetWindowRect(ImageMain->HWindow,&objRect);
```

```
         if (((point.x - (objRect.left - winRect.left) + 6) < startPoint->x) || ((point.y - (objRect.top - winRect.top) + 24) < startPoint-
>y))
                {
                return;
                } if (((point.x - (objRect.left - winRect.left) + 6) > (objRect.right-objRect.left)) || ((point.y - (objRect.top - winRect.top) + 24) >
(objRect.bottom-objRect.top)))
                {
                lmButtonDown = 0;
                return;
                } endPoint->x = point.x - (objRect.left - winRect.left) + 6;
         endPoint->y = point.y - (objRect.top - winRect.top) + 24;

poly[0].x = startPoint->x;
         poly[0].y = startPoint->y;
         poly[1].x = startPoint->x;
         poly[1].y = endPoint->y;
         poly[2].x = endPoint->x;
         poly[2].y = endPoint->y;
         poly[3].x = endPoint->x;
         poly[3].y = startPoint->y;
         poly[4].x = startPoint->x;
         poly[4].y = startPoint->y;

Poly_points = poly;

Polyline(winhdc,Poly_points,5);

SetROP2(winhdc,oldROPmode);

SetCursor(0,IDC_WAIT);
         PVision[Current_Frame]->ReProcessVision(1);
         SetCursor(0,IDC_ARROW);

}

//*****************************************************************************
//
// Mouse button move.
//
//*****************************************************************************
void TProcDialog::EvMouseMove(UINT modkeys, TPoint & point)
         {
         POINT     poly[5];
         LPPOINT   Poly_points;
         RECT              objRect;
         RECT              winRect;

::GetWindowRect(HWindow,&winRect);
         ::GetWindowRect(ImageMain->HWindow,&objRect);

if (lmButtonDown == 1)
                {
                poly[0].x = startPoint->x;
                poly[0].y = startPoint->y;
                poly[1].x = startPoint->x;
                poly[1].y = endPoint->y;
                poly[2].x = endPoint->x;
```

```
                poly[2].y = endPoint->y;
                poly[3].x = endPoint->x;
                poly[3].y = startPoint->y;
                poly[4].x = startPoint->x;
                poly[4].y = startPoint->y;

Poly_points = poly;

Polyline(winhdc,Poly_points,5);

if (((point.x - (objRect.left - winRect.left) + 6) < startPoint->x) || ((point.y - (objRect.top - winRect.top) + 24) <
startPoint->y))
                        {
                        return;
                        } if (((point.x - (objRect.left - winRect.left) + 6) > (objRect.right-objRect.left)) || ((point.y - (objRect.top -
winRect.top) + 24) > (objRect.bottom-objRect.top)))
                        {
                        lmButtonDown = 0;
                        return;
                        } endPoint->x = point.x - (objRect.left - winRect.left) + 6;
                endPoint->y = point.y - (objRect.top - winRect.top) + 24;

poly[0].x = startPoint->x;
                poly[0].y = startPoint->y;
                poly[1].x = startPoint->x;
                poly[1].y = endPoint->y;
                poly[2].x = endPoint->x;
                poly[2].y = endPoint->y;
                poly[3].x = endPoint->x;
                poly[3].y = startPoint->y;
                poly[4].x = startPoint->x;
                poly[4].y = startPoint->y;

Poly_points = poly;

Polyline(winhdc,Poly_points,5);

}

}

//*********************************************************************
//
// Graph cie lab and data points.
//
//*********************************************************************
void TProcDialog::GraphCIELab()
        {
//      long    li;

POINT   poly[4];
        POINT   tic_points[2];
        POINT   cie_points[322];
        LPPOINT Poly_points;
        int     i;
        COLORREF crColor;
```

```
int      x, y;
HRGN     Poly_rgn;
HPEN                 penOld;
RECT                 fillRect;

HDC                        hDC;
int                        stepSize = 30;

hDC = GetDC(ImageMain->HWindow);

penOld = (HPEN) SelectObject(hDC,penGreen);

poly[0].x = 18;
poly[0].y = 17;

poly[1].x = 18;
poly[1].y = 317;

poly[2].x = 318;
poly[2].y = 317;

poly[3].x = 318;
poly[3].y = 17;

::GetClientRect(ImageMain->HWindow,&fillRect);
::FillRect(hDC,&fillRect,(HBRUSH) GetStockObject(BLACK_BRUSH));

TPaint_TextRecs(hDC,185,10,140,28,6,TA_CENTER,0,18,"CIE 1976 L*a*b*",700,2);

TPaint_TextRecs(hDC,7,165,20,20,0,TA_LEFT,6,12,"-a",700,0);
TPaint_TextRecs(hDC,315,165,20,20,0,TA_LEFT,6,12,"+a",700,0);

TPaint_TextRecs(hDC,165,5,20,20,0,TA_LEFT,6,12,"+b",700,0);
TPaint_TextRecs(hDC,165,313,20,20,0,TA_LEFT,6,12,"-b",700,0);

tic_points[0].x = poly[0].x + 150;
tic_points[0].y = poly[0].y;
tic_points[1].x = poly[0].x + 150;
tic_points[1].y = poly[0].y + 300;
Poly_points = tic_points;
Polyline(hDC,Poly_points,2);

tic_points[0].x = poly[0].x;
tic_points[0].y = poly[0].y + 150;
tic_points[1].x = poly[0].x + 300;
tic_points[1].y = poly[0].y + 150;
Poly_points = tic_points;
Polyline(hDC,Poly_points,2);

for (i = 1; i < 30; i++)
        {
        tic_points[0].x = poly[0].x + 148;
        tic_points[0].y = poly[0].y + i*10;
        tic_points[1].x = poly[0].x + 152;
        tic_points[1].y = poly[0].y + i*10;
        Poly_points = tic_points;
        Polyline(hDC,Poly_points,2);
        } for (i = 1; i < 30; i++)
        {
        tic_points[0].y = poly[1].y - 148;
```

```
            tic_points[0].x = poly[1].x + i*10;
            tic_points[1].y = poly[1].y - 152;
            tic_points[1].x = poly[1].x + i*10;
            Poly_points = tic_points;
            Polyline(hDC,Poly_points,2);
            }

SelectObject(hDC,penOld);
        ReleaseDC(ImageMain->HWindow,hDC);

PVision[Current_Frame]->GraphPoints_Lab();

}

//*****************************************************************
LRESULT TProcDialog::CalLighting(WPARAM,LPARAM)
        {

PVision[0] = new TVision(this,Total_Planes,ptrSysDevs);

ptrSysDevs->MotionDevice->Home();
        Sleep(4000);

ControlWin->CurLightPos = 1;
        ControlWin->PStatDialog->LightPosition->SetText("Reflect");
        PVision[0]->CalLight();

ptrSysDevs->MotionDevice->moMovementStep = 5;
        ptrSysDevs->MotionDevice->Move();
        Sleep(2000);

ControlWin->CurLightPos = 2;
        ControlWin->PStatDialog->LightPosition->SetText("Suffuse");
        PVision[0]->CalLight();

ptrSysDevs->MotionDevice->moMovementStep = 1;
        ptrSysDevs->MotionDevice->Move();
        Sleep(1000);

ControlWin->CurLightPos = 3;
        ControlWin->PStatDialog->LightPosition->SetText("Diffuse");
        PVision[0]->CalLight();

delete PVision[0];

return TRUE;

}

//*****************************************************************
LRESULT TProcDialog::CalBacking(WPARAM,LPARAM)
        {

StartProcMsg(0,0);

return TRUE;

}

//*****************************************************************
PrintGemSpec::PrintGemSpec(const char* title,TWindow* window) : TPrintout(title)
        {
```

```
        ProcWindow = window;

}

//****************************************************************
void PrintGemSpec::PrintPage(int page, TRect& rect, unsigned flags)
    {

::MessageBox(GetActiveWindow(),"In page.","System Error.",
                MB_ICONEXCLAMATION | MB_OK );

DC->DrawText("Here we go",-1,rect);

}

//****************************************************************
LRESULT TProcDialog::PrintCert(WPARAM,LPARAM)
    {

//  ControlWin->ptrMainApp->EnableCtl3dAutosubclass(TRUE);

PrintGemSpec PrintRpt("John is back!",this);
        PrintRpt.SetBanding(TRUE);
        Printer->Print(this,PrintRpt,FALSE);

//      Printer->Print(PrintRpt->ProcWindow,*PrintRpt,TRUE);
//      Printer->Print(PrintGemSpec->ProcWindow,*PrintRpt,TRUE);

return TRUE;

}

//****************************************************************
void PrintGemSpec::GetDialogInfo(int& minPage, int& maxPage,int& selFromPage, int& selToPage)
    {
 minPage = 0;
 maxPage = 0;
 selFromPage = selToPage = 0;
    }
```

```
/*
//*******************************************************************
//
// Make Paper.
//
//*******************************************************************
        void TCertDsgnDialog::MakePaper(int mode)
        {
        HDC                         lhDC;
        int                                     Align;
        float           xf,yf;
        int             x,y;
        float           xfe,yfe;
        WORD                        Items;
        char            Srch[55];
        char            Font[50];
        LPSTR           PFont=Font;
        int                                     FontSize;
        int                         Weight;
        HFONT                       FontObj,OldFont;
        int             cnt;
        int             Italic;
        LPRECT                      Prec;
        RECT            rec;
        char            PText[200];
        LPSTR           PPText=PText;
        char            OText[200];
        LPSTR           POText=OText;
        int                                     OType;
        int                                     FieldNumber;
        float           start_x;
        float                   start_y;
        float                   end_x;
        float                   end_y;
        int             PrgTmpHdl;
        char            Base_Name[100];
        int                                     Rtn = 0;
        LPSTR               AppName="Windows";
        LPSTR               KeyName="Device";
        LPSTR               Default="";
        char        *DeviceName;
        char        *DriverName;
        char        *OutputName;
        char        *Name;
        char        Token1[100];
        char        Token2[100];
        char        Token3[100];
        char        RetString[50];
        int         Size = 45;
        DOCINFO             PrtInfo;
DOCINFO FAR *   PPrtInfo;
        int                                 XPixels_Inch;
        int                                 YPixels_Inch;
```

```
if (RdyCode == 0) return;
RdyCode = 0;
SaveDetail();

Prec = &rec;

if (mode == 1)
        {
        GetProfileString(AppName,KeyName,Default,RetString,Size);

Name = strtok(RetString,".");
        strcpy(Token1,Name);
        DeviceName = Token1;

Name = strtok(NULL,".");
        strcpy(Token2,Name);
        DriverName = Token2;

Name = strtok(NULL,".");
        strcpy(Token3,Name);
        OutputName = Token3;

lhDC = CreateDC(DriverName,DeviceName,OutputName,PprntData);
//      lhDC = CreateDC(DriverName,DeviceName,OutputName,NULL);

PrtInfo.cbSize = 7;
PrtInfo.lpszDocName = "GemCert";
        PrtInfo.lpszOutput = NULL;

PPrtInfo = &PrtInfo;

StartDoc(lhDC,PPrtInfo);
        StartPage(lhDC);

if (lhDC == NULL)
                {
                MessageBox(HWindow,"Could Not Open Printer!","System Error."
                ,MB_OK | MB_ICONEXCLAMATION | MB_TASKMODAL);
                }

SetCursor(Cur_Wait);

rec.left = 0;
        rec.top = 0;
        rec.right = GetDeviceCaps(lhDC,HORZRES);
        rec.bottom = GetDeviceCaps(lhDC,VERTRES);
        }
    else
    { lhDC = GetDC(HWindow);
XPixels_Inch = GetDeviceCaps(lhDC,LOGPIXELSX)/2.5;
        YPixels_Inch = GetDeviceCaps(lhDC,LOGPIXELSY)/2.5;

rec.left = 218;
        rec.top = 235;
        rec.right = XSize*XPixels_Inch+218;
        rec.bottom = YSize*YPixels_Inch+235;
        }

Rectangle(lhDC,rec.left,rec.top,rec.right,rec.bottom);
```

```
Items = SendMessage(GetDlgItem(HWindow,105),LB_GETCOUNT,0,0L);
for (cnt = 0;cnt < Items;cnt=cnt+1)
    {
    SendMessage(GetDlgItem(HWindow,105),LB_GETTEXT,cnt,(LONG) PXBuffer);
    Srch[0] = NULL;
    strcpy(Srch,WorkCert);
    strncat(Srch,PSepChr,1);
    strcat(Srch,PXBuffer);
    GTS.OPKSearch(TmpHdl,"",Srch,2,0);
    GTS.OPGetRec(TmpHdl,"",1);
    GTS.OPGetGlobal(TmpHdl,"Use",0,PXBuffer);
    if (strcmpi(PXBuffer,"1") == 0)
        {
        GTS.OPGetGlobal(TmpHdl,"Text",0,POText);
        GTS.OPGetGlobal(TmpHdl,"Type",0,PXBuffer);
        OType = 0;
        if (strcmpi(PXBuffer,"1") == 0) OType = 1;
        GTS.OPGetGlobal(TmpHdl,"X",0,PXBuffer);
        xf = atof(PXBuffer);
        GTS.OPGetGlobal(TmpHdl,"Y",0,PXBuffer);
        yf = atof(PXBuffer);
        GTS.OPGetGlobal(TmpHdl,"Font",0,PFont);
        GTS.OPGetGlobal(TmpHdl,"Size",0,PXBuffer);
        FontSize = atoi(PXBuffer);
        if (mode == 0) FontSize = FontSize/4;
        GTS.OPGetGlobal(TmpHdl,"Just",0,PXBuffer);
        if (strcmpi(PXBuffer,"1") == 0) Align = 1;
        if (strcmpi(PXBuffer,"2") == 0) Align = 2;
        if (strcmpi(PXBuffer,"3") == 0) Align = 3;
        GTS.OPGetGlobal(TmpHdl,"Bold",0,PXBuffer);
        if (strcmpi(PXBuffer,"0") == 0) Weight = 400;
        if (strcmpi(PXBuffer,"1") == 0) Weight = 700;
        GTS.OPGetGlobal(TmpHdl,"Italic",0,PXBuffer);
        if (strcmpi(PXBuffer,"0") == 0) Italic = 0;
        if (strcmpi(PXBuffer,"1") == 0) Italic = 1;

if (mode == 1)
            {
            x = xf*ScaleConv*rec.right/XSize;
            y = yf*ScaleConv*rec.bottom/YSize;
            }
        else
            {
            x = xf*ScaleConv*XPixels_Inch+218;
            y = yf*ScaleConv*YPixels_Inch+235;
            } if (Align == 1)
            {
            SetTextAlign(lhDC,TA_LEFT);
            }
        if (Align == 2)
            {
            SetTextAlign(lhDC,TA_CENTER);
            }
        if (Align == 3)
            {
            SetTextAlign(lhDC,TA_RIGHT);
            }

FontObj = CreateFont(FontSize,0,0,0,Weight,Italic,0,0,ANSI_CHARSET
                            ,OUT_CHARACTER_PRECIS,CLIP_CHARACTER_PRECIS
```

```
                            ,PROOF_QUALITY,DEFAULT_PITCH|FF_DONTCARE
                            ,PFont);

OldFont = SelectObject(lhDC,FontObj);

if (OType == 1)
                    {
                    strcpy(PPText,POText);
                    }
            else
                    {
                    GTS.OPGetGlobal(TmpHdl,"Field",0,PXBuffer);
                    FieldNumber = atoi(PXBuffer);
                    GTS.OPGetGlobal(FakeHdl,"",FieldNumber,PXBuffer);
                    strcpy(PPText,PXBuffer);
                    }

ExtTextOut(lhDC,x,y,ETO_CLIPPED,Prec,PPText,strlen(PPText),NULL);

SelectObject(lhDC,OldFont);
            DeleteObject(FontObj);
            }
    } strcpy(Base_Name,Base_Path);
strcat(Base_Name,"CaGraph");
PrgTmpHdl = GTS.OPTableOpen(Base_Name,0);

strcpy(PXBuffer,PWorkCert);
Rtn = GTS.OPKSearch(PrgTmpHdl,"",PXBuffer,1,0);
if (Rtn == 0)
        {

GTS.OPGetRec(PrgTmpHdl,"",1);

GTS.OPGetGlobal(PrgTmpHdl,"G1B",0,PXBuffer);
        if (strcmpi(PXBuffer,"1") == 0)
                {
                GTS.OPGetGlobal(PrgTmpHdl,"G1X1",0,PXBuffer);
                xf = atof(PXBuffer);
                GTS.OPGetGlobal(PrgTmpHdl,"G1Y1",0,PXBuffer);
                yf = atof(PXBuffer);
                GTS.OPGetGlobal(PrgTmpHdl,"G1X2",0,PXBuffer);
                xfe = atof(PXBuffer);
                GTS.OPGetGlobal(PrgTmpHdl,"G1Y2",0,PXBuffer);
                yfe = atof(PXBuffer);
                if (mode == 1)
                        {
                        start_x = xf*ScaleConv*rec.right/XSize;
                        start_y = yf*ScaleConv*rec.bottom/YSize;
                        end_x = xfe*ScaleConv*rec.right/XSize;
                        end_y = yfe*ScaleConv*rec.bottom/YSize;
                        }
                else
                        {
                        start_x = xf*ScaleConv*XPixels_Inch+218;
                        start_y = yf*ScaleConv*YPixels_Inch+235;
                        end_x = xfe*ScaleConv*XPixels_Inch;
                        end_y = yfe*ScaleConv*YPixels_Inch;
                        }
                CiexyGraph(start_x,start_y,end_x,end_y,lhDC,mode);
                }
```

```
            GTS.OPGetGlobal(PrgTmpHdl,"G2B",0,PXBuffer);
            if (strcmpi(PXBuffer,"1") == 0)
                {
                    GTS.OPGetGlobal(PrgTmpHdl,"G2X1",0,PXBuffer);
                    xf = atof(PXBuffer);
                    GTS.OPGetGlobal(PrgTmpHdl,"G2Y1",0,PXBuffer);
                    yf = atof(PXBuffer);
                    GTS.OPGetGlobal(PrgTmpHdl,"G2X2",0,PXBuffer);
                    xfe = atof(PXBuffer);
                    GTS.OPGetGlobal(PrgTmpHdl,"G2Y2",0,PXBuffer);
                    yfe = atof(PXBuffer);
                    if (mode == 1)
                        {
                            start_x = xf*ScaleConv*rec.right/XSize;
                            start_y = yf*ScaleConv*rec.bottom/YSize;
                            end_x = xfe*ScaleConv*rec.right/XSize;
                            end_y = yfe*ScaleConv*rec.bottom/YSize;
                        }
                    else
                        {
                            start_x = xf*ScaleConv*XPixels_Inch+218;
                            start_y = yf*ScaleConv*YPixels_Inch+235;
                            end_x = xfe*ScaleConv*XPixels_Inch;
                            end_y = yfe*ScaleConv*YPixels_Inch;
                        }
                    CielabGraph(start_x,start_y,end_x,end_y,lhDC,mode);
                }

GTS.OPGetGlobal(PrgTmpHdl,"G3B",0,PXBuffer);
            if (strcmpi(PXBuffer,"1") == 0)
                {
                    GTS.OPGetGlobal(PrgTmpHdl,"G3X1",0,PXBuffer);
                    xf = atof(PXBuffer);
                    GTS.OPGetGlobal(PrgTmpHdl,"G3Y1",0,PXBuffer);
                    yf = atof(PXBuffer);
                    GTS.OPGetGlobal(PrgTmpHdl,"G3X2",0,PXBuffer);
                    xfe = atof(PXBuffer);
                    GTS.OPGetGlobal(PrgTmpHdl,"G3Y2",0,PXBuffer);
                    yfe = atof(PXBuffer);
                    if (mode == 1)
                        {
                            start_x = xf*ScaleConv*rec.right/XSize;
                            start_y = yf*ScaleConv*rec.bottom/YSize;
                            end_x = xfe*ScaleConv*rec.right/XSize;
                            end_y = yfe*ScaleConv*rec.bottom/YSize;
                        }
                    else
                        {
                            start_x = xf*ScaleConv*XPixels_Inch+218;
                            start_y = yf*ScaleConv*YPixels_Inch+235;
                            end_x = xfe*ScaleConv*XPixels_Inch;
                            end_y = yfe*ScaleConv*YPixels_Inch;
                        }
                    HueGraph(start_x,start_y,end_x,end_y,lhDC,mode);
                }

}
GTS.OPTableClose(PrgTmpHdl);
if (mode == 1)
    {
        EndPage(lhDC);
```

```
        EndDoc(lhDC);
        DeleteDC(lhDC);
        SetCursor(Cur_Arrow);
        }
else
{
        ReleaseDC(HWindow,lhDC);
        }
RdyCode = 1;

}
```

We claim:

1. A device for measuring characteristics of a gemstone by detecting the light frequency response of said gemstone under illumination comprising:

an optically clear mounting structure for supporting a gemstone thereon;

a light source unit substantially surrounding said mounting structure and gemstone thereon and having a light source creating uniform lighting enclosing said gemstone on said mounting structure and creating a light image of said gemstone, said light image comprising a plurality of light frequencies, an optical band pass filter coupled to said light source unit and receiving said light image and a selected frequency spectrum for subdividing the frequency spectrum of the image into individual wavelengths, said filter having an output;

a detector array coupled to said filter and the output of said band pass filter and separating said light image into a plurality of pixels and establishing spectral data of each pixel of the light image of said gemstone suitable for processing into definition of a gemstone characteristic.

2. The device of claim 1, wherein said detector array has an output of spectral data related to said spectral information, and including a processing system coupled to said detector array output and receiving and processing said spectral data to obtain the spectral information of the gemstone including said pixels contained within said gemstone relating to said characteristics.

3. The device of claim 2, wherein said processing system comprises:

a personal computer;

an input device connected to said detector array output; and an input/output terminal.

4. The device of claim 2, wherein said filter includes a wavelength control input for tuning said filter to individual wavelength information of the light image, and said processing system having an output connected said control input to tune said filter.

5. The device of claim 2, further comprising means for displaying said spectral data.

6. The device of claim 1, wherein said light source unit unit includes a fiber optic annular ring and a cable carrying white light having a Kelvin Temperature approximately equal to 5900° K.

7. The device of claim 1, wherein said detector array is a Charged Coupled Device.

8. The device of claim 7, wherein said Charged Coupled Device includes a cooling means to improve the signal-to-noise ratio of the Charged Coupled Device.

9. The device of claim 1, wherein said light source unit includes an enclosure having a substantially spherical interior wall enclosing said mounting structure, said interior wall having an optically white interior surface.

10. The device of claim 9, wherein said light source unit includes a light unit external to said spherical wall and said spherical wall includes a common entrance and exit opening aligned with said light unit and transmitting light from the light unit into said spherical wall and transmitting light projected from said spherical wall.

11. The device of claim 8, comprising heating control means coupled to said enclosure to regulating the temperature within the enclosure.

12. The device of claim 1, including an adjustable support connected to said light source unit for adjusting the angular orientation of the light transmitted through said opening and thereby the angle of lighting said gemstone is adjustable to provide multiple lighting angles.

13. The device of claim 12, wherein the gemstone has an exterior surface and said multiple angles include angles without direct reflection of light off the exterior of said gemstone.

14. A method for grading gemstones comprising the steps of:

placing a gemstone having an outer surface within an analysis chamber, said chamber having an opening and an external selected reference spot for spectral response analysis of the gemstone;

illuminating said chamber and said gemstone and through said opening including said reference spot;

calibrating the spectral response of said reference spot;

determining at least one perimeter portion of said gemstone; and determining the average spectral response of said at least a portion of said gemstone.

15. The method of grading gemstones according to claim 14, including the step of creating a representative light image of said gemstone.

16. The method of grading gemstones according to claim 15, including illuminating said gemstone from successive different positions for creating said representative light image of said gemstone.

17. The method of grading gemstone according to claim 15, including determining the average spectral response for the representative light image of said gemstone and for said portion of representative image constructed from said multiple light positions.

18. The method of grading gemstones according to claim 14, including the step of determining the average spectral response of said at least one perimeter portion of said gemstone by directing said portion into a plurality of separate pixels and including the steps of;

determining the number of pixels located within said perimeter portion of said gemstone;

summing the spectral response of each one of said pixels located within and perimeter portion to obtain an aggregate value; and dividing said aggregate value by said number of said pixels.

19. The method of grading gemstones according to claim 14, said gemstone having a selected table, and including the step of placing said gemstone with said table faced down.

20. The method of grading gemstones according to claim 14, wherein said step of illuminating said gemstone comprises the step of illuminating said gemstone with a distributed and indirect white light.

21. The method of grading gemstones according to claim 14, including the step of converting said information to data in accordance with a standardized color nomenclature system represented as a mathematical function.

22. The method of claim 21, wherein said standardized color nomenclature system comprises the CIE color system.

23. A method for grading illuminated gemstones comprising the steps of:

placing an illuminated gemstone within a field of view of a band pass filter dividing said illuminated gemstone into a plurality of pixels, and sensing the output wavelengths of said filter and thereby a light characteristic of each pixel and establishing a gray scale of the gemstone image;

identifying a set of said sensed pixels comprising an image of said gemstone; and processing said set of individual wavelength responses of said set of sensed pixels to describe said gemstone in a standard color nomenclature.

24. The method of claim 23 further comprising the step of illuminating said gemstone with multiple lighting angles.

25. The method of constructing an image of a gemstone, comprising forming a series of individual different images and constructing a single image of said gemstone from said series of individual different images.

26. The method of claim 25, wherein said forming includes illuminating the gemstone at different angles.

* * * * *